US008236296B2

(12) United States Patent
Rosen et al.

(10) Patent No.: US 8,236,296 B2

(45) Date of Patent: Aug. 7, 2012

(54) BIOLOGICAL BYPASS BRIDGE WITH SODIUM CHANNELS, CALCIUM CHANNELS AND/OR POTASSIUM CHANNELS TO COMPENSATE FOR CONDUCTION BLOCK IN THE HEART

(75) Inventors: Michael R Rosen, New York, NY (US); Peter R. Brink, Setauket, NY (US); Ira S. Cohen, Stony Brook, NY (US); Richard B Robinson, Cresskill, NJ (US); Peter Danilo, Jr., Hopewell, NJ (US)

(73) Assignees: The Trustees of Columbia University in the City of New York, New York, NY (US); The Research Foundation of State University of New York, Albany, NY (US)

( * ) Notice: Subject to any disclaimer, the term of this patent is extended or adjusted under 35 U.S.C. 154(b) by 473 days.

(21) Appl. No.: 11/490,760

(22) Filed: Jul. 21, 2006

(65) Prior Publication Data

US 2007/0053886 A1 Mar. 8, 2007

Related U.S. Application Data

(60) Provisional application No. 60/781,723, filed on Mar. 14, 2006, provisional application No. 60/704,210, filed on Jul. 29, 2005, provisional application No. 60/701,312, filed on Jul. 21, 2005.

(51) Int. Cl.

| | |
|---|---|
| ***A01N 63/00*** | (2006.01) |
| ***A61K 48/00*** | (2006.01) |
| ***C12N 15/63*** | (2006.01) |
| ***C07H 21/04*** | (2006.01) |

(52) U.S. Cl. .................... 424/93.21; 435/455; 536/23.5; 536/24.1

(58) Field of Classification Search ............... 424/93.21; 435/455; 536/23.5, 24.1

See application file for complete search history.

(56) References Cited

U.S. PATENT DOCUMENTS

| | | | |
|---|---|---|---|
| 6,060,271 | A | 5/2000 | Walewski et al. |
| 6,690,970 | B1 | 2/2004 | Taheri et al. |
| 6,783,979 | B2 | 8/2004 | Rosen et al. |
| 2002/0155101 | A1 | 10/2002 | Donahue et al. |
| 2004/0137621 | A1 * | 7/2004 | Rosen et al. |
| 2004/0143238 | A1 | 7/2004 | Lee |
| 2007/0099268 | A1 | 5/2007 | Cohen et al. |

FOREIGN PATENT DOCUMENTS

| | | | |
|---|---|---|---|
| WO | WO 02/19966 | A2 * | 3/2002 |
| WO | WO 2004/065580 | | 8/2004 |
| WO | WO 2005/062857 | | 7/2005 |
| WO | WO 2005/062857 | A2 * | 7/2005 |

OTHER PUBLICATIONS

O'Grady et al., 2005, The International Journal of Biochemistry & Cell Biology, vol. 37, p. 1578-1594.*
Kaupp et al., 2001, Annual Review of Physiology, vol. 63, p. 235-257.*
Kaye et al., 1990, Proc. Natl. Acad. Sci. USA, vol. 87, pp. 6922-6926.*
Skolnick et al., 2000, Trends in Biotech, vol. 18, p. 34-39.*
Tomasinsig et al., 2005, Current Protein and Peptide Science, vol. 6, p. 23-34.*
Smallwood et al., 2002 Virology, vol. 304, p. 135-145.*
Chattopadhyay et al., 2004, Virus Research, vol. 99, p. 139-145.*
Trimmer et al., 1989, Neuron, vol. 3, No. 1, p. 33-49.*
Fehrer et al., 2005, Experimental Gerontology, vol. 40, p. 926-930.*
Orlic, D. et al. "Bone marrow cells regenerated infarcted myocardium" Nature Apr. 5, 2001; 410: 701-705.
Perin, E. C. et al "Adult stem cell therapy in perspective" Circulation 2003; 107: 935-938.
Robinson, R. B. et al " Hyperpolarizaiton-activated cation currents: from molecules to physiological function" Annu. Rev. Physiol. 2003 65: 453-480.
Strauer B. E. et al "Repair of infarcted myocardium by autologous intracoronary mononuclear bone marrow cell transplantation in humans" Circulation 2002; 106: 1913-1918.
U.S. Appl. No. 60/701,312, filed Jul. 21, 2005, Rosen et al.
U.S. Appl. No. 60/704,210, filed Jul. 29, 2005, Rosen et al.
U.S. Appl. No. 60/781,723, filed Mar. 14, 2006, Rosen et al.
U.S. Appl. No. 11/490,997, filed Jul. 21, 2006, Rosen et al.
Plotnikov, A. N. et al., "Human mesenchymal stem cells transfected with HCN2 as a gene delivery system to induce pacemaker function in canine heart", Clinical Science—Lippincott Williams & Wilkins, US (2003), vol. 108:17, pp. IV-547, [Abstract 2494].
Plotnikov, A, N. et al. Biological Pacemaker Implated in Canine Left Bundle Branch Provides Ventricular Escape Rhythms that have Physiologically Acceptable Rules, Ciruclation, (2004) vol. 109, pp. 506-512.
Potapova, I. et al., "Human mesenchymal stems cells as a gene delivery system to create cardiac pacemakers", Circulation Research, (2004), vol. 94:7, pp. 952-959.
Valiunas, V. et al., "Human mesenchymal stem cells make cardiac connexins and form functional gap junctions", Journal of Physiology, (2004), vol. 555:3, pp. 617-626.
Wang, J., et al "Regulation of Hyperpolarization-activated HCN Channel Gating and cAMP Modulation due to Interactions of COOH Terminus and Core Transmembrane Regions", J. of Gen. Phys. (Sep. 30, 2001) vol. 118:3 p. 237-250.
International Search Report of PCT/US2006/028857 filed Jul. 21, 2006.

* cited by examiner

*Primary Examiner* — Shin-Lin Chen

(74) *Attorney, Agent, or Firm* — Evans & Molinelli PLLC; Judith Evans

(57) ABSTRACT

This invention provides a bypass bridge comprising a tract of gap junction-coupled cells having a first end and a second end, both ends capable of being attached to two selected sites in a heart so as to allow the conduction of a pacemaker and/or electrical signal/current across the tract between the two sites, wherein the cells functionally express a sodium channel. The invention also provides related methods of making the bypass bridge, methods of implanting same in a heart, and methods of treating a disorder associated with an impaired conduction in a subject's heart.

25 Claims, 17 Drawing Sheets

```
mouse_hcn2_protein   MDARGGGGRPGDSPGTTPAPGPPPPPPPPAP...PQPQPP    37
human_hcn2_protein   MDARGGGGRPGeSPGaTPAPGPPPPPPPapPqqqPpPpPP    40

mouse_hcn2_protein   PAPPPN..PTTPSHP........ESADEPGPRARLCSRDS    67
human_hcn2_protein   PAPPPgpgPapPqHPpraealppEaADEgGPRgRLrSRDS    80

mouse_hcn2_protein   AC....TPG...AAKGGANGECGRGEPQCS...PEGPARG    97
human_hcn2_protein   sCgrpgTPGaastAKGspNGECGRGEPQCSpagPEGPARG   120

mouse_hcn2_protein   PKVSFSCRGAAS....GPSAAEEAGSEEAGPAGEPRGSQA   133
human_hcn2_protein   PKVSFSCRGAASgpapGPgpAEEAGSEEAGPAGEPRGSQA   160

mouse_hcn2_protein   SFLQRQFGALLQPGVNKFSLRMFGSQKAVEREQERVKSAG   173
human_hcn2_protein   SFmQRQFGALLQPGVNKFSLRMFGSQKAVEREQERVKSAG   200

mouse_hcn2_protein   AWIIHPYSDFRFYWDFTMLLFMVGNLIIIPVGITFFKDET   213
human_hcn2_protein   AWIIHPYSDFRFYWDFTMLLFMVGNLIIIPVGITFFKDET   240

mouse_hcn2_protein   TAPWIVFNVVSDTFFLMDLVLNFRTGIVIEDNTEIILDPE   253
human_hcn2_protein   TAPWIVFNVVSDTFFLMDLVLNFRTGIVIEDNTEIILDPE   280

mouse_hcn2_protein   KIKKKYLRTWFVVDFVSSIPVDYIFLIVEKGIDSEVYKTA   293
human_hcn2_protein   KIKKKYLRTWFVVDFVSSIPVDYIFLIVEKGIDSEVYKTA   320

mouse_hcn2_protein   RALRIVRFTKILSLLRLLRLSRLIRYIHQWEEIFHMTYDL   333
human_hcn2_protein   RALRIVRFTKILSLLRLLRLSRLIRYIHQWEEIFHMTYDL   360

mouse_hcn2_protein   ASAVMRICNLISMMLLLCHWDGCLQFLVPMLQDFPSDCWV   373
human_hcn2_protein   ASAVMRICNLISMMLLLCHWDGCLQFLVPMLQDFPrnCWV   400

mouse_hcn2_protein   SINNMVNHSWSELYSFALFKAMSHMLCIGYGRQAPESMTD   413
human_hcn2_protein   SINgMVNHSWSELYSFALFKAMSHMLCIGYGRQAPESMTD   440

mouse_hcn2_protein   IWLTMLSMIVGATCYAMFIGHATALIQSLDSSRRQYQEKY   453
human_hcn2_protein   IWLTMLSMIVGATCYAMFIGHATALIQSLDSSRRQYQEKY   480

mouse_hcn2_protein   KQVEQYMSFHKLPADFRQKIHDYYEHRYQGKMFDEDSILG   493
human_hcn2_protein   KQVEQYMSFHKLPADFRQKIHDYYEHRYQGKMFDEDSILG   520

mouse_hcn2_protein   ELNGPLREEIVNFNCRKLVASMPLFANADPNFVTAMLTKL   533
human_hcn2_protein   ELNGPLREEIVNFNCRKLVASMPLFANADPNFVTAMLTKL   560

mouse_hcn2_protein   KFEVFQPGDYIIREGTIGKKMYFIQHGVVSVLTKGNKEMK   573
human_hcn2_protein   KFEVFQPGDYIIREGTIGKKMYFIQHGVVSVLTKGNKEMK   600

mouse_hcn2_protein   LSDGSYFGEICLLTRGRRTASVRADTYCRLYSLSVDNFNE   613
human_hcn2_protein   LSDGSYFGEICLLTRGRRTASVRADTYCRLYSLSVDNFNE   640

mouse_hcn2_protein   VLEEYPMMRRAFETVAIDRLDRIGKKNSILLHKVQHDLSS   653
human_hcn2_protein   VLEEYPMMRRAFETVAIDRLDRIGKKNSILLHKVQHDLnS   680

mouse_hcn2_protein   GVFNNQENAIIQEIVKYDREMVQQAELGQRVGLFPPPPPP   693
human_hcn2_protein   GVFNNQENAIIQEIVKYDREMVQQAELGQRVGLFPPPPPP   720

mouse_hcn2_protein   .QVTSAIATLQQAVAMSFCPQVARPLVGPLALGSPRLVRR   732
human_hcn2_protein   pQVTSAIATLQQAaAMSFCPQVARPLVGPLALGSPRLVRR   760

mouse_hcn2_protein   APPGPLPPAASPGPP.AASPPAAPSSPRAPRTSPYG.VPG   770
human_hcn2_protein   pPPGPaPaAASPGPPppASPPgAPaSPRAPRTSPYGglPa   800

mouse_hcn2_protein   SPATRVGPALPARRLSRASRPLSASQPSLPHGVPAPSPAA   810
human_hcn2_protein   aPla..GPALPARRLSRASRPLSASQPSLPHGaPg..PAA   836

mouse_hcn2_protein   SARPASSSTPRLGPAPTARTAAPSPDRRDSASPGAASGLD   850
human_hcn2_protein   StRPASSSTPRLrPtPaARaAAPSPDRRDSASPGAAgGLD   876

mouse_hcn2_protein   PLDSARSRLSSNL                              863
human_hcn2_protein   PqDSARSRLSSNL                              889
```

Figure 1

Human HCN212 Chimeric Polypeptide

```
MDARGGGGRPGESPGASPTTGPPPPPPPAPPQQQPPPPPPPAPPPGPGPAPPQHPPRAEA   60
LPPEAADEGGPRGRLRSRDSSCGRPGTPGAASTAKGSPNGECGRGEPQCSPAGPEGPARG  120
PKVSFSCRGAASGPAPGPGPAEEAGSEEAGPAGEPRGSQASFMQRQFGALLQPGVNKFSL  180
RMFGSQKAVEREQERVKSAGAWIIHPYSDFRFYWDLIMLIMMVGNLVIIPVGITFFTEQT  240
TTPWIIFNVASDTVFLLDLIMNFRTGTVNEDSSEIILDPKVIKMNYLKSWSVVDFISSIP  300
VDYIFLIVEKGMDSEVYKTARALRIVRFTKILSLLRLLRLSRLIRYIHQWEEIFHMTYDL  360
ASAVVRIFNLIGMMLLLCHWDGCLQFLVPLLQDFPPDCWVSLNEMVNDSWGKQYSYALFK  420
AMSHMLCIGYGAQAPVSMSDLWITMLSMIVGATCYAMFVGHATALIQSLDSSRRQYQEKY  480
KQVEQYMSFHKLPADFRQKIHDYYEHRYQGKMFDEDSILGELNGPLREEIVNFNCRKLVA  540
SMPLFANADPNFVTAMLTKLKFEVFQPGDYIIREGTIGKKMYFIQHGVVSVLTKGNKEMK  600
LSDGSYFGEICLLTRGRRTASVRADTYCRLYSLSVDNFNEVLEEYPMMRRAFETVAIDRL  660
DRIGKKNSILLHKVQHDLNSGVFNNQENAIIQEIVKYDREMVQQAELGQRVGLFPPPPPP  720
PQVTSAIATLQQAAAMSFCPQVARPLVGPLALGSPRLVRRPPPGPAPAAASPGPPPPASP  780
PGAPASPRAPRTSPYGGLPAAPLAGPALPARRLSRASRPLSASQPSLPHGAPGPAASTRP  840
ASSSTPRLGPTPAARAAAPSPDRRDSASPGAAGGLDPQDSARSRLSSNL            889
```

Figure 2

Mouse HCN212 Chimeric Polypeptide

```
MDARGGGGRPGDSPGTTPAPGPPPPPPPPAPPQPQPPPAPPPNPTTPSHPESADEPGPRA   60
RLCSRDSACTPGAAKGGANGECGRGEPQCSPEGPARGPKVSFSCRGAASGPSAAEEAGSE  120
EAGPAGEPRGSQASFLQRQFGALLQPGVNKFSLRMFGSQKAVEREQERVKSAGAWIIHPY  180
SDFRFYWGLIMLIMMVGNLVIIPVGITFFTEQTTTPWIIFNVASDTVFLLDLIMNFRTGT  240
VNEDSSEIILDPKVIKMNYLKSWFVVDFISSIPVDYIFLIVEKGMDSEVYKTARALRIVR  300
FTKILSLLRLLRLSRLIRYIHQWEEIFHMTYDLASAVVRIFNLIGMMLLLCHWDGCLQFL  360
VPLLQDFPPDCWVSLNEMVNDSWGKQYSYALFKAMSHMLCIGYGAQAPVSMSDLWITMLS  420
MIVGATCYAMFVGHATALIQSLDSSRRQYQEKYKQVEQYMSFHKLPADFRQKIHDYYEHR  480
YQGKMFDEDSILGELNGPLREEIVNFNCRKLVASMPLFANADPNFVTAMLTKLKFEVFQP  540
GDYIIREGTIGKKMYFIQHGVVSVLTKGNKEMKLSDGSYFGEICLLTRGRRTASVRADTY  600
CRLYSLSVDNFNEVLEEYPMMRRAFETVAIDRLDRIGKKNSILLHKVQHDLSSGVFNNQE  660
NAIIQEIVKYDREMVQQAELGQRVGLFPPPPPPQVTSAIATLQQAVAMSFCPQVARPLVG  720
PLALGSPRLVRRAPPGPLPPAASPGPPAASPPAAPSSPRAPRTSPYGVPGSPATRVGPAL  780
PARRLSRASRPLSASQPSLPHGVPAPSPAASARPASSSTPRLGPAPTARTAAPSPDRRDS  840
ASPGAASGLDPLDSARSRLSSNL                                       863
```

Figure 3 hMSC-HeLa Cx43
$I_j$
100 pA $I_j$
2 s
200 pA hMSC-HeLa Cx40
$I_j$
200 pA $I_j$
2 s
200 pA

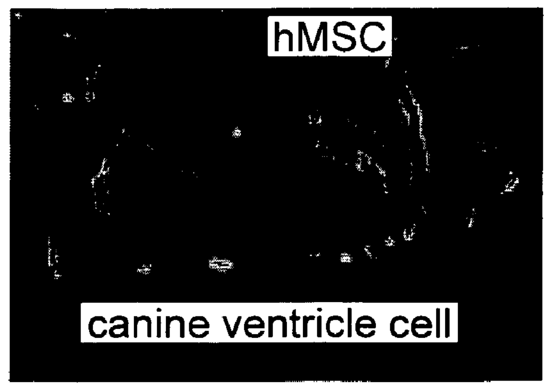
FIG.7A
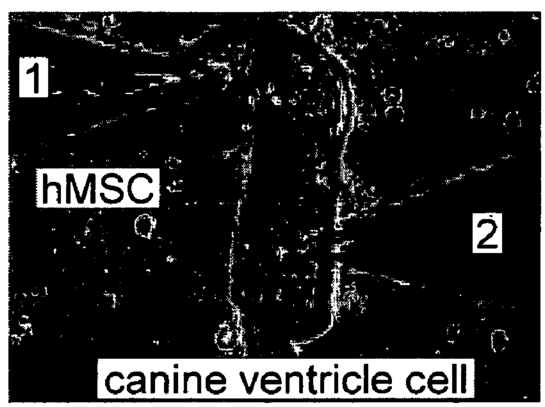
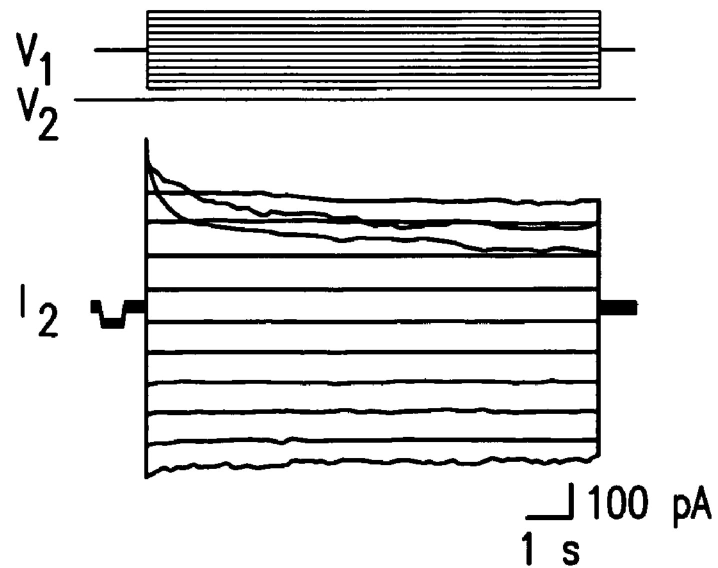
FIG.7B

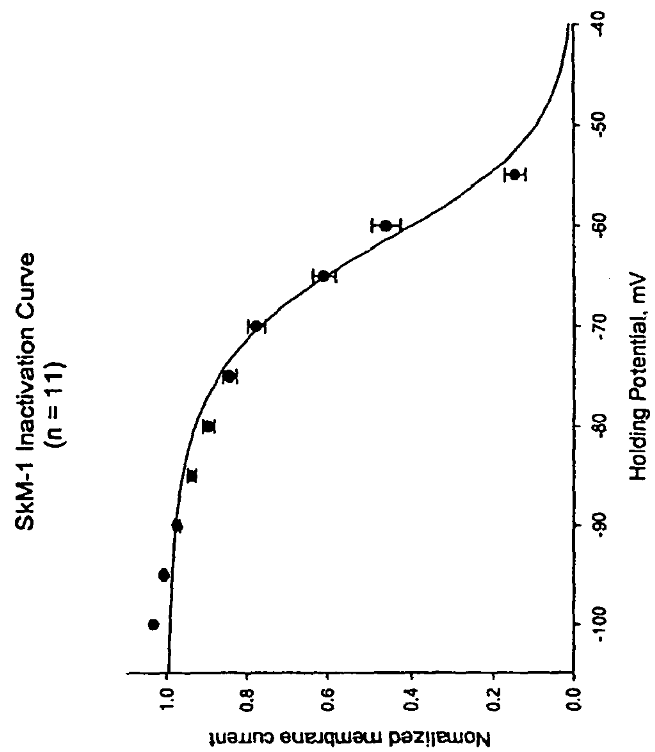
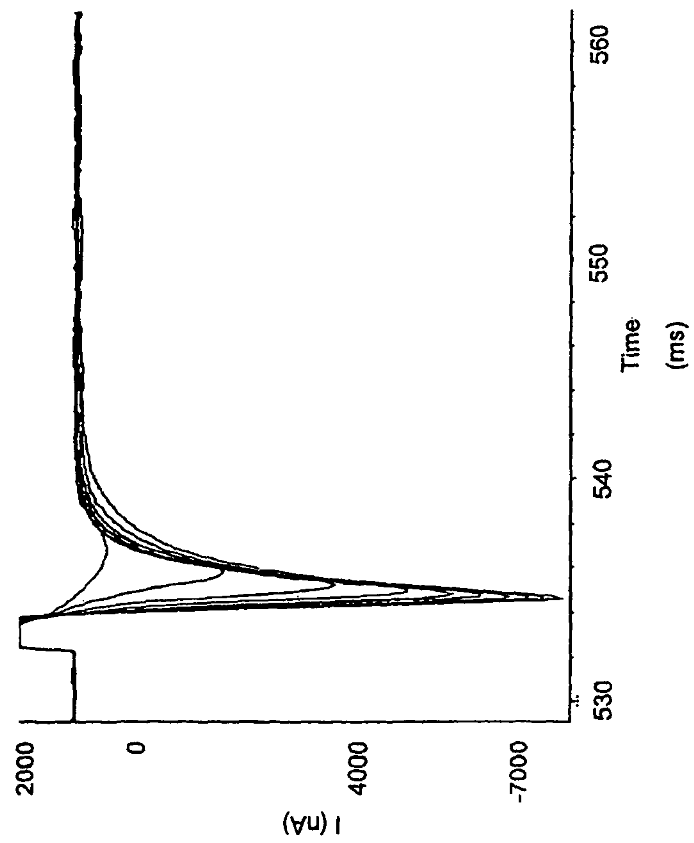
Figure 8

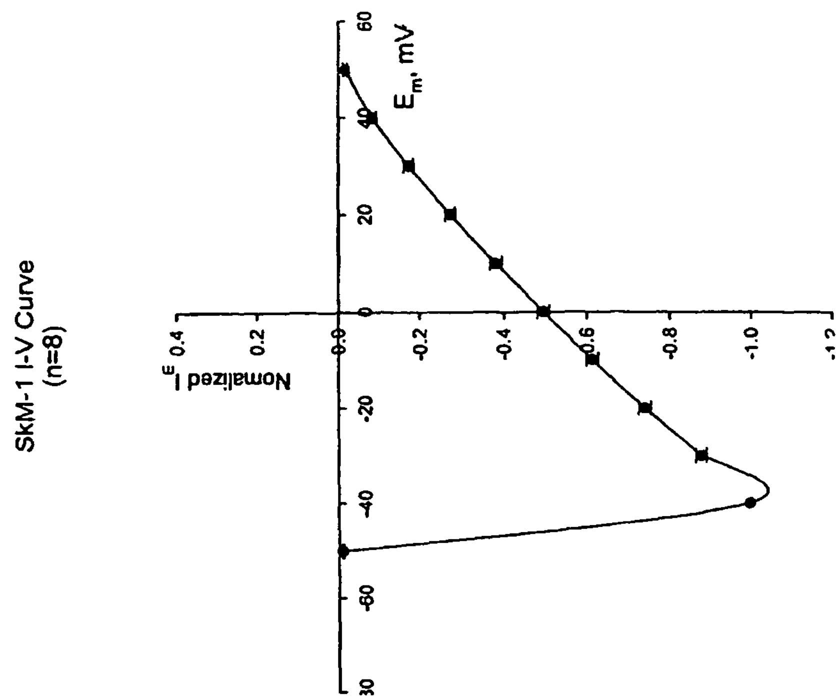
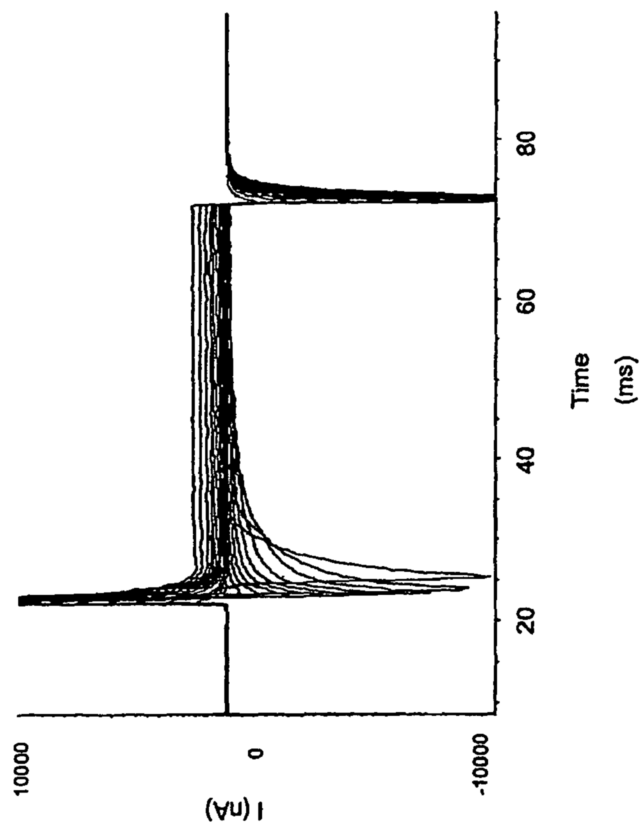
Figure 9

SEQUENCE LISTING

<160> NUMBER OF SEQ ID NOS: 28

<210> SEQ ID NO 1
<211> LENGTH: 2670
<212> TYPE: DNA
<213> ORGANISM: Homo sapiens

<400> SEQUENCE: 1

```
atggacgcgc gcgggggcgg cgggcggccc ggggagagcc cgggcgcgag ccccacgacc     60
gggccgccgc cgccgccgcc gcccgcgccc ccccaacagc agccgccgcc gccgccgccg    120
cccgcgcccc ccccgggccc cgggcccgcg cccccccagc acccgccccg ggccgaggcg    180
ttgcccccgg aggcggcgga tgagggcggc ccgcggggcc ggctccgcag ccgcgacagc    240
tcgtgcggcc gccccggcac cccgggcgcg gcgagcacgg ccaagggcag cccgaacggc    300
gagtgcgggc gcggcgagcc gcagtgcagc ccgcggggc ccgagggccc ggcgcggggg    360
cccaaggtgt cgttctcgtg ccgcggggcg gcctcggggc ccgcgccggg gccggggccg    420
gcggaggagg cgggcagcga ggaggcgggc ccggcggggg agccgcgcgg cagccaggcc    480
agcttcatgc agcgccagtt cggcgcgctc ctgcagccgg gcgtcaacaa gttctcgctg    540
cggatgttcg gcagccagaa ggccgtggag cgcgagcagg agcgcgtcaa gtcggcgggg    600
gcctggatca tccacccgta cagcgacttc aggttttact gggatttaat aatgcttata    660
atgatggttg gaaatctagt catcatacca gttggaatca cattctttac agagcaaaca    720
acaacaccat ggattatttt caatgtggca tcagatacag ttttcctatt ggacctgatc    780
atgaatttta ggactgggac tgtcaatgaa gacagttctg aaatcatcct ggaccccaaa    840
gtgatcaaga tgaattattt aaaaagctgg tctgtggttg acttcatctc atccatccca    900
gtggattata tctttcttat tgtagaaaaa ggaatggatt ctgaagttta caagacagcc    960
agggcacttc gcattgtgag gtttacaaaa attctcagtc tcttgcgttt attacgactt   1020
tcaaggttaa ttagatacat acatcaatgg gaagagatat tccacatgac atatgatctc   1080
gccagtgcag tggtgagaat ttttaatctc atcggcatga tgctgctcct gtgccactgg   1140
gatggttgtc ttcagttctt agtaccacta ctgcaggact tcccaccaga ttgctgggtg   1200
tctttaaatg aaatggttaa tgattcttgg ggaaagcagt attcatacgc actcttcaaa   1260
gctatgagtc acatgctgtg cattgggtat ggagcccaag ccccagtcag catgtctgac   1320
ctctggatta ccatgctgag catgatcgtc ggggccacct gctatgccat gtttgtcggc   1380
catgccaccg ctttaatcca gtctctggac tcctcgcggc gccagtacca ggagaagtac   1440
aagcaggtgg agcagtacat gtccttccac aagctgccag ctgacttccg ccagaagatc   1500
cacgactact atgagcaccg ttaccagggc aagatgtttg acgaggacag catcctgggc   1560
gagctcaacg ggcccctgcg ggaggagatc gtcaacttca actgccggaa gctggtggcc   1620
tccatgccgc tgttcgccaa cgccgacccc aacttcgtca cggccatgct gaccaagctc   1680
aagttcgagg tcttccagcc gggtgactac atcatccgcg aaggcaccat cgggaagaag   1740
atgtacttca tccagcacgg cgtggtcagc gtgctcacta agggcaacaa ggagatgaag   1800
ctgtccgatg gctcctactt cggggagatc tgcctgctca cccggggccg ccgcacggcg   1860
agcgtgcggg ctgacaccta ctgccgcctc tattcgctga gcgtggacaa cttcaacgag   1920
gtgctggagg agtaccccat gatgcggcgc gccttcgaga cggtggccat cgaccgcctg   1980
gaccgcatcg gcaagaagaa ttccatcctc ctgcacaagg tgcagcatga cctcaactcg   2040
```

```
ggcgtattca acaaccagga gaacgccatc atccaggaga tcgtcaagta cgaccgcgag   2100

atggtgcagc aggccgagct gggtcagcgc gtgggcctct tcccgccgcc gccgccgccg   2160

ccgcaggtca cctcggccat cgccacgctg cagcaggcgg cggccatgag cttctgcccg   2220

caggtggcgc ggccgctcgt ggggccgctg gcgctcggct cgccgcgcct cgtgcgccgc   2280

ccgcccccgg ggcccgcacc tgccgccgcc tcacccgggc ccccgccccc cgccagcccc   2340

ccgggcgcgc ccgccagccc ccgggcaccg cggacctcgc cctacggcgg cctgcccgcc   2400

gccccccttg ctgggcccgc cctgcccgcg cgccgcctga gccgcgcgtc gcgcccactg   2460

tccgcctcgc agccctcgct gcctcacggc gcccccggcc ccgcggcctc cacacgcccg   2520

gccagcagct ccacaccgcg cttggggccc acgcccgctg cccgggccgc cgcgcccagc   2580

ccggaccgca gggactcggc ctcacccggc gccgccggcg gcctggaccc ccaggactcc   2640

gcgcgctcgc gcctctcgtc caacttgtga                                    2670
```

<210> SEQ ID NO 2
<211> LENGTH: 889
<212> TYPE: PRT
<213> ORGANISM: Homo sapiens

<400> SEQUENCE: 2

```
Met Asp Ala Arg Gly Gly Gly Gly Arg Pro Gly Glu Ser Pro Gly Ala
  1               5                  10                  15

Ser Pro Thr Thr Gly Pro Pro Pro Pro Pro Pro Pro Ala Pro Pro Gln
             20                  25                  30

Gln Gln Pro Pro Pro Pro Pro Pro Pro Ala Pro Pro Pro Gly Pro Gly
         35                  40                  45

Pro Ala Pro Pro Gln His Pro Pro Arg Ala Glu Ala Leu Pro Pro Glu
     50                  55                  60

Ala Ala Asp Glu Gly Gly Pro Arg Gly Arg Leu Arg Ser Arg Asp Ser
 65                  70                  75                  80

Ser Cys Gly Arg Pro Gly Thr Pro Gly Ala Ala Ser Thr Ala Lys Gly
                 85                  90                  95

Ser Pro Asn Gly Glu Cys Gly Arg Gly Glu Pro Gln Cys Ser Pro Ala
            100                 105                 110

Gly Pro Glu Gly Pro Ala Arg Gly Pro Lys Val Ser Phe Ser Cys Arg
        115                 120                 125

Gly Ala Ala Ser Gly Pro Ala Pro Gly Pro Gly Pro Ala Glu Glu Ala
    130                 135                 140

Gly Ser Glu Glu Ala Gly Pro Ala Gly Glu Pro Arg Gly Ser Gln Ala
145                 150                 155                 160

Ser Phe Met Gln Arg Gln Phe Gly Ala Leu Leu Gln Pro Gly Val Asn
                165                 170                 175

Lys Phe Ser Leu Arg Met Phe Gly Ser Gln Lys Ala Val Glu Arg Glu
            180                 185                 190

Gln Glu Arg Val Lys Ser Ala Gly Ala Trp Ile Ile His Pro Tyr Ser
        195                 200                 205

Asp Phe Arg Phe Tyr Trp Asp Leu Ile Met Leu Ile Met Met Val Gly
    210                 215                 220

Asn Leu Val Ile Ile Pro Val Gly Ile Thr Phe Phe Thr Glu Gln Thr
225                 230                 235                 240

Thr Thr Pro Trp Ile Ile Phe Asn Val Ala Ser Asp Thr Val Phe Leu
                245                 250                 255

Leu Asp Leu Ile Met Asn Phe Arg Thr Gly Thr Val Asn Glu Asp Ser
            260                 265                 270
```

```
Ser Glu Ile Ile Leu Asp Pro Lys Val Ile Lys Met Asn Tyr Leu Lys
        275                 280                 285

Ser Trp Ser Val Val Asp Phe Ile Ser Ser Ile Pro Val Asp Tyr Ile
    290                 295                 300

Phe Leu Ile Val Glu Lys Gly Met Asp Ser Glu Val Tyr Lys Thr Ala
305                 310                 315                 320

Arg Ala Leu Arg Ile Val Arg Phe Thr Lys Ile Leu Ser Leu Leu Arg
                325                 330                 335

Leu Leu Arg Leu Ser Arg Leu Ile Arg Tyr Ile His Gln Trp Glu Glu
            340                 345                 350

Ile Phe His Met Thr Tyr Asp Leu Ala Ser Ala Val Val Arg Ile Phe
        355                 360                 365

Asn Leu Ile Gly Met Met Leu Leu Leu Cys His Trp Asp Gly Cys Leu
    370                 375                 380

Gln Phe Leu Val Pro Leu Leu Gln Asp Phe Pro Pro Asp Cys Trp Val
385                 390                 395                 400

Ser Leu Asn Glu Met Val Asn Asp Ser Trp Gly Lys Gln Tyr Ser Tyr
                405                 410                 415

Ala Leu Phe Lys Ala Met Ser His Met Leu Cys Ile Gly Tyr Gly Ala
            420                 425                 430

Gln Ala Pro Val Ser Met Ser Asp Leu Trp Ile Thr Met Leu Ser Met
        435                 440                 445

Ile Val Gly Ala Thr Cys Tyr Ala Met Phe Val Gly His Ala Thr Ala
    450                 455                 460

Leu Ile Gln Ser Leu Asp Ser Ser Arg Arg Gln Tyr Gln Glu Lys Tyr
465                 470                 475                 480

Lys Gln Val Glu Gln Tyr Met Ser Phe His Lys Leu Pro Ala Asp Phe
                485                 490                 495

Arg Gln Lys Ile His Asp Tyr Tyr Glu His Arg Tyr Gln Gly Lys Met
            500                 505                 510

Phe Asp Glu Asp Ser Ile Leu Gly Glu Leu Asn Gly Pro Leu Arg Glu
        515                 520                 525

Glu Ile Val Asn Phe Asn Cys Arg Lys Leu Val Ala Ser Met Pro Leu
    530                 535                 540

Phe Ala Asn Ala Asp Pro Asn Phe Val Thr Ala Met Leu Thr Lys Leu
545                 550                 555                 560

Lys Phe Glu Val Phe Gln Pro Gly Asp Tyr Ile Ile Arg Glu Gly Thr
                565                 570                 575

Ile Gly Lys Lys Met Tyr Phe Ile Gln His Gly Val Val Ser Val Leu
            580                 585                 590

Thr Lys Gly Asn Lys Glu Met Lys Leu Ser Asp Gly Ser Tyr Phe Gly
        595                 600                 605

Glu Ile Cys Leu Leu Thr Arg Gly Arg Arg Thr Ala Ser Val Arg Ala
    610                 615                 620

Asp Thr Tyr Cys Arg Leu Tyr Ser Leu Ser Val Asp Asn Phe Asn Glu
625                 630                 635                 640

Val Leu Glu Glu Tyr Pro Met Met Arg Arg Ala Phe Glu Thr Val Ala
                645                 650                 655

Ile Asp Arg Leu Asp Arg Ile Gly Lys Lys Asn Ser Ile Leu Leu His
            660                 665                 670

Lys Val Gln His Asp Leu Asn Ser Gly Val Phe Asn Asn Gln Glu Asn
        675                 680                 685

Ala Ile Ile Gln Glu Ile Val Lys Tyr Asp Arg Glu Met Val Gln Gln
```

```
    690                 695                 700

Ala Glu Leu Gly Gln Arg Val Gly Leu Phe Pro Pro Pro Pro Pro Pro
705                 710                 715                 720

Pro Gln Val Thr Ser Ala Ile Ala Thr Leu Gln Gln Ala Ala Ala Met
                725                 730                 735

Ser Phe Cys Pro Gln Val Ala Arg Pro Leu Val Gly Pro Leu Ala Leu
            740                 745                 750

Gly Ser Pro Arg Leu Val Arg Arg Pro Pro Pro Gly Pro Ala Pro Ala
        755                 760                 765

Ala Ala Ser Pro Gly Pro Pro Pro Pro Ala Ser Pro Pro Gly Ala Pro
    770                 775                 780

Ala Ser Pro Arg Ala Pro Arg Thr Ser Pro Tyr Gly Gly Leu Pro Ala
785                 790                 795                 800

Ala Pro Leu Ala Gly Pro Ala Leu Pro Ala Arg Arg Leu Ser Arg Ala
                805                 810                 815

Ser Arg Pro Leu Ser Ala Ser Gln Pro Ser Leu Pro His Gly Ala Pro
            820                 825                 830

Gly Pro Ala Ala Ser Thr Arg Pro Ala Ser Ser Ser Thr Pro Arg Leu
        835                 840                 845

Gly Pro Thr Pro Ala Ala Arg Ala Ala Ala Pro Ser Pro Asp Arg Arg
    850                 855                 860

Asp Ser Ala Ser Pro Gly Ala Ala Gly Gly Leu Asp Pro Gln Asp Ser
865                 870                 875                 880

Ala Arg Ser Arg Leu Ser Ser Asn Leu
                885


<210> SEQ ID NO 3
<211> LENGTH: 2325
<212> TYPE: DNA
<213> ORGANISM: Homo sapiens

<400> SEQUENCE: 3

atggaggcag agcagcggcc ggcggcgggg gccagcgaag ggcgacccc tggactggag      60

gcggtgcctc ccgttgctcc cccgcctgcg accgcggcct caggtccgat ccccaaatct     120

gggcctgagc ctaagaggag gcaccttggg acgctgctcc agcctacggt caacaagttc     180

tcccttcggg tgttcggcag ccacaaagca gtggaaatcg agcaggagcg ggtgaagtca     240

gcgggggcct ggatcatcca cccctacagc gacttccggt tttactggga cctgatcatg     300

ctgctgctga tggtggggaa cctcatcgtc ctgcctgtgg gcatcacctt cttcaaggag     360

gagaactccc cgccttggat cgtcttcaac gtattgtctg atactttctt cctactggat     420

ctggtgctca acttccgaac gggcatcgtg gtggaggagg gtgctgagat cctgctggca     480

ccgcgggcca tccgcacgcg ctacctgcgc acctggttcc tggttgacct catctcttct     540

atccctgtgg attacatctt cctagtggtg gagctggagc cacggttgga cgctgaggtc     600

tacaaaacgg cacgggccct acgcatcgtt cgcttcacca agatcctaag cctgctgagg     660

ctgctccgcc tctcccgcct catccgctac atacaccagt gggaggagat ctttcacatg     720

acctatgacc tggccagtgc tgtggttcgc atcttcaacc tcattgggat gatgctgctg     780

ctatgtcact gggatggctg tctgcagttc ctggtgccca tgctgcagga cttccctccc     840

gactgctggg tctccatcaa ccacatggtg aaccactcgt ggggccgcca gtattcccat     900

gccctgttca aggccatgag ccacatgctg tgcattggct atgggcagca ggcacctgta     960

ggcatgcccg acgtctggct caccatgctc agcatgatcg taggtgccac atgctacgcc    1020
```

```
atgttcatcg gccatgccac ggcactcatc cagtccctgg actcttcccg gcgtcagtac   1080

caggagaagt acaagcaggt ggagcagtac atgtccttcc acaagctgcc agcagacacg   1140

cggcagcgca tccacgagta ctatgagcac cgctaccagg gcaagatgtt cgatgaggaa   1200

agcatcctgg gcgagctgag cgagccgctt cgcgaggaga tcattaactt cacctgtcgg   1260

ggcctggtgg cccacatgcc gctgtttgcc catgccgacc ccagcttcgt cactgcagtt   1320

ctcaccaagc tgcgctttga ggtcttccag ccgggggatc tcgtggtgcg tgagggctcc   1380

gtggggagga agatgtactt catccagcat gggctgctca gtgtgctggc ccgcggcgcc   1440

cgggacacac gcctcaccga tggatcctac tttggggaga tctgcctgct aactaggggc   1500

cggcgcacag ccagtgttcg ggctgacacc tactgccgcc tttactcact cagcgtggac   1560

catttcaatg ctgtgcttga ggagttcccc atgatgcgcc gggcctttga gactgtggcc   1620

atggatcggc tgctccgcat cggcaagaag aattccatac tgcagcggaa gcgctccgag   1680

ccaagtccag gcagcagtgg tggcatcatg gagcagcact tggtgcaaca tgacagagac   1740

atggctcggg gtgttcgggg tcgggccccg agcacaggag ctcagcttag tggaaagcca   1800

gtactgtggg agccactggt acatgcgccc cttcaggcag ctgctgtgac ctccaatgtg   1860

gccattgccc tgactcatca gcggggccct ctgcccctct cccctgactc tccagccacc   1920

ctccttgctc gctctgcttg gcgctcagca ggctctccag cttccccgct ggtgcccgtc   1980

cgagctggcc catgggcatc cacctcccgc ctgcccgccc cacctgcccg aaccctgcac   2040

gccagcctat cccgggcagg gcgctcccag gtctccctgc tgggtccccc tccaggagga   2100

ggtggacggc ggctaggacc tcggggccgc ccactctcag cctcccaacc ctctctgcct   2160

cagcgggcaa caggcgatgg ctctcctggg cgtaagggat caggaagtga gcggctgcct   2220

ccctcagggc tcctggccaa acctccaagg acagcccagc cccccaggcc accagtgcct   2280

gagccagcca caccccgggg tctccagctt tctgccaaca tgtaa                   2325
```

```
<210> SEQ ID NO 4
<211> LENGTH: 774
<212> TYPE: PRT
<213> ORGANISM: Homo sapiens

<400> SEQUENCE: 4

Met Glu Ala Glu Gln Arg Pro Ala Ala Gly Ala Ser Glu Gly Ala Thr
  1               5                  10                  15

Pro Gly Leu Glu Ala Val Pro Pro Val Ala Pro Pro Pro Ala Thr Ala
             20                  25                  30

Ala Ser Gly Pro Ile Pro Lys Ser Gly Pro Glu Pro Lys Arg Arg His
         35                  40                  45

Leu Gly Thr Leu Leu Gln Pro Thr Val Asn Lys Phe Ser Leu Arg Val
     50                  55                  60

Phe Gly Ser His Lys Ala Val Glu Ile Glu Gln Glu Arg Val Lys Ser
 65                  70                  75                  80

Ala Gly Ala Trp Ile Ile His Pro Tyr Ser Asp Phe Arg Phe Tyr Trp
                 85                  90                  95

Asp Leu Ile Met Leu Leu Leu Met Val Gly Asn Leu Ile Val Leu Pro
            100                 105                 110

Val Gly Ile Thr Phe Phe Lys Glu Glu Asn Ser Pro Pro Trp Ile Val
        115                 120                 125

Phe Asn Val Leu Ser Asp Thr Phe Phe Leu Leu Asp Leu Val Leu Asn
    130                 135                 140

Phe Arg Thr Gly Ile Val Val Glu Glu Gly Ala Glu Ile Leu Leu Ala
```

```
145                 150                 155                 160

Pro Arg Ala Ile Arg Thr Arg Tyr Leu Arg Thr Trp Phe Leu Val Asp
                165                 170                 175

Leu Ile Ser Ser Ile Pro Val Asp Tyr Ile Phe Leu Val Val Glu Leu
            180                 185                 190

Glu Pro Arg Leu Asp Ala Glu Val Tyr Lys Thr Ala Arg Ala Leu Arg
        195                 200                 205

Ile Val Arg Phe Thr Lys Ile Leu Ser Leu Leu Arg Leu Leu Arg Leu
    210                 215                 220

Ser Arg Leu Ile Arg Tyr Ile His Gln Trp Glu Glu Ile Phe His Met
225                 230                 235                 240

Thr Tyr Asp Leu Ala Ser Ala Val Val Arg Ile Phe Asn Leu Ile Gly
                245                 250                 255

Met Met Leu Leu Leu Cys His Trp Asp Gly Cys Leu Gln Phe Leu Val
            260                 265                 270

Pro Met Leu Gln Asp Phe Pro Pro Asp Cys Trp Val Ser Ile Asn His
        275                 280                 285

Met Val Asn His Ser Trp Gly Arg Gln Tyr Ser His Ala Leu Phe Lys
    290                 295                 300

Ala Met Ser His Met Leu Cys Ile Gly Tyr Gly Gln Gln Ala Pro Val
305                 310                 315                 320

Gly Met Pro Asp Val Trp Leu Thr Met Leu Ser Met Ile Val Gly Ala
                325                 330                 335

Thr Cys Tyr Ala Met Phe Ile Gly His Ala Thr Ala Leu Ile Gln Ser
            340                 345                 350

Leu Asp Ser Ser Arg Arg Gln Tyr Gln Glu Lys Tyr Lys Gln Val Glu
        355                 360                 365

Gln Tyr Met Ser Phe His Lys Leu Pro Ala Asp Thr Arg Gln Arg Ile
    370                 375                 380

His Glu Tyr Tyr Glu His Arg Tyr Gln Gly Lys Met Phe Asp Glu Glu
385                 390                 395                 400

Ser Ile Leu Gly Glu Leu Ser Glu Pro Leu Arg Glu Glu Ile Ile Asn
                405                 410                 415

Phe Thr Cys Arg Gly Leu Val Ala His Met Pro Leu Phe Ala His Ala
            420                 425                 430

Asp Pro Ser Phe Val Thr Ala Val Leu Thr Lys Leu Arg Phe Glu Val
        435                 440                 445

Phe Gln Pro Gly Asp Leu Val Val Arg Glu Gly Ser Val Gly Arg Lys
    450                 455                 460

Met Tyr Phe Ile Gln His Gly Leu Leu Ser Val Leu Ala Arg Gly Ala
465                 470                 475                 480

Arg Asp Thr Arg Leu Thr Asp Gly Ser Tyr Phe Gly Glu Ile Cys Leu
                485                 490                 495

Leu Thr Arg Gly Arg Arg Thr Ala Ser Val Arg Ala Asp Thr Tyr Cys
            500                 505                 510

Arg Leu Tyr Ser Leu Ser Val Asp His Phe Asn Ala Val Leu Glu Glu
        515                 520                 525

Phe Pro Met Met Arg Arg Ala Phe Glu Thr Val Ala Met Asp Arg Leu
    530                 535                 540

Leu Arg Ile Gly Lys Lys Asn Ser Ile Leu Gln Arg Lys Arg Ser Glu
545                 550                 555                 560

Pro Ser Pro Gly Ser Ser Gly Gly Ile Met Glu Gln His Leu Val Gln
                565                 570                 575
```

```
His Asp Arg Asp Met Ala Arg Gly Val Arg Gly Arg Ala Pro Ser Thr
            580                 585                 590

Gly Ala Gln Leu Ser Gly Lys Pro Val Leu Trp Glu Pro Leu Val His
        595                 600                 605

Ala Pro Leu Gln Ala Ala Ala Val Thr Ser Asn Val Ala Ile Ala Leu
    610                 615                 620

Thr His Gln Arg Gly Pro Leu Pro Leu Ser Pro Asp Ser Pro Ala Thr
625                 630                 635                 640

Leu Leu Ala Arg Ser Ala Trp Arg Ser Ala Gly Ser Pro Ala Ser Pro
                645                 650                 655

Leu Val Pro Val Arg Ala Gly Pro Trp Ala Ser Thr Ser Arg Leu Pro
            660                 665                 670

Ala Pro Pro Ala Arg Thr Leu His Ala Ser Leu Ser Arg Ala Gly Arg
        675                 680                 685

Ser Gln Val Ser Leu Leu Gly Pro Pro Pro Gly Gly Gly Gly Arg Arg
    690                 695                 700

Leu Gly Pro Arg Gly Arg Pro Leu Ser Ala Ser Gln Pro Ser Leu Pro
705                 710                 715                 720

Gln Arg Ala Thr Gly Asp Gly Ser Pro Gly Arg Lys Gly Ser Gly Ser
                725                 730                 735

Glu Arg Leu Pro Pro Ser Gly Leu Leu Ala Lys Pro Pro Arg Thr Ala
            740                 745                 750

Gln Pro Pro Arg Pro Pro Val Pro Glu Pro Ala Thr Pro Arg Gly Leu
        755                 760                 765

Gln Leu Ser Ala Asn Met
    770

<210> SEQ ID NO 5
<211> LENGTH: 2592
<212> TYPE: DNA
<213> ORGANISM: Mus musculus

<400> SEQUENCE: 5

atggatgcgc gcgggggcgg cgggcggccg ggcgatagtc cgggcacgac ccctgcgccg      60

gggccgccgc caccgccgcc gccgcccgcg ccccctcagc ctcagccacc acccgcgcca     120

cccccgaacc ccacgacccc ctcgcacccg gagtcggcgg acgagcccgg cccgcgcgcc     180

cggctctgca gccgcgacag cgcctgcacc cctggcgcgg ccaagggcgg cgcgaatggc     240

gagtgcgggc gcggggagcc gcagtgcagc cccgagggcc ccgcgcgcgg ccccaaggtt     300

tcgttctcat gccgcggggc ggcctccggg ccctcggcgg ccgaggaggc gggcagcgag     360

gaggcgggcc cggcgggtga gccgcgcggc agccaggcta gcttcctgca gcgccaattc     420

ggggcgcttc tgcagcccgg cgtcaacaag ttctccctgc ggatgttcgg cagccagaag     480

gccgtggagc gcgagcagga acgcgtgaag tcggcggggg cctggatcat ccacccctac     540

agcgacttca ggttttattg ggattaatc atgcttataa tgatggttgg aaatttggtc     600

atcataccag ttggaatcac gttcttcaca gagcagacga caacaccgtg gattattttc     660

aacgtggcat ccgatactgt tttcctgttg gacttaatca tgaattttag gactgggact     720

gtcaatgaag acagctcgga aatcatcctg gaccctaaag tgatcaagat gaattattta     780

aaaagctggt ttgtggtgga cttcatctca tcgatcccgg tggattatat ctttctcatt     840

gtagagaaag ggatggactc agaagtttac aagacagcca gagcacttcg tatcgtgagg     900

tttacaaaaa ttctcagtct cttgcggtta ttacgccttt caaggttaat cagatacata     960

caccagtggg aagagatatt ccacatgacc tatgacctcg ccagtgctgt ggtgaggatc    1020
```

```
ttcaacctca ttggcatgat gctgcttctg tgccactggg atggctgtct tcagttcctg   1080

gttcccctgc tgcaggactt cccaccagat tgctgggttt ctctgaatga aatggttaat   1140

gattcctggg gaaaacaata ttcctacgca ctcttcaaag ctatgagtca catgctgtgc   1200

attggttatg gcgcccaagc cctgtcagc atgtctgacc tctggattac catgctgagc   1260

atgattgtgg gcgccacctg ctacgcaatg tttgttggcc atgccacagc tttgatccag   1320

tctttggatt cgtcacggcg ccaataccag gagaagtaca agcaagtaga gcaatacatg   1380

tccttccaca aactgcccgc tgacttccgc cagaagatcc acgattacta tgaacaccgg   1440

taccaaggga agatgtttga tgaggacagc atccttgggg aactcaacgg gccactgcgt   1500

gaggagattg tgaacttcaa ctgccggaag ctggtggctt ccatgccgct gtttgccaat   1560

gcagacccca acttcgtcac agccatgctg acaaagctca aatttgaggt cttccagcct   1620

ggagattaca tcatccgaga ggggaccatc gggaagaaga tgtacttcat ccagcatggg   1680

gtggtgagcg tgctcaccaa gggcaacaag gagatgaagc tgtcggatgg ctcctatttc   1740

ggggagatct gcttgctcac gaggggccgg cgtacggcca gcgtgcgagc tgacacctac   1800

tgtcgcctct actcactgag tgtggacaat ttcaacgaag tactggagga ataccccatg   1860

atgcggcgtg cctttgagac tgtggctatt gaccggctag atcgcatagg caagaagaac   1920

tccatcttgc tgcacaaggt tcagcatgat ctcagctcag gtgtgttcaa caaccaggag   1980

aatgccatca tccaggagat tgtcaaatat gaccgtgaga tggtgcagca ggcagagctt   2040

ggacagcgtg tggggctctt cccaccaccg ccaccaccgc aggtcacatc ggccattgcc   2100

accctacagc aggctgtggc catgagcttc tgcccgcagg tggcccgccc gctcgtgggg   2160

cccctggcgc taggctcccc acgcctagtg cgccgcgcgc ccccagggcc tctgcctcct   2220

gcagcctcgc cagggccacc cgcagcaagc cccccggctg caccctcgag ccctcgggca   2280

ccgcggacct caccctacgg tgtgcctggc tctccggcaa cgcgtgtggg gcccgcattg   2340

cccgcacgtc gcctgagccg cgcctcgcgc ccactgtccg cctcgcagcc ctcgctgccc   2400

catggcgtgc ccgcgcccag ccccgcggcc tctgcgcgcc cggccagcag ctccacgccg   2460

cgcctgggac ccgcacccac cgcccggacc gccgcgccca gtccggaccg cagggactca   2520

gcctcgccgg gcgctgccag tggcctcgac ccactggact ctgcgcgctc gcgcctctct   2580

tccaacttgt ga                                                       2592
```

<210> SEQ ID NO 6
<211> LENGTH: 863
<212> TYPE: PRT
<213> ORGANISM: Mus musculus

<400> SEQUENCE: 6

```
Met Asp Ala Arg Gly Gly Gly Gly Arg Pro Gly Asp Ser Pro Gly Thr
  1               5                  10                  15

Thr Pro Ala Pro Gly Pro Pro Pro Pro Pro Pro Pro Pro Ala Pro Pro
             20                  25                  30

Gln Pro Gln Pro Pro Pro Ala Pro Pro Pro Asn Pro Thr Thr Pro Ser
         35                  40                  45

His Pro Glu Ser Ala Asp Glu Pro Gly Pro Arg Ala Arg Leu Cys Ser
     50                  55                  60

Arg Asp Ser Ala Cys Thr Pro Gly Ala Ala Lys Gly Gly Ala Asn Gly
 65                  70                  75                  80

Glu Cys Gly Arg Gly Glu Pro Gln Cys Ser Pro Glu Gly Pro Ala Arg
                 85                  90                  95
```

```
Gly Pro Lys Val Ser Phe Ser Cys Arg Gly Ala Ala Ser Gly Pro Ser
            100                 105                 110

Ala Ala Glu Glu Ala Gly Ser Glu Glu Ala Gly Pro Ala Gly Glu Pro
        115                 120                 125

Arg Gly Ser Gln Ala Ser Phe Leu Gln Arg Gln Phe Gly Ala Leu Leu
    130                 135                 140

Gln Pro Gly Val Asn Lys Phe Ser Leu Arg Met Phe Gly Ser Gln Lys
145                 150                 155                 160

Ala Val Glu Arg Glu Gln Glu Arg Val Lys Ser Ala Gly Ala Trp Ile
                165                 170                 175

Ile His Pro Tyr Ser Asp Phe Arg Phe Tyr Trp Gly Leu Ile Met Leu
            180                 185                 190

Ile Met Met Val Gly Asn Leu Val Ile Ile Pro Val Gly Ile Thr Phe
        195                 200                 205

Phe Thr Glu Gln Thr Thr Thr Pro Trp Ile Ile Phe Asn Val Ala Ser
    210                 215                 220

Asp Thr Val Phe Leu Leu Asp Leu Ile Met Asn Phe Arg Thr Gly Thr
225                 230                 235                 240

Val Asn Glu Asp Ser Ser Glu Ile Ile Leu Asp Pro Lys Val Ile Lys
                245                 250                 255

Met Asn Tyr Leu Lys Ser Trp Phe Val Val Asp Phe Ile Ser Ser Ile
            260                 265                 270

Pro Val Asp Tyr Ile Phe Leu Ile Val Glu Lys Gly Met Asp Ser Glu
        275                 280                 285

Val Tyr Lys Thr Ala Arg Ala Leu Arg Ile Val Arg Phe Thr Lys Ile
    290                 295                 300

Leu Ser Leu Leu Arg Leu Leu Arg Leu Ser Arg Leu Ile Arg Tyr Ile
305                 310                 315                 320

His Gln Trp Glu Glu Ile Phe His Met Thr Tyr Asp Leu Ala Ser Ala
                325                 330                 335

Val Val Arg Ile Phe Asn Leu Ile Gly Met Met Leu Leu Leu Cys His
            340                 345                 350

Trp Asp Gly Cys Leu Gln Phe Leu Val Pro Leu Leu Gln Asp Phe Pro
        355                 360                 365

Pro Asp Cys Trp Val Ser Leu Asn Glu Met Val Asn Asp Ser Trp Gly
    370                 375                 380

Lys Gln Tyr Ser Tyr Ala Leu Phe Lys Ala Met Ser His Met Leu Cys
385                 390                 395                 400

Ile Gly Tyr Gly Ala Gln Ala Pro Val Ser Met Ser Asp Leu Trp Ile
                405                 410                 415

Thr Met Leu Ser Met Ile Val Gly Ala Thr Cys Tyr Ala Met Phe Val
            420                 425                 430

Gly His Ala Thr Ala Leu Ile Gln Ser Leu Asp Ser Ser Arg Arg Gln
        435                 440                 445

Tyr Gln Glu Lys Tyr Lys Gln Val Glu Gln Tyr Met Ser Phe His Lys
    450                 455                 460

Leu Pro Ala Asp Phe Arg Gln Lys Ile His Asp Tyr Tyr Glu His Arg
465                 470                 475                 480

Tyr Gln Gly Lys Met Phe Asp Glu Asp Ser Ile Leu Gly Glu Leu Asn
                485                 490                 495

Gly Pro Leu Arg Glu Glu Ile Val Asn Phe Asn Cys Arg Lys Leu Val
            500                 505                 510

Ala Ser Met Pro Leu Phe Ala Asn Ala Asp Pro Asn Phe Val Thr Ala
```

```
        515                 520                 525

Met Leu Thr Lys Leu Lys Phe Glu Val Phe Gln Pro Gly Asp Tyr Ile
    530                 535                 540

Ile Arg Glu Gly Thr Ile Gly Lys Lys Met Tyr Phe Ile Gln His Gly
545                 550                 555                 560

Val Val Ser Val Leu Thr Lys Gly Asn Lys Glu Met Lys Leu Ser Asp
                565                 570                 575

Gly Ser Tyr Phe Gly Glu Ile Cys Leu Leu Thr Arg Gly Arg Arg Thr
            580                 585                 590

Ala Ser Val Arg Ala Asp Thr Tyr Cys Arg Leu Tyr Ser Leu Ser Val
        595                 600                 605

Asp Asn Phe Asn Glu Val Leu Glu Glu Tyr Pro Met Met Arg Arg Ala
    610                 615                 620

Phe Glu Thr Val Ala Ile Asp Arg Leu Asp Arg Ile Gly Lys Lys Asn
625                 630                 635                 640

Ser Ile Leu Leu His Lys Val Gln His Asp Leu Ser Ser Gly Val Phe
                645                 650                 655

Asn Asn Gln Glu Asn Ala Ile Ile Gln Glu Ile Val Lys Tyr Asp Arg
            660                 665                 670

Glu Met Val Gln Gln Ala Glu Leu Gly Gln Arg Val Gly Leu Phe Pro
        675                 680                 685

Pro Pro Pro Pro Pro Gln Val Thr Ser Ala Ile Ala Thr Leu Gln Gln
    690                 695                 700

Ala Val Ala Met Ser Phe Cys Pro Gln Val Ala Arg Pro Leu Val Gly
705                 710                 715                 720

Pro Leu Ala Leu Gly Ser Pro Arg Leu Val Arg Arg Ala Pro Pro Gly
                725                 730                 735

Pro Leu Pro Pro Ala Ala Ser Pro Gly Pro Pro Ala Ala Ser Pro Pro
            740                 745                 750

Ala Ala Pro Ser Ser Pro Arg Ala Pro Arg Thr Ser Pro Tyr Gly Val
        755                 760                 765

Pro Gly Ser Pro Ala Thr Arg Val Gly Pro Ala Leu Pro Ala Arg Arg
    770                 775                 780

Leu Ser Arg Ala Ser Arg Pro Leu Ser Ala Ser Gln Pro Ser Leu Pro
785                 790                 795                 800

His Gly Val Pro Ala Pro Ser Pro Ala Ala Ser Ala Arg Pro Ala Ser
                805                 810                 815

Ser Ser Thr Pro Arg Leu Gly Pro Ala Pro Thr Ala Arg Thr Ala Ala
            820                 825                 830

Pro Ser Pro Asp Arg Arg Asp Ser Ala Ser Pro Gly Ala Ala Ser Gly
        835                 840                 845

Leu Asp Pro Leu Asp Ser Ala Arg Ser Arg Leu Ser Ser Asn Leu
    850                 855                 860


<210> SEQ ID NO 7
<211> LENGTH: 2340
<212> TYPE: DNA
<213> ORGANISM: Mus musculus

<400> SEQUENCE: 7

atggaggagg aggcgcggcc ggcggcgggg gccggcgaag cggcgacccc tgcacgcgag      60

acgcctcctg cggctccggc ccaggcccgc gcggcctcag gtggggtgcc ggagtctgcg     120

cccgagccga agaggcggca gctcgggacg ctgctgcagc cgacggtcaa caagttctct     180

ctccgggtct tcggcagcca caaagcagta gaaatcgagc aggagagggt gaagtccgcc     240
```

```
ggggcctgga tcatccaccc ctacagcgac ttccggtttt actgggatct catcatgctg     300

ctgctgatgg tggggaacct catagttctg cctgtgggta tcactttctt caaggaggag     360

aactctccac cctggatcgt cttcaatgtc ctctctgaca ctttcttcct gctggatctg     420

gtgctcaact tccgaactgg catcgtggtg gaggaaggtg ccgagatcct gctggcgcca     480

agggccatcc gaacgcgtta cctgcgcacc tggttcctgg ttgatctgat ctcctccatc     540

cctgtggatt atatcttcct agtggtggag ctggagccac gactagatgc tgaggtctac     600

aaaacggcac gggccctgcg catcgttaga ttcaccaaga tccttagcct gctgcggctg     660

ctccgcctct cccgcctcat ccgctacata caccagtggg aggagatctt tcacatgacc     720

tacgacctgg ccagtgcagt ggttcgcatc ttcaacctca ttggaatgat gttgctgctg     780

tgtcactggg acggctgtct gcagtttctg gtccctatgc tgcaggactt cccgtccgac     840

tgctgggtct ccatgaaccg catggtgaac cactcgtggg gccgccagta ttcccacgcc     900

ctgttcaagg ccatgagtca catgctatgc attggctatg ggcagcaggc accggtaggc     960

atgcctgacg tctggctcac catgctcagt atgattgtgg gcgccacgtg ttatgccatg    1020

ttcatcggtc acgccaccgc cctcatccag tccctggact cttcccggcg acagtaccag    1080

gagaagtaca agcaggtgga gcagtacatg tccttccaca agctgcccgc tgacacccgg    1140

cagcgcatcc acgagtacta cgagcatcgc taccagggca agatgtttga tgaagagagc    1200

atcctggggg agctgagcga gccacttcgg gaggagatta ttaacttcac ctgccggggc    1260

ctggtggccc acatgccgct gtttgctcat gctgacccca gcttcgtcac cgcagtgctc    1320

accaagctcc gttttgaggt cttccaacca ggggacctgg tggtgcgtga gggctccgtg    1380

ggcaggaaga tgtacttcat ccagcacggg ctgctgagtg tgctggcacg tggcgcccgc    1440

gacacccgcc tcactgatgg atcctacttt ggggagatct gcctgctgac tcgaggtcgg    1500

agaacagcca gtgtaagggc tgacacctat tgtcgcctct actcgctcag cgtggaccac    1560

ttcaatgcgg tgcttgagga gttcccaatg atgcgcaggg cttttgagac ggtggccatg    1620

gaccggcttc ggcgcatcgg caaaaagaat tcgatactgc agcggaaacg ctctgagccg    1680

agtccaggca gcagcggtgg cgtcatggag cagcatttgg tacaacacga cagagacatg    1740

gctcgtggtg ttcggggcct ggctcctggt acaggagctc gactcagtgg aaagccagtg    1800

ctgtgggaac cactggtgca cgcccctctg caggcagctg ctgtgacctc caacgtggcc    1860

atagccttga ctcaccagcg aggccctctg cccctctccc ctgattctcc agccaccctc    1920

ctagctcgat ctgctagacg ctcagcaggc tccccagcct ccccactggt gcctgtccga    1980

gcaggtcctc tgctggcccg gggaccctgg gcgtccactt ctcgcctgcc tgctccacct    2040

gcccgaaccc tccatgccag cctatcccgg acagggcgtt cccaggtatc tctgttgggc    2100

cctcccccag gaggaggtgc tcggaggcta ggacctcggg gccgcccact ttctgcctcg    2160

caaccctctc tgcctcagcg agcaacaggg gatggctctc ctaggcgtaa aggctctgga    2220

agtgagcgcc tgccccccctc tgggctcttg gccaaacctc cagggacagt ccagccaccc    2280

aggtcatcag tgcctgagcc agttaccccc agaggtcccc aaatttctgc caacatgtga    2340
```

<210> SEQ ID NO 8
<211> LENGTH: 779
<212> TYPE: PRT
<213> ORGANISM: Mus musculus

<400> SEQUENCE: 8

Met Glu Glu Glu Ala Arg Pro Ala Ala Gly Ala Gly Glu Ala Ala Thr

-continued

```
1               5                   10                  15

Pro Ala Arg Glu Thr Pro Pro Ala Ala Pro Ala Gln Ala Arg Ala Ala
            20                  25                  30

Ser Gly Gly Val Pro Glu Ser Ala Pro Glu Pro Lys Arg Arg Gln Leu
        35                  40                  45

Gly Thr Leu Leu Gln Pro Thr Val Asn Lys Phe Ser Leu Arg Val Phe
    50                  55                  60

Gly Ser His Lys Ala Val Glu Ile Glu Gln Glu Arg Val Lys Ser Ala
65                  70                  75                  80

Gly Ala Trp Ile Ile His Pro Tyr Ser Asp Phe Arg Phe Tyr Trp Asp
                85                  90                  95

Leu Ile Met Leu Leu Leu Met Val Gly Asn Leu Ile Val Leu Pro Val
            100                 105                 110

Gly Ile Thr Phe Phe Lys Glu Glu Asn Ser Pro Pro Trp Ile Val Phe
        115                 120                 125

Asn Val Leu Ser Asp Thr Phe Phe Leu Leu Asp Leu Val Leu Asn Phe
    130                 135                 140

Arg Thr Gly Ile Val Val Glu Glu Gly Ala Glu Ile Leu Leu Ala Pro
145                 150                 155                 160

Arg Ala Ile Arg Thr Arg Tyr Leu Arg Thr Trp Phe Leu Val Asp Leu
                165                 170                 175

Ile Ser Ser Ile Pro Val Asp Tyr Ile Phe Leu Val Val Glu Leu Glu
            180                 185                 190

Pro Arg Leu Asp Ala Glu Val Tyr Lys Thr Ala Arg Ala Leu Arg Ile
        195                 200                 205

Val Arg Phe Thr Lys Ile Leu Ser Leu Leu Arg Leu Leu Arg Leu Ser
    210                 215                 220

Arg Leu Ile Arg Tyr Ile His Gln Trp Glu Glu Ile Phe His Met Thr
225                 230                 235                 240

Tyr Asp Leu Ala Ser Ala Val Val Arg Ile Phe Asn Leu Ile Gly Met
                245                 250                 255

Met Leu Leu Leu Cys His Trp Asp Gly Cys Leu Gln Phe Leu Val Pro
            260                 265                 270

Met Leu Gln Asp Phe Pro Ser Asp Cys Trp Val Ser Met Asn Arg Met
        275                 280                 285

Val Asn His Ser Trp Gly Arg Gln Tyr Ser His Ala Leu Phe Lys Ala
    290                 295                 300

Met Ser His Met Leu Cys Ile Gly Tyr Gly Gln Gln Ala Pro Val Gly
305                 310                 315                 320

Met Pro Asp Val Trp Leu Thr Met Leu Ser Met Ile Val Gly Ala Thr
                325                 330                 335

Cys Tyr Ala Met Phe Ile Gly His Ala Thr Ala Leu Ile Gln Ser Leu
            340                 345                 350

Asp Ser Ser Arg Arg Gln Tyr Gln Glu Lys Tyr Lys Gln Val Glu Gln
        355                 360                 365

Tyr Met Ser Phe His Lys Leu Pro Ala Asp Thr Arg Gln Arg Ile His
    370                 375                 380

Glu Tyr Tyr Glu His Arg Tyr Gln Gly Lys Met Phe Asp Glu Glu Ser
385                 390                 395                 400

Ile Leu Gly Glu Leu Ser Glu Pro Leu Arg Glu Glu Ile Ile Asn Phe
                405                 410                 415

Thr Cys Arg Gly Leu Val Ala His Met Pro Leu Phe Ala His Ala Asp
            420                 425                 430
```

```
Pro Ser Phe Val Thr Ala Val Leu Thr Lys Leu Arg Phe Glu Val Phe
        435                 440                 445

Gln Pro Gly Asp Leu Val Val Arg Glu Gly Ser Val Gly Arg Lys Met
    450                 455                 460

Tyr Phe Ile Gln His Gly Leu Leu Ser Val Leu Ala Arg Gly Ala Arg
465                 470                 475                 480

Asp Thr Arg Leu Thr Asp Gly Ser Tyr Phe Gly Glu Ile Cys Leu Leu
                485                 490                 495

Thr Arg Gly Arg Arg Thr Ala Ser Val Arg Ala Asp Thr Tyr Cys Arg
            500                 505                 510

Leu Tyr Ser Leu Ser Val Asp His Phe Asn Ala Val Leu Glu Glu Phe
        515                 520                 525

Pro Met Met Arg Arg Ala Phe Glu Thr Val Ala Met Asp Arg Leu Arg
    530                 535                 540

Arg Ile Gly Lys Lys Asn Ser Ile Leu Gln Arg Lys Arg Ser Glu Pro
545                 550                 555                 560

Ser Pro Gly Ser Ser Gly Gly Val Met Glu Gln His Leu Val Gln His
                565                 570                 575

Asp Arg Asp Met Ala Arg Gly Val Arg Gly Leu Ala Pro Gly Thr Gly
            580                 585                 590

Ala Arg Leu Ser Gly Lys Pro Val Leu Trp Glu Pro Leu Val His Ala
        595                 600                 605

Pro Leu Gln Ala Ala Ala Val Thr Ser Asn Val Ala Ile Ala Leu Thr
    610                 615                 620

His Gln Arg Gly Pro Leu Pro Leu Ser Pro Asp Ser Pro Ala Thr Leu
625                 630                 635                 640

Leu Ala Arg Ser Ala Arg Arg Ser Ala Gly Ser Pro Ala Ser Pro Leu
                645                 650                 655

Val Pro Val Arg Ala Gly Pro Leu Leu Ala Arg Gly Pro Trp Ala Ser
            660                 665                 670

Thr Ser Arg Leu Pro Ala Pro Pro Ala Arg Thr Leu His Ala Ser Leu
        675                 680                 685

Ser Arg Thr Gly Arg Ser Gln Val Ser Leu Leu Gly Pro Pro Pro Gly
    690                 695                 700

Gly Gly Ala Arg Arg Leu Gly Pro Arg Gly Arg Pro Leu Ser Ala Ser
705                 710                 715                 720

Gln Pro Ser Leu Pro Gln Arg Ala Thr Gly Asp Gly Ser Pro Arg Arg
                725                 730                 735

Lys Gly Ser Gly Ser Glu Arg Leu Pro Pro Ser Gly Leu Leu Ala Lys
            740                 745                 750

Pro Pro Gly Thr Val Gln Pro Pro Arg Ser Ser Val Pro Glu Pro Val
        755                 760                 765

Thr Pro Arg Gly Pro Gln Ile Ser Ala Asn Met
    770                 775


<210> SEQ ID NO 9
<211> LENGTH: 910
<212> TYPE: PRT
<213> ORGANISM: Mus musculus

<400> SEQUENCE: 9

Met Glu Gly Gly Gly Lys Pro Asn Ser Ala Ser Asn Ser Arg Asp Asp
  1               5                  10                  15

Gly Asn Ser Val Phe Pro Ser Lys Ala Pro Ala Thr Gly Pro Val Ala
             20                  25                  30
```

```
Ala Asp Lys Arg Leu Gly Thr Pro Pro Arg Gly Gly Ala Ala Gly Lys
         35                  40                  45

Glu His Gly Asn Ser Val Cys Phe Lys Val Asp Gly Gly Gly Gly Glu
     50                  55                  60

Glu Pro Ala Gly Ser Phe Glu Asp Ala Glu Gly Pro Arg Arg Gln Tyr
 65                  70                  75                  80

Gly Phe Met Gln Arg Gln Phe Thr Ser Met Leu Gln Pro Gly Val Asn
                 85                  90                  95

Lys Phe Ser Leu Arg Met Phe Gly Ser Gln Lys Ala Val Glu Lys Glu
            100                 105                 110

Gln Glu Arg Val Lys Thr Ala Gly Phe Trp Ile Ile His Pro Tyr Ser
        115                 120                 125

Asp Phe Arg Phe Tyr Trp Asp Leu Ile Met Leu Ile Met Met Val Gly
    130                 135                 140

Asn Leu Val Ile Ile Pro Val Gly Ile Thr Phe Phe Thr Glu Gln Thr
145                 150                 155                 160

Thr Thr Pro Trp Ile Ile Phe Asn Val Ala Ser Asp Thr Val Phe Leu
                165                 170                 175

Leu Asp Leu Ile Met Asn Phe Arg Thr Gly Thr Val Asn Glu Asp Ser
            180                 185                 190

Ser Glu Ile Ile Leu Asp Pro Lys Val Ile Lys Met Asn Tyr Leu Lys
        195                 200                 205

Ser Trp Phe Val Val Asp Phe Ile Ser Ser Ile Pro Val Asp Tyr Ile
    210                 215                 220

Phe Leu Ile Val Glu Lys Gly Met Asp Ser Glu Val Tyr Lys Thr Ala
225                 230                 235                 240

Arg Ala Leu Arg Ile Val Arg Phe Thr Lys Ile Leu Ser Leu Leu Arg
                245                 250                 255

Leu Leu Arg Leu Ser Arg Leu Ile Arg Tyr Ile His Gln Trp Glu Glu
            260                 265                 270

Ile Phe His Met Thr Tyr Asp Leu Ala Ser Ala Val Val Arg Ile Phe
        275                 280                 285

Asn Leu Ile Gly Met Met Leu Leu Leu Cys His Trp Asp Gly Cys Leu
    290                 295                 300

Gln Phe Leu Val Pro Leu Leu Gln Asp Phe Pro Pro Asp Cys Trp Val
305                 310                 315                 320

Ser Leu Asn Glu Met Val Asn Asp Ser Trp Gly Lys Gln Tyr Ser Tyr
                325                 330                 335

Ala Leu Phe Lys Ala Met Ser His Met Leu Cys Ile Gly Tyr Gly Ala
            340                 345                 350

Gln Ala Pro Val Ser Met Ser Asp Leu Trp Ile Thr Met Leu Ser Met
        355                 360                 365

Ile Val Gly Ala Thr Cys Tyr Ala Met Phe Val Gly His Ala Thr Ala
    370                 375                 380

Leu Ile Gln Ser Leu Asp Ser Ser Arg Arg Gln Tyr Gln Glu Lys Tyr
385                 390                 395                 400

Lys Gln Val Glu Gln Tyr Met Ser Phe His Lys Leu Pro Ala Asp Met
                405                 410                 415

Arg Gln Lys Ile His Asp Tyr Tyr Glu His Arg Tyr Gln Gly Lys Ile
            420                 425                 430

Phe Asp Glu Glu Asn Ile Leu Ser Glu Leu Asn Asp Pro Leu Arg Glu
        435                 440                 445

Glu Ile Val Asn Phe Asn Cys Arg Lys Leu Val Ala Thr Met Pro Leu
    450                 455                 460
```

```
Phe Ala Asn Ala Asp Pro Asn Phe Val Thr Ala Met Leu Ser Lys Leu
465                 470                 475                 480

Arg Phe Glu Val Phe Gln Pro Gly Asp Tyr Ile Ile Arg Glu Gly Ala
                485                 490                 495

Val Gly Lys Lys Met Tyr Phe Ile Gln His Gly Val Ala Gly Val Ile
            500                 505                 510

Thr Lys Ser Ser Lys Glu Met Lys Leu Thr Asp Gly Ser Tyr Phe Gly
        515                 520                 525

Glu Ile Cys Leu Leu Thr Lys Gly Arg Arg Thr Ala Ser Val Arg Ala
    530                 535                 540

Asp Thr Tyr Cys Arg Leu Tyr Ser Leu Ser Val Asp Asn Phe Asn Glu
545                 550                 555                 560

Val Leu Glu Glu Tyr Pro Met Met Arg Arg Ala Phe Glu Thr Val Ala
                565                 570                 575

Ile Asp Arg Leu Asp Arg Ile Gly Lys Lys Asn Ser Ile Leu Leu Gln
            580                 585                 590

Lys Phe Gln Lys Asp Leu Asn Thr Gly Val Phe Asn Asn Gln Glu Asn
        595                 600                 605

Glu Ile Leu Lys Gln Ile Val Lys His Asp Arg Glu Met Val Gln Ala
    610                 615                 620

Ile Pro Pro Ile Asn Tyr Pro Gln Met Thr Ala Leu Asn Cys Thr Ser
625                 630                 635                 640

Ser Thr Thr Thr Pro Thr Ser Arg Met Arg Thr Gln Ser Pro Pro Val
                645                 650                 655

Tyr Thr Ala Thr Ser Leu Ser His Ser Asn Leu His Ser Pro Ser Pro
            660                 665                 670

Ser Thr Gln Thr Pro Gln Pro Ser Ala Ile Leu Ser Pro Cys Ser Tyr
        675                 680                 685

Thr Thr Ala Val Cys Ser Pro Pro Ile Gln Ser Pro Leu Ala Thr Arg
    690                 695                 700

Thr Phe His Tyr Ala Ser Pro Thr Ala Ser Gln Leu Ser Leu Met Gln
705                 710                 715                 720

Gln Pro Gln Gln Gln Leu Pro Gln Ser Gln Val Gln Gln Thr Gln Thr
                725                 730                 735

Gln Thr Gln Gln Gln Gln Gln Gln Gln Gln Gln Gln Gln Gln Gln Gln
            740                 745                 750

Gln Gln Gln Gln Gln Gln Gln Gln Gln Gln Gln Gln Gln Gln Gln Gln
        755                 760                 765

Gln Gln Gln Gln Gln Gln Gln Pro Gln Thr Pro Gly Ser Ser Thr Pro
    770                 775                 780

Lys Asn Glu Val His Lys Ser Thr Gln Ala Leu His Asn Thr Asn Leu
785                 790                 795                 800

Thr Lys Glu Val Arg Pro Leu Ser Ala Ser Gln Pro Ser Leu Pro His
                805                 810                 815

Glu Val Ser Thr Leu Ile Ser Arg Pro His Pro Thr Val Gly Glu Ser
            820                 825                 830

Leu Ala Ser Ile Pro Gln Pro Val Ala Ala Val His Ser Thr Gly Leu
        835                 840                 845

Gln Ala Gly Ser Arg Ser Thr Val Pro Gln Arg Val Thr Leu Phe Arg
    850                 855                 860

Gln Met Ser Ser Gly Ala Ile Pro Pro Asn Arg Gly Val Pro Pro Ala
865                 870                 875                 880

Pro Pro Pro Pro Ala Ala Val Gln Arg Glu Ser Pro Ser Val Leu Asn
```

```
                885                 890                 895

Thr Asp Pro Asp Ala Glu Lys Pro Arg Phe Ala Ser Asn Leu
            900                 905                 910


<210> SEQ ID NO 10
<211> LENGTH: 910
<212> TYPE: PRT
<213> ORGANISM: Rattus norvegicus

<400> SEQUENCE: 10

Met Glu Gly Gly Gly Lys Pro Asn Ser Ala Ser Asn Ser Arg Asp Asp
  1               5                  10                  15

Gly Asn Ser Val Tyr Pro Ser Lys Ala Pro Ala Thr Gly Pro Ala Ala
             20                  25                  30

Ala Asp Lys Arg Leu Gly Thr Pro Pro Gly Gly Gly Ala Ala Gly Lys
         35                  40                  45

Glu His Gly Asn Ser Val Cys Phe Lys Val Asp Gly Gly Gly Gly Glu
     50                  55                  60

Glu Pro Ala Gly Ser Phe Glu Asp Ala Glu Gly Pro Arg Arg Gln Tyr
 65                  70                  75                  80

Gly Phe Met Gln Arg Gln Phe Thr Ser Met Leu Gln Pro Gly Val Asn
                 85                  90                  95

Lys Phe Ser Leu Arg Met Phe Gly Ser Gln Lys Ala Val Glu Lys Glu
            100                 105                 110

Gln Glu Arg Val Lys Thr Ala Gly Phe Trp Ile Ile His Pro Tyr Ser
        115                 120                 125

Asp Phe Arg Phe Tyr Trp Asp Leu Ile Met Leu Ile Met Met Val Gly
    130                 135                 140

Asn Leu Val Ile Ile Pro Val Gly Ile Thr Phe Phe Thr Glu Gln Thr
145                 150                 155                 160

Thr Thr Pro Trp Ile Ile Phe Asn Val Ala Ser Asp Thr Val Phe Leu
                165                 170                 175

Leu Asp Leu Ile Met Asn Phe Arg Thr Gly Thr Val Asn Glu Asp Ser
            180                 185                 190

Ser Glu Ile Ile Leu Asp Pro Lys Val Ile Lys Met Asn Tyr Leu Lys
        195                 200                 205

Ser Trp Phe Val Val Asp Phe Ile Ser Ser Ile Pro Val Asp Tyr Ile
    210                 215                 220

Phe Leu Ile Val Glu Lys Gly Met Asp Ser Glu Val Tyr Lys Thr Ala
225                 230                 235                 240

Arg Ala Leu Arg Ile Val Arg Phe Thr Lys Ile Leu Ser Leu Leu Arg
                245                 250                 255

Leu Leu Arg Leu Ser Arg Leu Ile Arg Tyr Ile His Gln Trp Glu Glu
            260                 265                 270

Ile Phe His Met Thr Tyr Asp Leu Ala Ser Ala Val Val Arg Ile Phe
        275                 280                 285

Asn Leu Ile Gly Met Met Leu Leu Leu Cys His Trp Asp Gly Cys Leu
    290                 295                 300

Gln Phe Leu Val Pro Leu Leu Gln Asp Phe Pro Pro Asp Cys Trp Val
305                 310                 315                 320

Ser Leu Asn Glu Met Val Asn Asp Ser Trp Gly Lys Gln Tyr Ser Tyr
                325                 330                 335

Ala Leu Phe Lys Ala Met Ser His Met Leu Cys Ile Gly Tyr Gly Ala
            340                 345                 350

Gln Ala Pro Val Ser Met Ser Asp Leu Trp Ile Thr Met Leu Ser Met
```

```
        355                 360                 365

Ile Val Gly Ala Thr Cys Tyr Ala Met Phe Val Gly His Ala Thr Ala
    370                 375                 380

Leu Ile Gln Ser Leu Asp Ser Ser Arg Arg Gln Tyr Gln Glu Lys Tyr
385                 390                 395                 400

Lys Gln Val Glu Gln Tyr Met Ser Phe His Lys Leu Pro Ala Asp Met
                405                 410                 415

Arg Gln Lys Ile His Asp Tyr Tyr Glu His Arg Tyr Gln Gly Lys Ile
            420                 425                 430

Phe Asp Glu Glu Asn Ile Leu Ser Glu Leu Asn Asp Pro Leu Arg Glu
        435                 440                 445

Glu Ile Val Asn Phe Asn Cys Arg Lys Leu Val Ala Thr Met Pro Leu
    450                 455                 460

Phe Ala Asn Ala Asp Pro Asn Phe Val Thr Ala Met Leu Ser Lys Leu
465                 470                 475                 480

Arg Phe Glu Val Phe Gln Pro Gly Asp Tyr Ile Ile Arg Glu Gly Ala
                485                 490                 495

Val Gly Lys Lys Met Tyr Phe Ile Gln His Gly Val Ala Gly Val Ile
            500                 505                 510

Thr Lys Ser Ser Lys Glu Met Lys Leu Thr Asp Gly Ser Tyr Phe Gly
        515                 520                 525

Glu Ile Cys Leu Leu Thr Lys Gly Arg Arg Thr Ala Ser Val Arg Ala
    530                 535                 540

Asp Thr Tyr Cys Arg Leu Tyr Ser Leu Ser Val Asp Asn Phe Asn Glu
545                 550                 555                 560

Val Leu Glu Glu Tyr Pro Met Met Arg Arg Ala Phe Glu Thr Val Ala
                565                 570                 575

Ile Asp Arg Leu Asp Arg Ile Gly Lys Lys Asn Ser Ile Leu Leu Gln
            580                 585                 590

Lys Phe Gln Lys Asp Leu Asn Thr Gly Val Phe Asn Asn Gln Glu Asn
        595                 600                 605

Glu Ile Leu Lys Gln Ile Val Lys His Asp Arg Glu Met Val Gln Ala
    610                 615                 620

Ile Pro Pro Ile Asn Tyr Pro Gln Met Thr Ala Leu Asn Cys Thr Ser
625                 630                 635                 640

Ser Thr Thr Thr Pro Thr Ser Arg Met Arg Thr Gln Ser Pro Pro Val
                645                 650                 655

Tyr Thr Ala Thr Ser Leu Ser His Ser Asn Leu His Ser Pro Ser Pro
            660                 665                 670

Ser Thr Gln Thr Pro Gln Pro Ser Ala Ile Leu Ser Pro Cys Ser Tyr
        675                 680                 685

Thr Thr Ala Val Cys Ser Pro Pro Ile Gln Ser Pro Leu Ala Thr Arg
    690                 695                 700

Thr Phe His Tyr Ala Ser Pro Thr Ala Ser Gln Leu Ser Leu Met Gln
705                 710                 715                 720

Gln Pro Gln Pro Gln Leu Gln Gln Ser Gln Val Gln Gln Thr Gln Thr
                725                 730                 735

Gln Thr Gln Gln Gln Gln Gln Gln Gln Pro Gln Pro Gln Pro Gln
            740                 745                 750

Gln Pro Gln Gln Gln Gln Gln Gln Gln Gln Gln Gln Gln Gln Gln Gln
        755                 760                 765

Gln Gln Gln Gln Gln Gln Gln Pro Gln Thr Pro Gly Ser Ser Thr Pro
    770                 775                 780
```

Lys Asn Glu Val His Lys Ser Thr Gln Ala Leu His Asn Thr His Leu
785 790 795 800

Thr Arg Glu Val Arg Pro Leu Ser Ala Ser Gln Pro Ser Leu Pro His
805 810 815

Glu Val Ser Thr Met Ile Ser Arg Pro His Pro Thr Val Gly Glu Ser
820 825 830

Leu Ala Ser Ile Pro Gln Pro Val Ala Thr Val His Ser Thr Gly Leu
835 840 845

Gln Ala Gly Ser Arg Ser Thr Val Pro Gln Arg Val Thr Leu Phe Arg
850 855 860

Gln Met Ser Ser Gly Ala Ile Pro Pro Asn Arg Gly Val Pro Pro Ala
865 870 875 880

Pro Pro Pro Pro Ala Ala Val Gln Arg Glu Ser Pro Ser Val Leu Asn
885 890 895

Lys Asp Pro Asp Ala Glu Lys Pro Arg Phe Ala Ser Asn Leu
900 905 910

<210> SEQ ID NO 11
<211> LENGTH: 890
<212> TYPE: PRT
<213> ORGANISM: Homo sapiens

<400> SEQUENCE: 11

Met Glu Gly Gly Gly Lys Pro Asn Ser Ser Ser Asn Ser Arg Asp Asp
1 5 10 15

Gly Asn Ser Val Phe Pro Ala Lys Ala Ser Ala Thr Gly Ala Gly Pro
20 25 30

Ala Ala Ala Glu Lys Arg Leu Gly Thr Pro Pro Gly Gly Gly Gly Ala
35 40 45

Gly Ala Lys Glu His Gly Asn Ser Val Cys Phe Lys Val Asp Gly Gly
50 55 60

Gly Gly Gly Gly Gly Gly Gly Gly Gly Gly Glu Glu Pro Ala Gly Gly
65 70 75 80

Phe Glu Asp Ala Glu Gly Pro Arg Arg Gln Tyr Gly Phe Met Gln Arg
85 90 95

Gln Phe Thr Ser Met Leu Gln Pro Gly Val Asn Lys Phe Ser Leu Arg
100 105 110

Met Phe Gly Ser Gln Lys Ala Val Glu Lys Glu Gln Glu Arg Val Lys
115 120 125

Thr Ala Gly Phe Trp Ile Ile His Pro Tyr Ser Asp Phe Arg Phe Tyr
130 135 140

Trp Asp Leu Ile Met Leu Ile Met Met Val Gly Asn Leu Val Ile Ile
145 150 155 160

Pro Val Gly Ile Thr Phe Phe Thr Glu Gln Thr Thr Thr Pro Trp Ile
165 170 175

Ile Phe Asn Val Ala Ser Asp Thr Val Phe Leu Leu Asp Leu Ile Met
180 185 190

Asn Phe Arg Thr Gly Thr Val Asn Glu Asp Ser Ser Glu Ile Ile Leu
195 200 205

Asp Pro Lys Val Ile Lys Met Asn Tyr Leu Lys Ser Trp Ser Val Val
210 215 220

Asp Phe Ile Ser Ser Ile Pro Val Asp Tyr Ile Phe Leu Ile Val Glu
225 230 235 240

Lys Gly Met Asp Ser Glu Val Tyr Lys Thr Ala Arg Ala Leu Arg Ile
245 250 255

```
Val Arg Phe Thr Lys Ile Leu Ser Leu Leu Arg Leu Leu Arg Leu Ser
            260                 265                 270

Arg Leu Ile Arg Tyr Ile His Gln Trp Glu Glu Ile Phe His Met Thr
        275                 280                 285

Tyr Asp Leu Ala Ser Ala Val Val Arg Ile Phe Asn Leu Ile Gly Met
    290                 295                 300

Met Leu Leu Leu Cys His Trp Asp Gly Cys Leu Gln Phe Leu Val Pro
305                 310                 315                 320

Leu Leu Gln Asp Phe Pro Pro Asp Cys Trp Val Ser Leu Asn Glu Met
                325                 330                 335

Val Asn Asp Ser Trp Gly Lys Gln Tyr Ser Tyr Ala Leu Phe Lys Ala
            340                 345                 350

Met Ser His Met Leu Cys Ile Gly Tyr Gly Ala Gln Ala Pro Val Ser
        355                 360                 365

Met Ser Asp Leu Trp Ile Thr Met Leu Ser Met Ile Val Gly Ala Thr
    370                 375                 380

Cys Tyr Ala Met Phe Val Gly His Ala Thr Ala Leu Ile Gln Ser Leu
385                 390                 395                 400

Asp Ser Ser Arg Arg Gln Tyr Gln Glu Lys Tyr Lys Gln Val Glu Gln
                405                 410                 415

Tyr Met Ser Phe His Lys Leu Pro Ala Asp Met Arg Gln Lys Ile His
            420                 425                 430

Asp Tyr Tyr Glu His Arg Tyr Gln Gly Lys Ile Phe Asp Glu Glu Asn
        435                 440                 445

Ile Leu Asn Glu Leu Asn Asp Pro Leu Arg Gly Glu Ile Val Asn Phe
    450                 455                 460

Asn Cys Arg Lys Leu Val Ala Thr Met Pro Leu Phe Ala Asn Ala Asp
465                 470                 475                 480

Pro Asn Phe Val Thr Ala Met Leu Ser Lys Leu Arg Phe Glu Val Phe
                485                 490                 495

Gln Pro Gly Asp Tyr Ile Val Arg Glu Gly Ala Val Gly Lys Lys Met
            500                 505                 510

Tyr Phe Ile Gln His Gly Val Ala Gly Val Ile Thr Lys Ser Ser Lys
        515                 520                 525

Glu Met Lys Leu Thr Asp Gly Ser Tyr Phe Gly Glu Ile Cys Leu Leu
    530                 535                 540

Thr Lys Gly Arg Arg Thr Ala Ser Val Arg Ala Asp Thr Tyr Cys Arg
545                 550                 555                 560

Leu Tyr Ser Leu Ser Val Asp Asn Phe Asn Glu Val Pro Glu Glu Tyr
                565                 570                 575

Pro Met Met Arg Arg Ala Phe Glu Thr Val Ala Ile Asp Arg Leu Asp
            580                 585                 590

Arg Ile Gly Lys Lys Asn Ser Ile Leu Leu Gln Lys Phe Gln Lys Asp
        595                 600                 605

Leu Asn Thr Gly Val Phe Asn Asn Gln Glu Asn Glu Ile Leu Lys Gln
    610                 615                 620

Ile Val Lys His Asp Arg Glu Met Val Gln Ala Ile Ala Pro Ile Asn
625                 630                 635                 640

Tyr Pro Gln Met Thr Thr Leu Asn Ser Ala Ser Ser Thr Thr Thr Pro
                645                 650                 655

Thr Ser Arg Met Arg Thr Gln Ser Pro Pro Val Tyr Thr Ala Thr Ser
            660                 665                 670

Leu Ser His Ser Asn Leu His Ser Pro Ser Pro Ser Thr Gln Thr Pro
        675                 680                 685
```

```
Gln Pro Ser Ala Ile Leu Ser Pro Cys Ser Tyr Thr Thr Ala Val Cys
    690                 695                 700

Ser Pro Pro Val Gln Ser Pro Leu Ala Ala Arg Thr Phe His Tyr Ala
705                 710                 715                 720

Ser Pro Thr Ala Ser Gln Leu Ser Leu Met Gln Gln Gln Pro Gln Gln
                725                 730                 735

Gln Val Gln Gln Ser Gln Pro Pro Gln Thr Gln Pro Gln Gln Pro Ser
            740                 745                 750

Pro Gln Pro Gln Thr Pro Gly Ser Ser Thr Pro Lys Asn Glu Val His
        755                 760                 765

Lys Ser Thr Gln Ala Leu His Asn Thr Asn Leu Thr Arg Glu Val Arg
    770                 775                 780

Pro Leu Ser Ala Ser Gln Pro Ser Leu Pro His Glu Val Pro Thr Leu
785                 790                 795                 800

Ile Ser Arg Pro His Pro Thr Val Gly Glu Ser Leu Ala Ser Ile Pro
                805                 810                 815

Gln Pro Val Thr Ala Val Pro Gly Thr Gly Leu Gln Ala Gly Gly Arg
            820                 825                 830

Ser Thr Val Pro Gln Arg Val Thr Leu Phe Arg Gln Met Ser Ser Gly
        835                 840                 845

Ala Ile Pro Pro Asn Arg Gly Val Pro Pro Ala Pro Pro Pro Pro Ala
    850                 855                 860

Ala Ala Leu Pro Arg Glu Ser Ser Ser Val Leu Asn Thr Asp Pro Asp
865                 870                 875                 880

Ala Glu Lys Pro Arg Phe Ala Ser Asn Leu
                885                 890


<210> SEQ ID NO 12
<211> LENGTH: 822
<212> TYPE: PRT
<213> ORGANISM: Oryctolagus cuniculus

<400> SEQUENCE: 12

Met Ala Thr Ala Ser Ser Pro Pro Arg Arg Pro Arg Arg Ala Arg Gly
  1               5                  10                  15

Leu Glu Asp Ala Glu Gly Pro Arg Arg Gln Tyr Gly Phe Met Gln Arg
            20                  25                  30

Gln Phe Thr Ser Met Leu Gln Pro Gly Val Asn Lys Phe Ser Leu Arg
        35                  40                  45

Met Phe Gly Ser Gln Lys Ala Val Glu Lys Glu Gln Glu Arg Val Lys
    50                  55                  60

Thr Ala Gly Phe Trp Ile Ile His Pro Tyr Ser Asp Phe Arg Phe Tyr
 65                  70                  75                  80

Trp Asp Leu Ile Met Leu Ile Met Met Val Gly Asn Leu Val Ile Ile
                85                  90                  95

Pro Val Gly Ile Thr Phe Phe Thr Glu Gln Thr Thr Thr Pro Trp Ile
            100                 105                 110

Ile Phe Asn Val Ala Ser Asp Thr Val Phe Leu Leu Asp Leu Ile Met
        115                 120                 125

Asn Phe Arg Thr Gly Thr Val Asn Glu Asp Ser Ser Glu Ile Ile Leu
    130                 135                 140

Asp Pro Lys Val Ile Lys Met Asn Tyr Leu Lys Ser Trp Phe Val Val
145                 150                 155                 160

Asp Phe Ile Ser Ser Ile Pro Val Asp Tyr Ile Phe Leu Ile Val Glu
                165                 170                 175
```

```
Lys Gly Met Asp Ser Glu Val Tyr Lys Thr Ala Arg Ala Leu Arg Ile
            180                 185                 190

Val Arg Phe Thr Lys Ile Leu Ser Leu Leu Arg Leu Leu Arg Leu Ser
        195                 200                 205

Arg Leu Ile Arg Tyr Ile His Gln Trp Glu Glu Ile Phe His Met Thr
    210                 215                 220

Tyr Asp Leu Ala Ser Ala Val Val Arg Ile Phe Asn Leu Ile Gly Met
225                 230                 235                 240

Met Leu Leu Leu Cys His Trp Asp Gly Cys Leu Gln Phe Leu Val Pro
                245                 250                 255

Leu Leu Gln Asp Phe Pro Pro Asp Cys Trp Val Ser Leu Asn Glu Met
            260                 265                 270

Val Asn Asp Ser Trp Gly Lys Gln Tyr Ser Tyr Ala Leu Phe Lys Ala
        275                 280                 285

Met Ser His Met Leu Cys Ile Gly Tyr Gly Ala Gln Ala Pro Val Ser
    290                 295                 300

Met Ser Asp Leu Trp Ile Thr Met Leu Ser Met Ile Val Gly Ala Thr
305                 310                 315                 320

Cys Tyr Ala Met Phe Val Gly His Ala Thr Ala Leu Ile Gln Ser Leu
                325                 330                 335

Asp Ser Ser Arg Arg Gln Tyr Gln Glu Lys Tyr Lys Gln Val Glu Gln
            340                 345                 350

Tyr Met Ser Phe His Lys Leu Pro Ala Asp Met Arg Gln Lys Ile His
        355                 360                 365

Asp Tyr Tyr Glu His Arg Tyr Gln Gly Lys Ile Phe Asp Glu Glu Asn
    370                 375                 380

Ile Leu Asn Glu Leu Asn Asp Pro Leu Arg Glu Glu Ile Val Asn Phe
385                 390                 395                 400

Asn Cys Arg Lys Leu Val Ala Thr Met Pro Leu Phe Ala Asn Ala Asp
                405                 410                 415

Pro Asn Phe Val Thr Ala Met Leu Ser Lys Leu Arg Phe Glu Val Phe
            420                 425                 430

Gln Pro Gly Asp Tyr Ile Ile Arg Glu Gly Ala Val Gly Lys Lys Met
        435                 440                 445

Tyr Phe Ile Gln His Gly Val Ala Gly Val Ile Thr Lys Ser Ser Lys
    450                 455                 460

Glu Met Lys Leu Thr Asp Gly Ser Tyr Phe Gly Glu Ile Cys Leu Leu
465                 470                 475                 480

Thr Lys Gly Arg Arg Thr Ala Ser Val Arg Ala Asp Thr Tyr Cys Arg
                485                 490                 495

Leu Tyr Ser Leu Ser Val Asp Asn Phe Asn Glu Val Leu Glu Glu Tyr
            500                 505                 510

Pro Met Met Arg Arg Ala Phe Glu Thr Val Ala Ile Asp Arg Leu Asp
        515                 520                 525

Arg Ile Gly Lys Lys Asn Ser Ile Leu Leu Gln Lys Phe Gln Lys Asp
    530                 535                 540

Leu Asn Thr Gly Val Phe Asn Asn Gln Glu Asn Glu Ile Leu Lys Gln
545                 550                 555                 560

Ile Val Lys His Asp Arg Glu Met Val Gln Ala Ile Ala Pro Ile Ser
                565                 570                 575

Tyr Pro Gln Met Thr Ala Leu Asn Ser Thr Ser Ser Thr Ala Thr Pro
            580                 585                 590

Thr Ser Arg Met Arg Thr Gln Ser Pro Pro Val Tyr Thr Ala Thr Ser
```

```
        595                 600                 605

Leu Ser His Ser Asn Leu His Ser Pro Ser Pro Ser Thr Gln Thr Pro
    610                 615                 620

Gln Pro Ser Ala Ile Leu Ser Pro Cys Ser Tyr Thr Thr Ala Val Cys
625                 630                 635                 640

Ser Pro Pro Val Gln Ser Pro Leu Ala Thr Arg Thr Phe His Tyr Ala
                645                 650                 655

Ser Pro Thr Ala Ser Gln Leu Ser Leu Met Pro Gln Gln Gln Gln Gln
            660                 665                 670

Pro Gln Ala Pro Gln Thr Gln Pro Gln Gln Pro Pro Gln Gln Pro Gln
        675                 680                 685

Thr Pro Gly Ser Ala Thr Pro Lys Asn Glu Val His Arg Ser Thr Gln
    690                 695                 700

Ala Leu Pro Asn Thr Ser Leu Thr Arg Glu Val Arg Pro Leu Ser Ala
705                 710                 715                 720

Ser Gln Pro Ser Leu Pro His Glu Val Ser Thr Leu Ile Ser Arg Pro
                725                 730                 735

His Pro Thr Val Gly Glu Ser Leu Ala Ser Ile Pro Gln Pro Val Ala
            740                 745                 750

Ala Val His Ser Ala Gly Leu Gln Ala Ala Gly Arg Ser Thr Val Pro
        755                 760                 765

Gln Arg Val Thr Leu Phe Arg Gln Met Ser Ser Gly Ala Ile Pro Pro
    770                 775                 780

Asn Arg Gly Val Pro Pro Ala Pro Pro Pro Pro Ala Ala Pro Leu Gln
785                 790                 795                 800

Arg Glu Ala Ser Ser Val Leu Asn Thr Asp Pro Glu Ala Glu Lys Pro
                805                 810                 815

Arg Phe Ala Ser Asn Leu
            820
```

<210> SEQ ID NO 13
<211> LENGTH: 202
<212> TYPE: PRT
<213> ORGANISM: Cavia porcellus

<400> SEQUENCE: 13

```
Ile Met Met Val Gly Asn Leu Val Ile Ile Pro Val Gly Ile Thr Phe
  1               5                  10                  15

Phe Thr Glu Gln Thr Thr Thr Pro Trp Ile Ile Phe Asn Val Ala Ser
             20                  25                  30

Asp Thr Val Phe Leu Leu Asp Leu Ile Met Asn Phe Arg Thr Gly Thr
         35                  40                  45

Val Asn Glu Asp Ser Ser Glu Ile Ile Leu Asp Pro Lys Val Ile Lys
     50                  55                  60

Met Asn Tyr Leu Lys Ser Trp Phe Val Val Asp Phe Ile Ser Ser Ile
 65                  70                  75                  80

Pro Val Asp Tyr Ile Phe Leu Ile Val Glu Lys Gly Met Asp Ser Glu
                 85                  90                  95

Val Tyr Lys Thr Ala Arg Ala Leu Arg Ile Val Arg Phe Thr Lys Ile
            100                 105                 110

Leu Ser Leu Leu Arg Leu Leu Arg Leu Ser Arg Leu Ile Arg Tyr Ile
        115                 120                 125

His Gln Trp Glu Glu Ile Phe His Met Thr Tyr Asp Leu Ala Ser Ala
    130                 135                 140

Val Val Arg Ile Phe Asn Leu Ile Gly Met Met Leu Leu Leu Cys His
```

```
145                 150                 155                 160

Trp Asp Gly Cys Leu Gln Phe Leu Val Pro Leu Leu Gln Asp Phe Pro
                165                 170                 175

Pro Asp Cys Trp Val Ser Leu Asn Lys Met Val Asn Val Ser Trp Gly
            180                 185                 190

Gln Gln Tyr Ser Tyr Ala Leu Phe Lys Ala
        195                 200


<210> SEQ ID NO 14
<211> LENGTH: 863
<212> TYPE: PRT
<213> ORGANISM: Mus musculus

<400> SEQUENCE: 14

Met Asp Ala Arg Gly Gly Gly Gly Arg Pro Gly Asp Ser Pro Gly Thr
  1               5                  10                  15

Thr Pro Ala Pro Gly Pro Pro Pro Pro Pro Pro Pro Pro Ala Pro Pro
            20                  25                  30

Gln Pro Gln Pro Pro Pro Ala Pro Pro Pro Asn Pro Thr Thr Pro Ser
        35                  40                  45

His Pro Glu Ser Ala Asp Glu Pro Gly Pro Arg Ala Arg Leu Cys Ser
     50                  55                  60

Arg Asp Ser Ala Cys Thr Pro Gly Ala Ala Lys Gly Gly Ala Asn Gly
 65                  70                  75                  80

Glu Cys Gly Arg Gly Glu Pro Gln Cys Ser Pro Glu Gly Pro Ala Arg
                 85                  90                  95

Gly Pro Lys Val Ser Phe Ser Cys Arg Gly Ala Ala Ser Gly Pro Ser
            100                 105                 110

Ala Ala Glu Glu Ala Gly Ser Glu Glu Ala Gly Pro Ala Gly Glu Pro
        115                 120                 125

Arg Gly Ser Gln Ala Ser Phe Leu Gln Arg Gln Phe Gly Ala Leu Leu
    130                 135                 140

Gln Pro Gly Val Asn Lys Phe Ser Leu Arg Met Phe Gly Ser Gln Lys
145                 150                 155                 160

Ala Val Glu Arg Glu Gln Glu Arg Val Lys Ser Ala Gly Ala Trp Ile
                165                 170                 175

Ile His Pro Tyr Ser Asp Phe Arg Phe Tyr Trp Asp Phe Thr Met Leu
            180                 185                 190

Leu Phe Met Val Gly Asn Leu Ile Ile Ile Pro Val Gly Ile Thr Phe
        195                 200                 205

Phe Lys Asp Glu Thr Thr Ala Pro Trp Ile Val Phe Asn Val Val Ser
    210                 215                 220

Asp Thr Phe Phe Leu Met Asp Leu Val Leu Asn Phe Arg Thr Gly Ile
225                 230                 235                 240

Val Ile Glu Asp Asn Thr Glu Ile Ile Leu Asp Pro Glu Lys Ile Lys
                245                 250                 255

Lys Lys Tyr Leu Arg Thr Trp Phe Val Val Asp Phe Val Ser Ser Ile
            260                 265                 270

Pro Val Asp Tyr Ile Phe Leu Ile Val Glu Lys Gly Ile Asp Ser Glu
        275                 280                 285

Val Tyr Lys Thr Ala Arg Ala Leu Arg Ile Val Arg Phe Thr Lys Ile
    290                 295                 300

Leu Ser Leu Leu Arg Leu Leu Arg Leu Ser Arg Leu Ile Arg Tyr Ile
305                 310                 315                 320

His Gln Trp Glu Glu Ile Phe His Met Thr Tyr Asp Leu Ala Ser Ala
```

```
                325                 330                 335

Val Met Arg Ile Cys Asn Leu Ile Ser Met Met Leu Leu Leu Cys His
            340                 345                 350

Trp Asp Gly Cys Leu Gln Phe Leu Val Pro Met Leu Gln Asp Phe Pro
        355                 360                 365

Ser Asp Cys Trp Val Ser Ile Asn Asn Met Val Asn His Ser Trp Ser
    370                 375                 380

Glu Leu Tyr Ser Phe Ala Leu Phe Lys Ala Met Ser His Met Leu Cys
385                 390                 395                 400

Ile Gly Tyr Gly Arg Gln Ala Pro Glu Ser Met Thr Asp Ile Trp Leu
                405                 410                 415

Thr Met Leu Ser Met Ile Val Gly Ala Thr Cys Tyr Ala Met Phe Ile
            420                 425                 430

Gly His Ala Thr Ala Leu Ile Gln Ser Leu Asp Ser Ser Arg Arg Gln
        435                 440                 445

Tyr Gln Glu Lys Tyr Lys Gln Val Glu Gln Tyr Met Ser Phe His Lys
    450                 455                 460

Leu Pro Ala Asp Phe Arg Gln Lys Ile His Asp Tyr Tyr Glu His Arg
465                 470                 475                 480

Tyr Gln Gly Lys Met Phe Asp Glu Asp Ser Ile Leu Gly Glu Leu Asn
                485                 490                 495

Gly Pro Leu Arg Glu Glu Ile Val Asn Phe Asn Cys Arg Lys Leu Val
            500                 505                 510

Ala Ser Met Pro Leu Phe Ala Asn Ala Asp Pro Asn Phe Val Thr Ala
        515                 520                 525

Met Leu Thr Lys Leu Lys Phe Glu Val Phe Gln Pro Gly Asp Tyr Ile
    530                 535                 540

Ile Arg Glu Gly Thr Ile Gly Lys Lys Met Tyr Phe Ile Gln His Gly
545                 550                 555                 560

Val Val Ser Val Leu Thr Lys Gly Asn Lys Glu Met Lys Leu Ser Asp
                565                 570                 575

Gly Ser Tyr Phe Gly Glu Ile Cys Leu Leu Thr Arg Gly Arg Arg Thr
            580                 585                 590

Ala Ser Val Arg Ala Asp Thr Tyr Cys Arg Leu Tyr Ser Leu Ser Val
        595                 600                 605

Asp Asn Phe Asn Glu Val Leu Glu Glu Tyr Pro Met Met Arg Arg Ala
    610                 615                 620

Phe Glu Thr Val Ala Ile Asp Arg Leu Asp Arg Ile Gly Lys Lys Asn
625                 630                 635                 640

Ser Ile Leu Leu His Lys Val Gln His Asp Leu Ser Ser Gly Val Phe
                645                 650                 655

Asn Asn Gln Glu Asn Ala Ile Ile Gln Glu Ile Val Lys Tyr Asp Arg
            660                 665                 670

Glu Met Val Gln Gln Ala Glu Leu Gly Gln Arg Val Gly Leu Phe Pro
        675                 680                 685

Pro Pro Pro Pro Pro Gln Val Thr Ser Ala Ile Ala Thr Leu Gln Gln
    690                 695                 700

Ala Val Ala Met Ser Phe Cys Pro Gln Val Ala Arg Pro Leu Val Gly
705                 710                 715                 720

Pro Leu Ala Leu Gly Ser Pro Arg Leu Val Arg Arg Ala Pro Pro Gly
                725                 730                 735

Pro Leu Pro Pro Ala Ala Ser Pro Gly Pro Pro Ala Ala Ser Pro Pro
            740                 745                 750
```

```
Ala Ala Pro Ser Ser Pro Arg Ala Pro Arg Thr Ser Pro Tyr Gly Val
        755                 760                 765

Pro Gly Ser Pro Ala Thr Arg Val Gly Pro Ala Leu Pro Ala Arg Arg
    770                 775                 780

Leu Ser Arg Ala Ser Arg Pro Leu Ser Ala Ser Gln Pro Ser Leu Pro
785                 790                 795                 800

His Gly Val Pro Ala Pro Ser Pro Ala Ala Ser Ala Arg Pro Ala Ser
                805                 810                 815

Ser Ser Thr Pro Arg Leu Gly Pro Ala Pro Thr Ala Arg Thr Ala Ala
            820                 825                 830

Pro Ser Pro Asp Arg Arg Asp Ser Ala Ser Pro Gly Ala Ala Ser Gly
        835                 840                 845

Leu Asp Pro Leu Asp Ser Ala Arg Ser Arg Leu Ser Ser Asn Leu
    850                 855                 860


<210> SEQ ID NO 15
<211> LENGTH: 863
<212> TYPE: PRT
<213> ORGANISM: Rattus norvegicus

<400> SEQUENCE: 15

Met Asp Ala Arg Gly Gly Gly Gly Arg Pro Gly Asp Ser Pro Gly Ala
  1               5                  10                  15

Thr Pro Ala Pro Gly Pro Pro Pro Pro Pro Pro Pro Pro Ala Pro Pro
            20                  25                  30

Gln Pro Gln Pro Pro Pro Ala Pro Pro Pro Asn Pro Thr Thr Pro Ser
        35                  40                  45

His Pro Glu Ser Ala Asp Glu Pro Gly Pro Arg Ser Arg Leu Cys Ser
     50                  55                  60

Arg Asp Ser Ser Cys Thr Pro Gly Ala Ala Lys Gly Gly Ala Asn Gly
 65                  70                  75                  80

Glu Cys Gly Arg Gly Glu Pro Gln Cys Ser Pro Glu Gly Pro Ala Arg
                 85                  90                  95

Gly Pro Lys Val Ser Phe Ser Cys Arg Gly Ala Ala Ser Gly Pro Ala
            100                 105                 110

Ala Ala Glu Glu Ala Gly Ser Glu Glu Ala Gly Pro Ala Gly Glu Pro
        115                 120                 125

Arg Gly Ser Gln Ala Ser Phe Leu Gln Arg Gln Phe Gly Ala Leu Leu
    130                 135                 140

Gln Pro Gly Val Asn Lys Phe Ser Leu Arg Met Phe Gly Ser Gln Lys
145                 150                 155                 160

Ala Val Glu Arg Glu Gln Glu Arg Val Lys Ser Ala Gly Ala Trp Ile
                165                 170                 175

Ile His Pro Tyr Ser Asp Phe Arg Phe Tyr Trp Asp Phe Thr Met Leu
            180                 185                 190

Leu Phe Met Val Gly Asn Leu Ile Ile Ile Pro Val Gly Ile Thr Phe
        195                 200                 205

Phe Lys Asp Glu Thr Thr Ala Pro Trp Ile Val Phe Asn Val Val Ser
    210                 215                 220

Asp Thr Phe Phe Leu Met Asp Leu Val Leu Asn Phe Arg Thr Gly Ile
225                 230                 235                 240

Val Ile Glu Asp Asn Thr Glu Ile Ile Leu Asp Pro Glu Lys Ile Lys
                245                 250                 255

Lys Lys Tyr Leu Arg Thr Trp Phe Val Val Asp Phe Val Ser Ser Ile
            260                 265                 270
```

```
Pro Val Asp Tyr Ile Phe Leu Ile Val Glu Lys Gly Ile Asp Ser Glu
        275                 280                 285

Val Tyr Lys Thr Ala Arg Ala Leu Arg Ile Val Arg Phe Thr Lys Ile
    290                 295                 300

Leu Ser Leu Leu Arg Leu Leu Arg Leu Ser Arg Leu Ile Arg Tyr Ile
305                 310                 315                 320

His Gln Trp Glu Glu Ile Phe His Met Thr Tyr Asp Leu Ala Ser Ala
                325                 330                 335

Val Met Arg Ile Cys Asn Leu Ile Ser Met Met Leu Leu Leu Cys His
            340                 345                 350

Trp Asp Gly Cys Leu Gln Phe Leu Val Pro Met Leu Gln Asp Phe Pro
        355                 360                 365

Ser Asp Cys Trp Val Ser Ile Asn Asn Met Val Asn His Ser Trp Ser
    370                 375                 380

Glu Leu Tyr Ser Phe Ala Leu Phe Lys Ala Met Ser His Met Leu Cys
385                 390                 395                 400

Ile Gly Tyr Gly Arg Gln Ala Pro Glu Ser Met Thr Asp Ile Trp Leu
                405                 410                 415

Thr Met Leu Ser Met Ile Val Gly Ala Thr Cys Tyr Ala Met Phe Ile
            420                 425                 430

Gly His Ala Thr Ala Leu Ile Gln Ser Leu Asp Ser Ser Arg Arg Gln
        435                 440                 445

Tyr Gln Glu Lys Tyr Lys Gln Val Glu Gln Tyr Met Ser Phe His Lys
    450                 455                 460

Leu Pro Ala Asp Phe Arg Gln Lys Ile His Asp Tyr Tyr Glu His Arg
465                 470                 475                 480

Tyr Gln Gly Lys Met Phe Asp Glu Asp Ser Ile Leu Gly Glu Leu Asn
                485                 490                 495

Gly Pro Leu Arg Glu Glu Ile Val Asn Phe Asn Cys Arg Lys Leu Val
            500                 505                 510

Ala Ser Met Pro Leu Phe Ala Asn Ala Asp Pro Asn Phe Val Thr Ala
        515                 520                 525

Met Leu Thr Lys Leu Lys Phe Glu Val Phe Gln Pro Gly Asp Tyr Ile
    530                 535                 540

Ile Arg Glu Gly Thr Ile Gly Lys Lys Met Tyr Phe Ile Gln His Gly
545                 550                 555                 560

Val Val Ser Val Leu Thr Lys Gly Asn Lys Glu Met Lys Leu Ser Asp
                565                 570                 575

Gly Ser Tyr Phe Gly Glu Ile Cys Leu Leu Thr Arg Gly Arg Arg Thr
            580                 585                 590

Ala Ser Val Arg Ala Asp Thr Tyr Cys Arg Leu Tyr Ser Leu Ser Val
        595                 600                 605

Asp Asn Phe Asn Glu Val Leu Glu Glu Tyr Pro Met Met Arg Arg Ala
    610                 615                 620

Phe Glu Thr Val Ala Ile Asp Arg Leu Asp Arg Ile Gly Lys Lys Asn
625                 630                 635                 640

Ser Ile Leu Leu His Lys Val Gln His Asp Leu Ser Ser Gly Val Phe
                645                 650                 655

Asn Asn Gln Glu Asn Ala Ile Ile Gln Glu Ile Val Lys Tyr Asp Arg
            660                 665                 670

Glu Met Val Gln Gln Ala Glu Leu Gly Gln Arg Val Gly Leu Phe Pro
        675                 680                 685

Pro Pro Pro Pro Pro Gln Val Thr Ser Ala Ile Ala Thr Leu Gln Gln
    690                 695                 700
```

```
Ala Val Ala Met Ser Phe Cys Pro Gln Val Ala Arg Pro Leu Val Gly
705                 710                 715                 720

Pro Leu Ala Leu Gly Ser Pro Arg Leu Val Arg Arg Ala Pro Pro Gly
                725                 730                 735

Pro Leu Pro Pro Ala Ala Ser Pro Gly Pro Pro Ala Ala Ser Pro Pro
            740                 745                 750

Ala Ala Pro Ser Ser Pro Arg Ala Pro Arg Thr Ser Pro Tyr Gly Val
        755                 760                 765

Pro Gly Ser Pro Ala Thr Arg Val Gly Pro Ala Leu Pro Ala Arg Arg
    770                 775                 780

Leu Ser Arg Ala Ser Arg Pro Leu Ser Ala Ser Gln Pro Ser Leu Pro
785                 790                 795                 800

His Gly Ala Pro Ala Pro Ser Pro Ala Ala Ser Ala Arg Pro Ala Ser
                805                 810                 815

Ser Ser Thr Pro Arg Leu Gly Pro Ala Pro Thr Thr Arg Thr Ala Ala
            820                 825                 830

Pro Ser Pro Asp Arg Arg Asp Ser Ala Ser Pro Gly Ala Ala Ser Gly
        835                 840                 845

Leu Asp Pro Leu Asp Ser Ala Arg Ser Arg Leu Ser Ser Asn Leu
    850                 855                 860


<210> SEQ ID NO 16
<211> LENGTH: 889
<212> TYPE: PRT
<213> ORGANISM: Homo sapiens

<400> SEQUENCE: 16

Met Asp Ala Arg Gly Gly Gly Gly Arg Pro Gly Glu Ser Pro Gly Ala
  1               5                  10                  15

Thr Pro Ala Pro Gly Pro Pro Pro Pro Pro Pro Pro Ala Pro Pro Gln
             20                  25                  30

Gln Gln Pro Pro Pro Pro Pro Pro Pro Ala Pro Pro Pro Gly Pro Gly
         35                  40                  45

Pro Ala Pro Pro Gln His Pro Pro Arg Ala Glu Ala Leu Pro Pro Glu
     50                  55                  60

Ala Ala Asp Glu Gly Gly Pro Arg Gly Arg Leu Arg Ser Arg Asp Ser
 65                  70                  75                  80

Ser Cys Gly Arg Pro Gly Thr Pro Gly Ala Ala Ser Thr Ala Lys Gly
                 85                  90                  95

Ser Pro Asn Gly Glu Cys Gly Arg Gly Glu Pro Gln Cys Ser Pro Ala
            100                 105                 110

Gly Pro Glu Gly Pro Ala Arg Gly Pro Lys Val Ser Phe Ser Cys Arg
        115                 120                 125

Gly Ala Ala Ser Gly Pro Ala Pro Gly Pro Gly Pro Ala Glu Glu Ala
    130                 135                 140

Gly Ser Glu Glu Ala Gly Pro Ala Gly Glu Pro Arg Gly Ser Gln Ala
145                 150                 155                 160

Ser Phe Met Gln Arg Gln Phe Gly Ala Leu Leu Gln Pro Gly Val Asn
                165                 170                 175

Lys Phe Ser Leu Arg Met Phe Gly Ser Gln Lys Ala Val Glu Arg Glu
            180                 185                 190

Gln Glu Arg Val Lys Ser Ala Gly Ala Trp Ile Ile His Pro Tyr Ser
        195                 200                 205

Asp Phe Arg Phe Tyr Trp Asp Phe Thr Met Leu Leu Phe Met Val Gly
    210                 215                 220
```

```
Asn Leu Ile Ile Ile Pro Val Gly Ile Thr Phe Phe Lys Asp Glu Thr
225                 230                 235                 240

Thr Ala Pro Trp Ile Val Phe Asn Val Val Ser Asp Thr Phe Phe Leu
                245                 250                 255

Met Asp Leu Val Leu Asn Phe Arg Thr Gly Ile Val Ile Glu Asp Asn
            260                 265                 270

Thr Glu Ile Ile Leu Asp Pro Glu Lys Ile Lys Lys Lys Tyr Leu Arg
        275                 280                 285

Thr Trp Phe Val Val Asp Phe Val Ser Ser Ile Pro Val Asp Tyr Ile
    290                 295                 300

Phe Leu Ile Val Glu Lys Gly Ile Asp Ser Glu Val Tyr Lys Thr Ala
305                 310                 315                 320

Arg Ala Leu Arg Ile Val Arg Phe Thr Lys Ile Leu Ser Leu Leu Arg
                325                 330                 335

Leu Leu Arg Leu Ser Arg Leu Ile Arg Tyr Ile His Gln Trp Glu Glu
            340                 345                 350

Ile Phe His Met Thr Tyr Asp Leu Ala Ser Ala Val Met Arg Ile Cys
        355                 360                 365

Asn Leu Ile Ser Met Met Leu Leu Leu Cys His Trp Asp Gly Cys Leu
    370                 375                 380

Gln Phe Leu Val Pro Met Leu Gln Asp Phe Pro Arg Asn Cys Trp Val
385                 390                 395                 400

Ser Ile Asn Gly Met Val Asn His Ser Trp Ser Glu Leu Tyr Ser Phe
                405                 410                 415

Ala Leu Phe Lys Ala Met Ser His Met Leu Cys Ile Gly Tyr Gly Arg
            420                 425                 430

Gln Ala Pro Glu Ser Met Thr Asp Ile Trp Leu Thr Met Leu Ser Met
        435                 440                 445

Ile Val Gly Ala Thr Cys Tyr Ala Met Phe Ile Gly His Ala Thr Ala
    450                 455                 460

Leu Ile Gln Ser Leu Asp Ser Ser Arg Arg Gln Tyr Gln Glu Lys Tyr
465                 470                 475                 480

Lys Gln Val Glu Gln Tyr Met Ser Phe His Lys Leu Pro Ala Asp Phe
                485                 490                 495

Arg Gln Lys Ile His Asp Tyr Tyr Glu His Arg Tyr Gln Gly Lys Met
            500                 505                 510

Phe Asp Glu Asp Ser Ile Leu Gly Glu Leu Asn Gly Pro Leu Arg Glu
        515                 520                 525

Glu Ile Val Asn Phe Asn Cys Arg Lys Leu Val Ala Ser Met Pro Leu
    530                 535                 540

Phe Ala Asn Ala Asp Pro Asn Phe Val Thr Ala Met Leu Thr Lys Leu
545                 550                 555                 560

Lys Phe Glu Val Phe Gln Pro Gly Asp Tyr Ile Ile Arg Glu Gly Thr
                565                 570                 575

Ile Gly Lys Lys Met Tyr Phe Ile Gln His Gly Val Val Ser Val Leu
            580                 585                 590

Thr Lys Gly Asn Lys Glu Met Lys Leu Ser Asp Gly Ser Tyr Phe Gly
        595                 600                 605

Glu Ile Cys Leu Leu Thr Arg Gly Arg Arg Thr Ala Ser Val Arg Ala
    610                 615                 620

Asp Thr Tyr Cys Arg Leu Tyr Ser Leu Ser Val Asp Asn Phe Asn Glu
625                 630                 635                 640

Val Leu Glu Glu Tyr Pro Met Met Arg Arg Ala Phe Glu Thr Val Ala
```

```
                645                 650                 655

Ile Asp Arg Leu Asp Arg Ile Gly Lys Lys Asn Ser Ile Leu Leu His
            660                 665                 670

Lys Val Gln His Asp Leu Asn Ser Gly Val Phe Asn Asn Gln Glu Asn
        675                 680                 685

Ala Ile Ile Gln Glu Ile Val Lys Tyr Asp Arg Glu Met Val Gln Gln
    690                 695                 700

Ala Glu Leu Gly Gln Arg Val Gly Leu Phe Pro Pro Pro Pro Pro Pro
705                 710                 715                 720

Pro Gln Val Thr Ser Ala Ile Ala Thr Leu Gln Gln Ala Ala Ala Met
                725                 730                 735

Ser Phe Cys Pro Gln Val Ala Arg Pro Leu Val Gly Pro Leu Ala Leu
            740                 745                 750

Gly Ser Pro Arg Leu Val Arg Arg Pro Pro Pro Gly Pro Ala Pro Ala
        755                 760                 765

Ala Ala Ser Pro Gly Pro Pro Pro Pro Ala Ser Pro Pro Gly Ala Pro
    770                 775                 780

Ala Ser Pro Arg Ala Pro Arg Thr Ser Pro Tyr Gly Gly Leu Pro Ala
785                 790                 795                 800

Ala Pro Leu Ala Gly Pro Ala Leu Pro Ala Arg Arg Leu Ser Arg Ala
                805                 810                 815

Ser Arg Pro Leu Ser Ala Ser Gln Pro Ser Leu Pro His Gly Ala Pro
            820                 825                 830

Gly Pro Ala Ala Ser Thr Arg Pro Ala Ser Ser Ser Thr Pro Arg Leu
        835                 840                 845

Arg Pro Thr Pro Ala Ala Arg Ala Ala Ala Pro Ser Pro Asp Arg Arg
    850                 855                 860

Asp Ser Ala Ser Pro Gly Ala Ala Gly Gly Leu Asp Pro Gln Asp Ser
865                 870                 875                 880

Ala Arg Ser Arg Leu Ser Ser Asn Leu
                885


<210> SEQ ID NO 17
<211> LENGTH: 97
<212> TYPE: PRT
<213> ORGANISM: Canis familiaris

<400> SEQUENCE: 17

Ala Met Ser His Met Leu Cys Ile Gly Tyr Gly Arg Gln Ala Pro Glu
  1               5                  10                  15

Ser Met Thr Asp Ile Trp Leu Thr Met Leu Ser Met Ile Val Gly Ala
            20                  25                  30

Thr Cys Tyr Ala Met Phe Ile Gly His Ala Thr Ala Leu Ile Gln Ser
         35                  40                  45

Leu Asp Ser Ser Arg Arg Gln Tyr Gln Glu Lys Tyr Lys Gln Val Glu
     50                  55                  60

Gln Tyr Met Ser Phe His Lys Leu Pro Ala Asp Phe Arg Gln Lys Ile
 65                  70                  75                  80

His Asp Tyr Tyr Glu His Arg Tyr Gln Gly Lys Met Phe Asp Glu Glu
                 85                  90                  95

Ser


<210> SEQ ID NO 18
<211> LENGTH: 1186
<212> TYPE: PRT
<213> ORGANISM: Mus musculus
```

<400> SEQUENCE: 18

```
Met Asp Lys Leu Pro Pro Ser Met Arg Lys Arg Leu Tyr Ser Leu Pro
1               5                   10                  15

Gln Gln Val Gly Ala Lys Ala Trp Ile Met Asp Glu Glu Glu Asp Gly
            20                  25                  30

Glu Glu Glu Gly Ala Gly Gly Arg Gln Asp Pro Ser Arg Arg Ser Ile
        35                  40                  45

Arg Leu Arg Pro Leu Pro Ser Pro Ser Pro Ser Val Ala Ala Gly Cys
    50                  55                  60

Ser Glu Ser Arg Gly Ala Ala Leu Gly Ala Thr Glu Ser Glu Gly Pro
65                  70                  75                  80

Gly Arg Ser Ala Gly Lys Ser Ser Thr Asn Gly Asp Cys Arg Arg Phe
                85                  90                  95

Arg Gly Ser Leu Ala Ser Leu Gly Ser Arg Gly Gly Gly Ser Gly Gly
            100                 105                 110

Ala Gly Gly Gly Ser Ser Leu Gly His Leu His Asp Ser Ala Glu Glu
        115                 120                 125

Arg Arg Leu Ile Ala Ala Glu Gly Asp Ala Ser Pro Gly Glu Asp Arg
    130                 135                 140

Thr Pro Pro Gly Leu Ala Thr Glu Pro Glu Arg Pro Ala Thr Ala Ala
145                 150                 155                 160

Gln Pro Ala Ala Ser Pro Pro Pro Gln Gln Pro Pro Gln Pro Ala Ser
                165                 170                 175

Ala Ser Cys Glu Gln Pro Ser Ala Asp Thr Ala Ile Lys Val Glu Gly
            180                 185                 190

Gly Ala Ala Ala Ile Asp His Ile Leu Pro Glu Ala Glu Val Arg Leu
        195                 200                 205

Gly Gln Ser Gly Phe Met Gln Arg Gln Phe Gly Ala Met Leu Gln Pro
    210                 215                 220

Gly Val Asn Lys Phe Ser Leu Arg Met Phe Gly Ser Gln Lys Ala Val
225                 230                 235                 240

Glu Arg Glu Gln Glu Arg Val Lys Ser Ala Gly Phe Trp Ile Ile His
                245                 250                 255

Pro Tyr Ser Asp Phe Arg Phe Tyr Trp Asp Leu Thr Met Leu Leu Leu
            260                 265                 270

Met Val Gly Asn Leu Ile Ile Ile Pro Val Gly Ile Thr Phe Phe Lys
        275                 280                 285

Asp Glu Asn Thr Thr Pro Trp Ile Val Phe Asn Val Val Ser Asp Thr
    290                 295                 300

Phe Phe Leu Ile Asp Leu Val Leu Asn Phe Arg Thr Gly Ile Val Val
305                 310                 315                 320

Glu Asp Asn Thr Glu Ile Ile Leu Asp Pro Gln Arg Ile Lys Met Lys
                325                 330                 335

Tyr Leu Lys Ser Trp Phe Val Val Asp Phe Ile Ser Ser Ile Pro Val
            340                 345                 350

Glu Tyr Ile Phe Leu Ile Val Glu Thr Arg Ile Asp Ser Glu Val Tyr
        355                 360                 365

Lys Thr Ala Arg Ala Val Arg Ile Val Arg Phe Thr Lys Ile Leu Ser
    370                 375                 380

Leu Leu Arg Leu Leu Arg Leu Ser Arg Leu Ile Arg Tyr Ile His Gln
385                 390                 395                 400

Trp Glu Glu Ile Phe His Met Thr Tyr Asp Leu Ala Ser Ala Val Val
                405                 410                 415
```

```
Arg Ile Val Asn Leu Ile Gly Met Met Leu Leu Leu Cys His Trp Asp
            420                 425                 430

Gly Cys Leu Gln Phe Leu Val Pro Met Leu Gln Asp Phe Pro His Asp
        435                 440                 445

Cys Trp Val Ser Ile Asn Gly Met Val Asn Asn Ser Trp Gly Lys Gln
    450                 455                 460

Tyr Ser Tyr Ala Leu Phe Lys Ala Met Ser His Met Leu Cys Ile Gly
465                 470                 475                 480

Tyr Gly Arg Gln Ala Pro Val Gly Met Ser Asp Val Trp Leu Thr Met
                485                 490                 495

Leu Ser Met Ile Val Gly Ala Thr Cys Tyr Ala Met Phe Ile Gly His
            500                 505                 510

Ala Thr Ala Leu Ile Gln Ser Leu Asp Ser Ser Arg Arg Gln Tyr Gln
        515                 520                 525

Glu Lys Tyr Lys Gln Val Glu Gln Tyr Met Ser Phe His Lys Leu Pro
    530                 535                 540

Pro Asp Thr Arg Gln Arg Ile His Asp Tyr Tyr Glu His Arg Tyr Gln
545                 550                 555                 560

Gly Lys Met Phe Asp Glu Glu Ser Ile Leu Gly Glu Leu Ser Glu Pro
                565                 570                 575

Leu Arg Glu Glu Ile Ile Asn Phe Asn Cys Arg Lys Leu Val Ala Ser
            580                 585                 590

Met Pro Leu Phe Ala Asn Ala Asp Pro Asn Phe Val Thr Ser Met Leu
        595                 600                 605

Thr Lys Leu Arg Phe Glu Val Phe Gln Pro Gly Asp Tyr Ile Ile Arg
    610                 615                 620

Glu Gly Thr Ile Gly Lys Lys Met Tyr Phe Ile Gln His Gly Val Val
625                 630                 635                 640

Ser Val Leu Thr Lys Gly Asn Lys Glu Thr Arg Leu Ala Asp Gly Ser
                645                 650                 655

Tyr Phe Gly Glu Ile Cys Leu Leu Thr Arg Gly Arg Arg Thr Ala Ser
            660                 665                 670

Val Arg Ala Asp Thr Tyr Cys Arg Leu Tyr Ser Leu Ser Val Asp Asn
        675                 680                 685

Phe Asn Glu Val Leu Glu Glu Tyr Pro Met Met Arg Lys Lys Asn Ser
    690                 695                 700

Ile Leu Leu His Lys Val Gln His Asp Leu Asn Ser Gly Val Phe Asn
705                 710                 715                 720

Tyr Gln Glu Asn Glu Ile Ile Gln Gln Ile Val Arg His Asp Arg Glu
                725                 730                 735

Met Ala His Cys Ala His Arg Val Gln Ala Ala Ala Ser Ala Thr Pro
            740                 745                 750

Thr Pro Thr Pro Val Ile Trp Thr Pro Leu Ile Gln Ala Pro Leu Gln
        755                 760                 765

Ala Ala Ala Ala Thr Thr Ser Val Ala Ile Ala Leu Thr His His Pro
    770                 775                 780

Arg Leu Pro Ala Ala Ile Phe Arg Pro Pro Pro Gly Pro Gly Leu Gly
785                 790                 795                 800

Asn Leu Gly Ala Gly Gln Thr Pro Arg His Pro Arg Arg Leu Gln Ser
                805                 810                 815

Leu Ile Pro Ser Ala Leu Gly Ser Ala Ser Pro Ala Ser Ser Pro Ser
            820                 825                 830

Gln Val Asp Thr Pro Ser Ser Ser Ser Phe His Ile Gln Gln Leu Ala
```

```
        835                 840                 845

Gly Phe Ser Ala Pro Pro Gly Leu Ser Pro Leu Leu Pro Ser Ser Ser
    850                 855                 860

Ser Ser Pro Pro Pro Gly Ala Cys Gly Ser Pro Pro Ala Pro Thr Pro
865                 870                 875                 880

Ser Thr Ser Thr Ala Ala Ala Ala Ser Thr Thr Gly Phe Gly His Phe
                885                 890                 895

His Lys Ala Leu Gly Gly Ser Leu Ser Ser Ser Asp Ser Pro Leu Leu
            900                 905                 910

Thr Pro Leu Gln Pro Gly Ala Arg Ser Pro Gln Ala Ala Gln Pro Pro
        915                 920                 925

Pro Pro Leu Pro Gly Ala Arg Gly Gly Leu Gly Leu Leu Glu His Phe
    930                 935                 940

Leu Pro Pro Pro Pro Ser Ser Arg Ser Pro Ser Ser Ser Pro Gly Gln
945                 950                 955                 960

Leu Gly Gln Pro Pro Gly Glu Leu Ser Leu Gly Leu Ala Ala Gly Pro
                965                 970                 975

Ser Ser Thr Pro Glu Thr Pro Pro Arg Pro Glu Arg Pro Ser Phe Met
            980                 985                 990

Ala Gly Ala Ser Gly Gly Ala Ser Pro Val Ala Phe Thr Pro Arg Gly
        995                 1000                1005

Gly Leu Ser Pro Pro Gly His Ser Pro Gly Pro Pro Arg Thr Phe Pro
   1010                1015                1020

Ser Ala Pro Pro Arg Ala Ser Gly Ser His Gly Ser Leu Leu Leu Pro
1025                1030                1035                1040

Pro Ala Ser Ser Pro Pro Pro Pro Gln Val Pro Gln Arg Arg Gly Thr
               1045                1050                1055

Pro Pro Leu Thr Pro Gly Arg Leu Thr Gln Asp Leu Lys Leu Ile Ser
           1060                1065                1070

Ala Ser Gln Pro Ala Leu Pro Gln Asp Gly Ala Gln Thr Leu Arg Arg
       1075                1080                1085

Ala Ser Pro His Ser Ser Gly Glu Ser Val Ala Ala Phe Ser Leu Tyr
   1090                1095                1100

Pro Arg Ala Gly Gly Gly Ser Gly Ser Ser Gly Gly Leu Gly Pro Pro
1105                1110                1115                1120

Gly Arg Pro Tyr Gly Ala Ile Pro Gly Gln His Val Thr Leu Pro Arg
               1125                1130                1135

Lys Thr Ser Ser Gly Ser Leu Pro Pro Pro Leu Ser Leu Phe Gly Ala
           1140                1145                1150

Arg Ala Ala Ser Ser Gly Gly Pro Pro Leu Thr Thr Ala Ala Pro Gln
       1155                1160                1165

Arg Glu Pro Gly Ala Arg Ser Glu Pro Val Arg Ser Lys Leu Pro Ser
   1170                1175                1180

Asn Leu
1185


<210> SEQ ID NO 19
<211> LENGTH: 1198
<212> TYPE: PRT
<213> ORGANISM: Rattus norvegicus

<400> SEQUENCE: 19

Met Asp Lys Leu Pro Pro Ser Met Arg Lys Arg Leu Tyr Ser Leu Pro
  1               5                  10                  15

Gln Gln Val Gly Ala Lys Ala Trp Ile Met Asp Glu Glu Glu Asp Gly
```

```
            20                  25                  30

Glu Glu Glu Gly Ala Gly Gly Leu Gln Asp Pro Ser Arg Arg Ser Ile
        35                  40                  45

Arg Leu Arg Pro Leu Pro Ser Pro Ser Pro Ser Val Ala Ala Gly Cys
    50                  55                  60

Ser Glu Ser Arg Gly Ala Ala Leu Gly Ala Ala Asp Ser Glu Gly Pro
65                  70                  75                  80

Gly Arg Ser Ala Gly Lys Ser Ser Thr Asn Gly Asp Cys Arg Arg Phe
                85                  90                  95

Arg Gly Ser Leu Ala Ser Leu Gly Ser Arg Gly Gly Gly Ser Gly Gly
            100                 105                 110

Ala Gly Gly Gly Ser Ser Leu Gly His Leu His Asp Ser Ala Glu Glu
        115                 120                 125

Arg Arg Leu Ile Ala Ala Glu Gly Asp Ala Ser Pro Gly Glu Asp Arg
    130                 135                 140

Thr Pro Pro Gly Leu Ala Thr Glu Pro Glu Arg Pro Gly Ala Ala Ala
145                 150                 155                 160

Gln Pro Ala Ala Ser Pro Pro Pro Gln Gln Pro Pro Gln Pro Ala Ser
                165                 170                 175

Ala Ser Cys Glu Gln Pro Ser Ala Asp Thr Ala Ile Lys Val Glu Gly
            180                 185                 190

Gly Ala Ala Ala Ser Asp Gln Ile Leu Pro Glu Ala Glu Val Arg Leu
        195                 200                 205

Gly Gln Ser Gly Phe Met Gln Arg Gln Phe Gly Ala Met Leu Gln Pro
    210                 215                 220

Gly Val Asn Lys Phe Ser Leu Arg Met Phe Gly Ser Gln Lys Ala Val
225                 230                 235                 240

Glu Arg Glu Gln Glu Arg Val Lys Ser Ala Gly Phe Trp Ile Ile His
                245                 250                 255

Pro Tyr Ser Asp Phe Arg Phe Tyr Trp Asp Leu Thr Met Leu Leu Leu
            260                 265                 270

Met Val Gly Asn Leu Ile Ile Ile Pro Val Gly Ile Thr Phe Phe Lys
        275                 280                 285

Asp Glu Asn Thr Thr Pro Trp Ile Val Phe Asn Val Val Ser Asp Thr
    290                 295                 300

Phe Phe Leu Ile Asp Leu Val Leu Asn Phe Arg Thr Gly Ile Val Val
305                 310                 315                 320

Glu Asp Asn Thr Glu Ile Ile Leu Asp Pro Gln Arg Ile Lys Met Lys
                325                 330                 335

Tyr Leu Lys Ser Trp Phe Val Val Asp Phe Ile Ser Ser Ile Pro Val
            340                 345                 350

Asp Tyr Ile Phe Leu Ile Val Glu Thr Arg Ile Asp Ser Glu Val Tyr
        355                 360                 365

Lys Thr Ala Arg Ala Leu Arg Ile Val Arg Phe Thr Lys Ile Leu Ser
    370                 375                 380

Leu Leu Arg Leu Leu Arg Leu Ser Arg Leu Ile Arg Tyr Ile His Gln
385                 390                 395                 400

Trp Glu Glu Ile Phe His Met Thr Tyr Asp Leu Ala Ser Ala Val Val
                405                 410                 415

Arg Ile Val Asn Leu Ile Gly Met Met Leu Leu Leu Cys His Trp Asp
            420                 425                 430

Gly Cys Leu Gln Phe Leu Val Pro Met Leu Gln Asp Phe Pro His Asp
        435                 440                 445
```

```
Cys Trp Val Ser Ile Asn Gly Met Val Asn Asn Ser Trp Gly Lys Gln
    450                 455                 460

Tyr Ser Tyr Ala Leu Phe Lys Ala Met Ser His Met Leu Cys Ile Gly
465                 470                 475                 480

Tyr Gly Arg Gln Ala Pro Val Gly Met Ser Asp Val Trp Leu Thr Met
                485                 490                 495

Leu Ser Met Ile Val Gly Ala Thr Cys Tyr Ala Met Phe Ile Gly His
            500                 505                 510

Ala Thr Ala Leu Ile Gln Ser Leu Asp Ser Ser Arg Arg Gln Tyr Gln
        515                 520                 525

Glu Lys Tyr Lys Gln Val Glu Gln Tyr Met Ser Phe His Lys Leu Pro
    530                 535                 540

Pro Asp Thr Arg Gln Arg Ile His Asp Tyr Tyr Glu His Arg Tyr Gln
545                 550                 555                 560

Gly Lys Met Phe Asp Glu Glu Ser Ile Leu Gly Glu Leu Ser Glu Pro
                565                 570                 575

Leu Arg Glu Glu Ile Ile Asn Phe Asn Cys Arg Lys Leu Val Ala Ser
            580                 585                 590

Met Pro Leu Phe Ala Asn Ala Asp Pro Asn Phe Val Thr Ser Met Leu
        595                 600                 605

Thr Lys Leu Arg Phe Glu Val Phe Gln Pro Gly Asp Tyr Ile Ile Arg
    610                 615                 620

Glu Gly Thr Ile Gly Lys Lys Met Tyr Phe Ile Gln His Gly Val Val
625                 630                 635                 640

Ser Val Leu Thr Lys Gly Asn Lys Glu Thr Lys Leu Ala Asp Gly Ser
                645                 650                 655

Tyr Phe Gly Glu Ile Cys Leu Leu Thr Arg Gly Arg Arg Thr Ala Ser
            660                 665                 670

Val Arg Ala Asp Thr Tyr Cys Arg Leu Tyr Ser Leu Ser Val Asp Asn
        675                 680                 685

Phe Asn Glu Val Leu Glu Glu Tyr Pro Met Met Arg Arg Ala Phe Glu
    690                 695                 700

Thr Val Ala Leu Asp Arg Leu Asp Arg Ile Gly Lys Lys Asn Ser Ile
705                 710                 715                 720

Leu Leu His Lys Val Gln His Asp Leu Asn Ser Gly Val Phe Asn Tyr
                725                 730                 735

Gln Glu Asn Glu Ile Ile Gln Gln Ile Val Arg His Asp Arg Glu Met
            740                 745                 750

Ala His Cys Ala His Arg Val Gln Ala Ala Ala Ser Ala Thr Pro Thr
        755                 760                 765

Pro Thr Pro Val Ile Trp Thr Pro Leu Ile Gln Ala Pro Leu Gln Ala
    770                 775                 780

Ala Ala Ala Thr Thr Ser Val Ala Ile Ala Leu Thr His His Pro Arg
785                 790                 795                 800

Leu Pro Ala Ala Ile Phe Arg Pro Pro Pro Gly Pro Gly Leu Gly Asn
                805                 810                 815

Leu Gly Ala Gly Gln Thr Pro Arg His Pro Arg Arg Leu Gln Ser Leu
            820                 825                 830

Ile Pro Ser Ala Leu Gly Ser Ala Ser Pro Ala Ser Ser Pro Ser Gln
        835                 840                 845

Val Asp Thr Pro Ser Ser Ser Ser Phe His Ile Gln Gln Leu Ala Gly
    850                 855                 860

Phe Ser Ala Pro Pro Gly Leu Ser Pro Leu Leu Pro Ser Ser Ser Ser
865                 870                 875                 880
```

```
Ser Pro Pro Pro Gly Ala Cys Ser Ser Pro Pro Ala Pro Thr Pro Ser
                885                 890                 895

Thr Ser Thr Ala Ala Thr Thr Thr Gly Phe Gly His Phe His Lys Ala
            900                 905                 910

Leu Gly Gly Ser Leu Ser Ser Ser Asp Ser Pro Leu Leu Thr Pro Leu
        915                 920                 925

Gln Pro Gly Ala Arg Ser Pro Gln Ala Ala Gln Pro Pro Pro Pro Leu
    930                 935                 940

Pro Gly Ala Arg Gly Gly Leu Gly Leu Leu Glu His Phe Leu Pro Pro
945                 950                 955                 960

Pro Pro Ser Ser Arg Ser Pro Ser Ser Ser Pro Gly Gln Leu Gly Gln
                965                 970                 975

Pro Pro Gly Glu Leu Ser Pro Gly Leu Ala Ala Gly Pro Pro Ser Thr
            980                 985                 990

Pro Glu Thr Pro Pro Arg Pro Glu Arg Pro Ser Phe Met Ala Gly Ala
        995                 1000                1005

Ser Gly Gly Ala Ser Pro Val Ala Phe Thr Pro Arg Gly Gly Leu Ser
   1010                 1015                1020

Pro Pro Gly His Ser Pro Gly Pro Pro Arg Thr Phe Pro Ser Ala Pro
1025                1030                1035                1040

Pro Arg Ala Ser Gly Ser His Gly Ser Leu Leu Leu Pro Pro Ala Ser
               1045                1050                1055

Ser Pro Pro Pro Pro Gln Val Pro Gln Arg Arg Gly Thr Pro Pro Leu
           1060                1065                1070

Thr Pro Gly Arg Leu Thr Gln Asp Leu Lys Leu Ile Ser Ala Ser Gln
       1075                1080                1085

Pro Ala Leu Pro Gln Asp Gly Ala Gln Thr Leu Arg Arg Ala Ser Pro
   1090                1095                1100

His Ser Ser Gly Glu Ser Met Ala Ala Phe Ser Leu Tyr Pro Arg Ala
1105                1110                1115                1120

Gly Gly Gly Ser Gly Ser Ser Gly Gly Leu Gly Pro Pro Gly Arg Pro
               1125                1130                1135

Tyr Gly Ala Ile Pro Gly Gln His Val Thr Leu Pro Arg Lys Thr Ser
           1140                1145                1150

Ser Gly Ser Leu Pro Pro Pro Leu Ser Leu Phe Gly Ala Arg Ala Ala
       1155                1160                1165

Ser Ser Gly Gly Pro Pro Leu Thr Ala Ala Pro Gln Arg Glu Pro Gly
   1170                1175                1180

Ala Arg Ser Glu Pro Val Arg Ser Lys Leu Pro Ser Asn Leu
1185                1190                1195


<210> SEQ ID NO 20
<211> LENGTH: 1203
<212> TYPE: PRT
<213> ORGANISM: Homo sapiens

<400> SEQUENCE: 20

Met Asp Lys Leu Pro Pro Ser Met Arg Lys Arg Leu Tyr Ser Leu Pro
  1               5                  10                  15

Gln Gln Val Gly Ala Lys Ala Trp Ile Met Asp Glu Glu Glu Asp Ala
             20                  25                  30

Glu Glu Glu Gly Ala Gly Gly Arg Gln Asp Pro Ser Arg Arg Ser Ile
         35                  40                  45

Arg Leu Arg Pro Leu Pro Ser Pro Ser Pro Ser Ala Ala Ala Gly Gly
     50                  55                  60
```

```
Thr Glu Ser Arg Ser Ser Ala Leu Gly Ala Ala Asp Ser Glu Gly Pro
 65                  70                  75                  80

Ala Arg Gly Ala Gly Lys Ser Ser Thr Asn Gly Asp Cys Arg Arg Phe
                 85                  90                  95

Arg Gly Ser Leu Ala Ser Leu Gly Ser Arg Gly Gly Gly Ser Gly Gly
            100                 105                 110

Thr Gly Ser Gly Ser Ser His Gly His Leu His Asp Ser Ala Glu Glu
        115                 120                 125

Arg Arg Leu Ile Ala Glu Gly Asp Ala Ser Pro Gly Glu Asp Arg Thr
    130                 135                 140

Pro Pro Gly Leu Ala Ala Glu Pro Glu Arg Pro Gly Ala Ser Ala Gln
145                 150                 155                 160

Pro Ala Ala Ser Pro Pro Pro Pro Gln Gln Pro Pro Gln Pro Ala Ser
                165                 170                 175

Ala Ser Cys Glu Gln Pro Ser Val Asp Thr Ala Ile Lys Val Glu Gly
            180                 185                 190

Gly Ala Ala Ala Gly Asp Gln Ile Leu Pro Glu Ala Glu Val Arg Leu
        195                 200                 205

Gly Gln Ala Gly Phe Met Gln Arg Gln Phe Gly Ala Met Leu Gln Pro
    210                 215                 220

Gly Val Asn Lys Phe Ser Leu Arg Met Phe Gly Ser Gln Lys Ala Val
225                 230                 235                 240

Glu Arg Glu Gln Glu Arg Val Lys Ser Ala Gly Phe Trp Ile Ile His
                245                 250                 255

Pro Tyr Ser Asp Phe Arg Phe Tyr Trp Asp Leu Thr Met Leu Leu Leu
            260                 265                 270

Met Val Gly Asn Leu Ile Ile Ile Pro Val Gly Ile Thr Phe Phe Lys
        275                 280                 285

Asp Glu Asn Thr Thr Pro Trp Ile Val Phe Asn Val Val Ser Asp Thr
    290                 295                 300

Phe Phe Leu Ile Asp Leu Val Leu Asn Phe Arg Thr Gly Ile Val Val
305                 310                 315                 320

Glu Asp Asn Thr Glu Ile Ile Leu Asp Pro Gln Arg Ile Lys Met Lys
                325                 330                 335

Tyr Leu Lys Ser Trp Phe Met Val Asp Phe Ile Ser Ser Ile Pro Val
            340                 345                 350

Asp Tyr Ile Phe Leu Ile Val Glu Thr Arg Ile Asp Ser Glu Val Tyr
        355                 360                 365

Lys Thr Ala Arg Ala Leu Arg Ile Val Arg Phe Thr Lys Ile Leu Ser
    370                 375                 380

Leu Leu Arg Leu Leu Arg Leu Ser Arg Leu Ile Arg Tyr Ile His Gln
385                 390                 395                 400

Trp Glu Glu Ile Phe His Met Thr Tyr Asp Leu Ala Ser Ala Val Val
                405                 410                 415

Arg Ile Val Asn Leu Ile Gly Met Met Leu Leu Leu Cys His Trp Asp
            420                 425                 430

Gly Cys Leu Gln Phe Leu Val Pro Met Leu Gln Asp Phe Pro Asp Asp
        435                 440                 445

Cys Trp Val Ser Ile Asn Asn Met Val Asn Asn Ser Trp Gly Lys Gln
    450                 455                 460

Tyr Ser Tyr Ala Leu Phe Lys Ala Met Ser His Met Leu Cys Ile Gly
465                 470                 475                 480

Tyr Gly Arg Gln Ala Pro Val Gly Met Ser Asp Val Trp Leu Thr Met
```

```
                485                 490                 495

Leu Ser Met Ile Val Gly Ala Thr Cys Tyr Ala Met Phe Ile Gly His
            500                 505                 510

Ala Thr Ala Leu Ile Gln Ser Leu Asp Ser Ser Arg Arg Gln Tyr Gln
        515                 520                 525

Glu Lys Tyr Lys Gln Val Glu Gln Tyr Met Ser Phe His Lys Leu Pro
    530                 535                 540

Pro Asp Thr Arg Gln Arg Ile His Asp Tyr Tyr Glu His Arg Tyr Gln
545                 550                 555                 560

Gly Lys Met Phe Asp Glu Glu Ser Ile Leu Gly Glu Leu Ser Glu Pro
                565                 570                 575

Leu Arg Glu Glu Ile Ile Asn Phe Asn Cys Arg Lys Leu Val Ala Ser
            580                 585                 590

Met Pro Leu Phe Ala Asn Ala Asp Pro Asn Phe Val Thr Ser Met Leu
        595                 600                 605

Thr Lys Leu Arg Phe Glu Val Phe Gln Pro Gly Asp Tyr Ile Ile Arg
    610                 615                 620

Glu Gly Thr Ile Gly Lys Lys Met Tyr Phe Ile Gln His Gly Val Val
625                 630                 635                 640

Ser Val Leu Thr Lys Gly Asn Lys Glu Thr Lys Leu Ala Asp Gly Ser
                645                 650                 655

Tyr Phe Gly Glu Ile Cys Leu Leu Thr Arg Gly Arg Arg Thr Ala Ser
            660                 665                 670

Val Arg Ala Asp Thr Tyr Cys Arg Leu Tyr Ser Leu Ser Val Asp Asn
        675                 680                 685

Phe Asn Glu Val Leu Glu Glu Tyr Pro Met Met Arg Arg Ala Phe Glu
    690                 695                 700

Thr Val Ala Leu Asp Arg Leu Asp Arg Ile Gly Lys Lys Asn Ser Ile
705                 710                 715                 720

Leu Leu His Lys Val Gln His Asp Leu Asn Ser Gly Val Phe Asn Tyr
                725                 730                 735

Gln Glu Asn Glu Ile Ile Gln Gln Ile Val Gln His Asp Arg Glu Met
            740                 745                 750

Ala His Cys Ala His Arg Val Gln Ala Ala Ala Ser Ala Thr Pro Thr
        755                 760                 765

Pro Thr Pro Val Ile Trp Thr Pro Leu Ile Gln Ala Pro Leu Gln Ala
    770                 775                 780

Ala Ala Ala Thr Thr Ser Val Ala Ile Ala Leu Thr His His Pro Arg
785                 790                 795                 800

Leu Pro Ala Ala Ile Phe Arg Pro Pro Pro Gly Ser Gly Leu Gly Asn
                805                 810                 815

Leu Gly Ala Gly Gln Thr Pro Arg His Leu Lys Arg Leu Gln Ser Leu
            820                 825                 830

Ile Pro Ser Ala Leu Gly Ser Ala Ser Pro Ala Ser Ser Pro Ser Gln
        835                 840                 845

Val Asp Thr Pro Ser Ser Ser Ser Phe His Ile Gln Gln Leu Ala Gly
    850                 855                 860

Phe Ser Ala Pro Ala Gly Leu Ser Pro Leu Leu Pro Ser Ser Ser Ser
865                 870                 875                 880

Ser Pro Pro Pro Gly Ala Cys Gly Ser Pro Ser Ala Pro Thr Pro Ser
                885                 890                 895

Ala Gly Val Ala Ala Thr Thr Ile Ala Gly Phe Gly His Phe His Lys
            900                 905                 910
```

```
Ala Leu Gly Gly Ser Leu Ser Ser Ser Asp Ser Pro Leu Leu Thr Pro
        915                 920                 925

Leu Gln Pro Gly Ala Arg Ser Pro Gln Ala Ala Gln Pro Ser Pro Ala
    930                 935                 940

Pro Pro Gly Ala Arg Gly Gly Leu Gly Leu Pro Glu His Phe Leu Pro
945                 950                 955                 960

Pro Pro Pro Ser Ser Arg Ser Pro Ser Ser Ser Pro Gly Gln Leu Gly
                965                 970                 975

Gln Pro Pro Gly Glu Leu Ser Leu Gly Leu Ala Thr Gly Pro Leu Ser
            980                 985                 990

Thr Pro Glu Thr Pro Pro Arg Gln Pro Glu Pro Pro Ser Leu Val Ala
        995                 1000                1005

Gly Ala Ser Gly Gly Ala Ser Pro Val Gly Phe Thr Pro Arg Gly Gly
   1010                 1015                1020

Leu Ser Pro Pro Gly His Ser Pro Gly Pro Pro Arg Thr Phe Pro Ser
1025                1030                1035                1040

Ala Pro Pro Arg Ala Ser Gly Ser His Gly Ser Leu Leu Leu Pro Pro
               1045                1050                1055

Ala Ser Ser Pro Pro Pro Pro Gln Val Pro Gln Arg Arg Gly Thr Pro
           1060                1065                1070

Pro Leu Thr Pro Gly Arg Leu Thr Gln Asp Leu Lys Leu Ile Ser Ala
       1075                1080                1085

Ser Gln Pro Ala Leu Pro Gln Asp Gly Ala Gln Thr Leu Arg Arg Ala
   1090                1095                1100

Ser Pro His Ser Ser Gly Glu Ser Met Ala Ala Phe Pro Leu Phe Pro
1105                1110                1115                1120

Arg Ala Gly Gly Gly Ser Gly Gly Ser Gly Ser Ser Gly Gly Leu Gly
               1125                1130                1135

Pro Pro Gly Arg Pro Tyr Gly Ala Ile Pro Gly Gln His Val Thr Leu
           1140                1145                1150

Pro Arg Lys Thr Ser Ser Gly Ser Leu Pro Pro Pro Leu Ser Leu Phe
       1155                1160                1165

Gly Ala Arg Ala Thr Ser Ser Gly Gly Pro Pro Leu Thr Ala Gly Pro
   1170                1175                1180

Gln Arg Glu Pro Gly Ala Arg Pro Glu Pro Val Arg Ser Lys Leu Pro
1185                1190                1195                1200

Ser Asn Leu


<210> SEQ ID NO 21
<211> LENGTH: 1175
<212> TYPE: PRT
<213> ORGANISM: Oryctolagus cuniculus

<400> SEQUENCE: 21

Met Asp Lys Leu Pro Pro Ser Met Arg Lys Arg Leu Tyr Ser Leu Pro
  1               5                  10                  15

Gln Gln Val Gly Ala Lys Ala Trp Ile Met Asp Glu Glu Glu Asp Ala
             20                  25                  30

Glu Glu Glu Gly Ala Gly Gly Arg Gln Asp Pro Arg Arg Arg Ser Ile
         35                  40                  45

Arg Leu Arg Pro Leu Pro Ser Pro Ser Pro Ser Pro Ser Ala Ala Ala
     50                  55                  60

Ala Ala Ala Gly Gly Ala Glu Ser Arg Gly Ala Ala Leu Gly Gly Ala
 65                  70                  75                  80

Ala Asp Gly Glu Gly Pro Ala Arg Gly Ala Ala Lys Ser Ser Thr Asn
```

```
                85                  90                  95

Gly Asp Cys Arg Arg Phe Arg Gly Ser Leu Ala Ser Leu Gly Ser Arg
            100                 105                 110

Gly Gly Gly Gly Gly Gly Gly Ser Thr Gly Gly Gly Ser His Gly His
        115                 120                 125

Leu His Asp Ser Ala Glu Glu Arg Arg Leu Ile Ala Glu Gly Asp Ala
    130                 135                 140

Ser Pro Gly Glu Asp Arg Thr Pro Pro Gly Leu Ala Ala Glu Pro Glu
145                 150                 155                 160

Arg Pro Gly Ala Pro Ala Pro Pro Ala Ala Ser Pro Pro Gln Val Pro
                165                 170                 175

Ser Ser Cys Gly Glu Gln Arg Pro Ala Asp Ala Ala Val Lys Val Glu
            180                 185                 190

Gly Gly Ala Ala Ala Gly Asp Gln Ile Leu Pro Glu Ala Glu Ala Arg
        195                 200                 205

Leu Gly Gln Ala Gly Phe Met Gln Arg Gln Phe Gly Ala Met Leu Gln
    210                 215                 220

Pro Gly Val Asn Lys Phe Ser Leu Arg Met Phe Gly Ser Gln Lys Ala
225                 230                 235                 240

Val Glu Arg Glu Gln Glu Arg Val Lys Ser Ala Gly Phe Trp Ile Ile
                245                 250                 255

His Pro Tyr Ser Asp Phe Arg Phe Tyr Trp Asp Leu Thr Met Leu Leu
            260                 265                 270

Leu Met Val Gly Asn Leu Ile Ile Ile Pro Val Gly Ile Thr Phe Phe
        275                 280                 285

Lys Asp Glu Asn Thr Thr Pro Trp Ile Val Phe Asn Val Val Ser Asp
    290                 295                 300

Thr Phe Phe Leu Ile Asp Leu Val Leu Asn Phe Arg Thr Gly Ile Val
305                 310                 315                 320

Val Glu Asp Asn Thr Asp Ile Ile Leu Asp Pro Arg Arg Ile Lys Met
                325                 330                 335

Lys Tyr Leu Lys Ser Trp Phe Val Val Asp Phe Val Ser Ser Ile Pro
            340                 345                 350

Val Asp Tyr Ile Phe Leu Ile Val Glu Thr Arg Ile Asp Ser Glu Val
        355                 360                 365

Tyr Lys Thr Ala Arg Ala Leu Arg Ile Val Arg Phe Thr Lys Ile Leu
    370                 375                 380

Ser Leu Leu Arg Leu Leu Arg Leu Ser Arg Leu Ile Arg Tyr Ile His
385                 390                 395                 400

Gln Trp Glu Glu Ile Phe His Met Thr Tyr Asp Leu Ala Ser Ala Val
                405                 410                 415

Val Arg Ile Val Asn Leu Ile Gly Met Met Leu Leu Leu Cys His Trp
            420                 425                 430

Asp Gly Cys Leu Gln Phe Leu Val Pro Met Leu Gln Asp Phe Pro Asp
        435                 440                 445

Asp Cys Trp Val Ser Leu Asn Asn Met Val Asn Asn Ser Trp Gly Lys
    450                 455                 460

Gln Tyr Ser Tyr Ala Leu Phe Lys Ala Met Ser His Met Leu Cys Ile
465                 470                 475                 480

Gly Tyr Gly Arg Gln Ala Pro Met Gly Met Ser Asp Val Trp Leu Thr
                485                 490                 495

Met Leu Ser Met Ile Val Gly Ala Thr Cys Tyr Ala Met Phe Ile Gly
            500                 505                 510
```

```
His Ala Thr Ala Leu Ile Gln Ser Leu Asp Ser Ser Arg Arg Gln Tyr
        515                 520                 525

Gln Glu Lys Tyr Lys Gln Val Glu Gln Tyr Met Ser Phe His Lys Leu
    530                 535                 540

Pro Pro Asp Thr Arg Gln Arg Ile His Asp Tyr Tyr Glu His Arg Tyr
545                 550                 555                 560

Gln Gly Lys Met Phe Asp Glu Glu Ser Ile Leu Gly Glu Leu Ser Glu
                565                 570                 575

Pro Leu Arg Glu Glu Ile Ile Asn Phe Asn Cys Arg Lys Leu Val Ala
            580                 585                 590

Ser Met Pro Leu Phe Ala Asn Ala Asp Pro Asn Phe Val Thr Ser Met
        595                 600                 605

Leu Thr Lys Leu Arg Phe Glu Val Phe Gln Pro Gly Asp Tyr Ile Ile
    610                 615                 620

Arg Glu Gly Thr Ile Gly Lys Lys Met Tyr Phe Ile Gln His Gly Val
625                 630                 635                 640

Val Ser Val Leu Thr Lys Gly Asn Lys Glu Thr Lys Leu Ala Asp Gly
                645                 650                 655

Ser Tyr Phe Gly Glu Ile Cys Leu Leu Thr Arg Gly Arg Arg Thr Ala
            660                 665                 670

Ser Val Arg Ala Asp Thr Tyr Cys Arg Leu Tyr Ser Leu Ser Val Asp
        675                 680                 685

Asn Phe Asn Glu Val Leu Glu Glu Tyr Pro Met Met Arg Arg Ala Phe
    690                 695                 700

Glu Thr Val Ala Leu Asp Arg Leu Asp Arg Ile Gly Lys Lys Asn Ser
705                 710                 715                 720

Ile Leu Leu His Lys Val Gln His Asp Leu Ser Ser Gly Val Ser Asn
                725                 730                 735

Tyr Gln Glu Asn Ala Ile Val Gln Arg Ile Val Gln His Asp Arg Glu
            740                 745                 750

Met Ala His Cys Ala Arg Arg Ala Gln Ala Thr Thr Pro Val Ala Pro
        755                 760                 765

Ala Ile Trp Thr Pro Leu Ile Gln Ala Pro Leu Gln Ala Ala Ala Ala
    770                 775                 780

Thr Thr Ser Val Ala Ile Ala Leu Thr His His Pro Arg Leu Pro Ala
785                 790                 795                 800

Ala Ile Phe Arg Pro Pro Pro Gly Pro Thr Thr Leu Gly Ser Leu Gly
                805                 810                 815

Ala Gly Gln Thr Pro Arg His Leu Arg Arg Leu Gln Ser Leu Ala Pro
            820                 825                 830

Ser Ala Pro Ser Pro Ala Ser Pro Ala Ser Ser Pro Ser Gln Pro Asp
        835                 840                 845

Thr Pro Ser Ser Ala Ser Leu His Val Gln Pro Leu Pro Gly Cys Ser
    850                 855                 860

Thr Pro Ala Gly Leu Gly Ser Leu Leu Pro Thr Ala Gly Ser Pro Pro
865                 870                 875                 880

Ala Pro Thr Pro Pro Thr Thr Ala Gly Ala Ala Gly Phe Ser His Phe
                885                 890                 895

His Arg Ala Leu Gly Gly Ser Leu Ser Ser Ser Asp Ser Pro Leu Leu
            900                 905                 910

Thr Pro Met Gln Ser Ala Ala Arg Ser Pro Gln Gln Pro Pro Pro Pro
        915                 920                 925

Pro Gly Ala Pro Ala Gly Leu Gly Leu Leu Glu His Phe Leu Pro Pro
    930                 935                 940
```

```
Pro Ala Arg Ser Pro Thr Ser Ser Pro Gly Gln Leu Gly Gln Pro Pro
945                 950                 955                 960

Gly Glu Leu Ser Pro Gly Leu Gly Ser Gly Pro Pro Gly Thr Pro Glu
                965                 970                 975

Thr Pro Pro Arg Gln Pro Glu Arg Leu Pro Phe Ala Ala Gly Ala Ser
            980                 985                 990

Ala Gly Ala Ser Pro Val Ala Phe Ser Pro Arg Gly Gly Pro Ser Pro
        995                 1000                1005

Pro Gly His Ser Pro Gly Thr Pro Arg Thr Phe Pro Ser Ala Pro Pro
   1010                 1015                1020

Arg Ala Ser Gly Ser His Gly Ser Leu Leu Leu Pro Pro Ala Ser Ser
1025                1030                1035                1040

Pro Pro Pro Pro Pro Pro Pro Pro Ala Pro Gln Arg Arg Ala Thr Pro
               1045                1050                1055

Pro Leu Ala Pro Gly Arg Leu Ser Gln Asp Leu Lys Leu Ile Ser Ala
           1060                1065                1070

Ser Gln Pro Ala Leu Pro Gln Asp Gly Ala Gln Thr Leu Arg Arg Ala
       1075                1080                1085

Ser Pro His Ser Ser Ser Gly Glu Ser Val Ala Ala Leu Pro Pro Phe
   1090                 1095                1100

Pro Arg Ala Pro Gly Arg Pro Pro Gly Ala Gly Pro Gly Gln His Val
1105                1110                1115                1120

Thr Leu Thr Leu Pro Arg Lys Ala Ser Ser Gly Ser Leu Pro Pro Pro
               1125                1130                1135

Leu Ser Leu Phe Gly Pro Arg Ala Ala Pro Ala Gly Gly Pro Arg Leu
           1140                1145                1150

Thr Ala Ala Pro Gln Arg Glu Pro Gly Ala Lys Ser Glu Pro Val Arg
       1155                1160                1165

Ser Lys Leu Pro Ser Asn Leu
   1170                 1175


<210> SEQ ID NO 22
<211> LENGTH: 124
<212> TYPE: PRT
<213> ORGANISM: Canis familiaris

<400> SEQUENCE: 22

Asp Glu Asp Ser Ile Leu Gly Glu Leu Ser Glu Pro Leu Arg Glu Glu
  1               5                  10                  15

Ile Ile Asn Phe Asn Cys Arg Lys Leu Val Ala Ser Met Pro Leu Phe
             20                  25                  30

Ala Asn Ala Asp Pro Asn Phe Val Thr Ser Met Leu Thr Lys Leu Arg
         35                  40                  45

Phe Glu Val Phe Gln Pro Gly Asp Tyr Ile Ile Arg Glu Gly Thr Ile
     50                  55                  60

Gly Lys Lys Met Tyr Phe Ile Gln His Gly Val Val Ser Val Leu Thr
 65                  70                  75                  80

Lys Gly Asn Lys Glu Thr Lys Leu Ala Asp Gly Ser Tyr Phe Gly Glu
                 85                  90                  95

Ile Cys Leu Leu Thr Arg Gly Arg Arg Thr Ala Ser Val Arg Ala Asp
            100                 105                 110

Thr Tyr Cys Arg Leu Tyr Ser Leu Ser Val Asp Asn
        115                 120


<210> SEQ ID NO 23
```

<211> LENGTH: 1528
<212> TYPE: DNA
<213> ORGANISM: Homo sapiens

<400> SEQUENCE: 23
gaggcagttc acctccatgc tgcagcccgg ggtcaacaaa ttctccctcc gcatgtttgg 60
gagccagaag gcggtggaaa aggagcagga aagggttaaa actgcaggct tctggattat 120
ccacccttac agtgatttca ggttttactg ggatttaata atgcttataa tgatggttgg 180
aaatctagtc atcataccag ttggaatcac attctttaca gagcaaacaa caacaccatg 240
gattattttc aatgtggcat cagatacagt tttcctattg gacctgatca tgaattttag 300
gactgggact gtcaatgaag acagttctga aatcatcctg gaccccaaag tgatcaagat 360
gaattattta aaaagctggt ctgtggttga cttcatctca tccatcccag tggattatat 420
ctttcttatt gtagaaaaag gaatggattc tgaagtttac aagacagcca gggcacttcg 480
cattgtgagg tttacaaaaa ttctcagtct cttgcgttta ttacgacttt caaggttaat 540
tagatacata catcaatggg aagagatatt ccacatgaca tatgatctcg ccagtgcagt 600
ggtgagaatt tttaatctca tcggcatgat gctgctcctg tgccactggg atggttgtct 660
tcagttctta gtaccactac tgcaggactt cccaccagat tgctgggtgt ctttaaatga 720
aatggttaat gattcttggg gaaagcagta ttcatacgca ctcttcaaag ctatgagtca 780
catgctgtgc attgggtatg gagcccaagc cccagtcagc atgtctgacc tctggattac 840
catgctgagc atgatcgtcg ggccacctg ctatgccatg tttgtcggcc atgccaccgc 900
tttaatccag tctctggatt cttcgaggcg gcagtatcaa gagaagtata agcaagtgga 960
acaatacatg tcattccata agttaccagc tgatatgcgt cagaagatac atgattacta 1020
tgaacacaga taccaaggca aaatctttga tgaggaaaat attctcaatg aactcaatga 1080
tcctctgaga ggggagatag tcaacttcaa ctgtcggaaa ctggtggcta caatgccttt 1140
atttgctaat gcggatccta attttgtgac tgccatgctg agcaagttga gatttgaggt 1200
gtttcaacct ggagattata tcgtacgaga aggagccgtg ggtaaaaaaa tgtatttcat 1260
tcaacacggt gttgctggtg tcattacaaa atccagtaaa gaaatgaagc tgacagatgg 1320
ctcttacttt ggagagattt gcctgctgac caaaggacgt cgtactgcca gtgttcgagc 1380
tgatacatat tgtcgtcttt actcactttc cgtggacaat ttcaacgagg tcccggagga 1440
atatccaatg atgaggagag cctttgagac agttgccatt gaccgactag atcgaatagg 1500
aaagaaaaat tcaattcttc tgcaaaag 1528

<210> SEQ ID NO 24
<211> LENGTH: 1528
<212> TYPE: DNA
<213> ORGANISM: Homo sapiens

<400> SEQUENCE: 24
gcgccagttc ggcgcgctcc tgcagccggg cgtcaacaag ttctcgctgc ggatgttcgg 60
cagccagaag gccgtggagc gcgagcagga gcgcgtcaag tcggcggggg cctggatcat 120
ccacccgtac agcgacttca ggttctactg ggacttcacc atgctgctgt tcatggtggg 180
aaacctcatc atcatcccag tgggcatcac cttcttcaag gatgagacca ctgccccgtg 240
gatcgtgttc aacgtggtct cggacacctt cttcctcatg gacctggtgt tgaacttccg 300
caccggcatt gtgatcgagg acaacacgga gatcatcctg gaccccgaga agatcaagaa 360
gaagtatctg cgcacgtggt tcgtggtgga cttcgtgtcc tccatccccg tggactacat 420

```
cttccttatt gtggagaagg gcattgactc cgaggtctac aagacggcac gcgccctgcg    480

catcgtgcgc ttcaccaaga tcctcagcct cctgcggctg ctgcgcctct cacgcctgat    540

ccgctacatc catcagtggg aggagatctt ccacatgacc tatgacctgg ccagcgcggt    600

gatgaggatc tgcaatctca tcagcatgat gctgctgctc tgccactggg acggctgcct    660

gcagttcctg gtgcctatgc tgcaggactt cccgcgcaac tgctgggtgt ccatcaatgg    720

catggtgaac cactcgtgga gtgaactgta ctccttcgca ctcttcaagg ccatgagcca    780

catgctgtgc atcgggtacg gccggcaggc gcccgagagc atgacggaca tctggctgac    840

catgctcagc atgattgtgg gtgccacctg ctacgccatg ttcatcggcc acgccactgc    900

cctcatccag tcgctggact cctcgcggcg ccagtaccag gagaagtaca agcaggtgga    960

gcagtacatg tccttccaca agctgccagc tgacttccgc cagaagatcc acgactacta   1020

tgagcaccgt taccagggca agatgtttga cgaggacagc atcctgggcg agctcaacgg   1080

gcccctgcgg gaggagatcg tcaacttcaa ctgccggaag ctggtggcct ccatgccgct   1140

gttcgccaac gccgacccca acttcgtcac ggccatgctg accaagctca agttcgaggt   1200

cttccagccg ggtgactaca tcatccgcga aggcaccatc gggaagaaga tgtacttcat   1260

ccagcacggc gtggtcagcg tgctcactaa gggcaacaag gagatgaagc tgtccgatgg   1320

ctcctacttc ggggagatct gcctgctcac ccggggccgc cgcacggcga gcgtgcgggc   1380

cgacacctac tgccgcctct attcgctgag cgtggacaac ttcaacgagg tgctggagga   1440

gtaccccatg atgcggcgcg ccttcgagac ggtggccatc gaccgcctgg accgcatcgg   1500

caagaagaat tccatcctcc tgcacaag                                      1528
```

```
<210> SEQ ID NO 25
<211> LENGTH: 1520
<212> TYPE: DNA
<213> ORGANISM: Homo sapiens

<400> SEQUENCE: 25

gcgccagttc ggggccatgc tccaacccgg ggtcaacaaa ttctccctaa ggatgttcgg     60

cagccagaaa gccgtggagc gcgaacagga gagggtcaag tcggccggat tttggattat    120

ccacccctac agtgacttca gattttactg ggacctgacc atgctgctgc tgatggtggg    180

aaacctgatt atcattcctg tgggcatcac cttcttcaag gatgagaaca ccacaccctg    240

gattgtcttc aatgtggtgt cagacacatt cttcctcatc gacttggtcc tcaacttccg    300

cacagggatc gtggtggagg acaacacaga gatcatcctg gacccgcagc ggattaaaat    360

gaagtacctg aaaagctggt tcatggtaga tttcatttcc tccatccccg tggactacat    420

cttcctcatt gtggagacac gcatcgactc ggaggtctac aagactgccc gggccctgcg    480

cattgtccgc ttcacgaaga tcctcagcct cttacgcctg ttacgcctct cccgcctcat    540

tcgatatatt caccagtggg aagagatctt ccacatgacc tacgacctgg ccagcgccgt    600

ggtgcgcatc gtgaacctca tcggcatgat gctcctgctc tgccactggg acggctgcct    660

gcagttcctg gtacccatgc tacaggactt ccctgacgac tgctgggtgt ccatcaacaa    720

catggtgaac aactcctggg ggaagcagta ctcctacgcg ctcttcaagg ccatgagcca    780

catgctgtgc atcggctacg ggcggcaggc gcccgtgggc atgtccgacg tctggctcac    840

catgctcagc atgatcgtgg gtgccacctg ctacgccatg ttcattggcc acgccactgc    900

cctcatccag tccctggact cctcccggcg ccagtaccag gaaaagtaca agcaggtgga    960

gcagtacatg tcctttcaca agctcccgcc cgacacccgg cagcgcatcc acgactacta   1020
```

```
cgagcaccgc taccagggca agatgttcga cgaggagagc atcctgggcg agctaagcga   1080
gcccctgcgg gaggagatca tcaactttaa ctgtcggaag ctggtggcct ccatgccact   1140
gtttgccaat gcggaccccca acttcgtgac gtccatgctg accaagctgc gtttcgaggt  1200
cttccagcct ggggactaca tcatccggga aggcaccatt ggcaagaaga tgtacttcat   1260
ccagcatggc gtggtcagcg tgctcaccaa gggcaacaag gagaccaagc tggccgacgg   1320
ctcctacttt ggagagatct gcctgctgac ccggggccgg cgcacagcca gcgtgagggc   1380
cgacacctac tgccgcctct actcgctgag cgtggacaac ttcaatgagg tgctggagga   1440
gtaccccatg atgcgaaggg ccttcgagac cgtggcgctg gaccgcctgg accgcattgg   1500
caagaagaac tccatcctcc                                               1520
```

<210> SEQ ID NO 26
<211> LENGTH: 1527
<212> TYPE: DNA
<213> ORGANISM: Mus musculus

<400> SEQUENCE: 26

```
gaggcagttc acctccatgc tgcagcctgg ggtcaacaaa ttctccctcc gcatgtttgg     60
gagccagaag gcggtggaga aggagcagga aagggttaaa actgcaggct tctggattat    120
ccatccgtac agtgacttca ggttttattg ggatttaatc atgcttataa tgatggttgg    180
aaatttggtc atcataccag ttggaatcac gttcttcaca gagcagacga caacaccgtg    240
gattattttc aacgtggcat ccgatactgt tttcctgttg gacttaatca tgaattttag    300
gactgggact gtcaatgaag acagctcgga aatcatcctg gaccctaaag tgatcaagat    360
gaattattta aaaagctggt ttgtggtgga cttcatctca tcgatcccgg tggattatat    420
ctttctcatt gtagagaaag ggatggactc agaagtttac aagacagcca gagcacttcg    480
tatcgtgagg tttacaaaaa ttctcagtct cttgcggtta ttacgccttt caaggttaat    540
cagatacata caccagtggg aagagatatt ccacatgacc tatgacctcg ccagtgctgt    600
ggtgaggatc ttcaacctca ttggcatgat gctgcttctg tgccactggg atggctgtct    660
tcagttcctg gttcccctgc tgcaggactt cccaccagat tgctgggttt ctctgaatga    720
aatggttaat gattcctggg gaaaacaata ttcctacgca ctcttcaaag ctatgagtca    780
catgctgtgc attggttatg gcgcccaagc ccctgtcagc atgtctgacc tctggattac    840
catgctgagc atgattgtgg gcgccacctg ctacgcaatg tttgttggcc atgccacagc    900
tttgatccag tctttggact cttcaaggag gcagtatcaa gagaagtata agcaagtaga    960
gcaatacatg tcattccaca agttaccagc tgacatgcgc cagaagatac atgattacta   1020
tgagcaccga taccaaggca agatcttcga tgaagaaaat attctcagtg agcttaatga   1080
tcctctgaga gaggaaatag tcaacttcaa ctgccggaaa ctggtggcta ctatgcctct   1140
tttgctaac gccgatccca atttcgtgac ggccatgctg agcaagctga gatttgaggt    1200
gttccagccc ggagactata tcattcgaga aggagctgtg ggaagaaaa tgtatttcat    1260
ccagcacggt gttgctggcg ttatcaccaa gtccagtaaa gaaatgaagc tgacagatgg   1320
ctcttacttc ggagagatat gcctgctgac caagggccgg cgcactgcca gtgtccgagc   1380
tgatacctac tgtcgtcttt actccctttc ggtggacaat ttcaatgagg tcttggagga   1440
atatccaatg atgagaagag cctttgagac agttgctatt gaccgactcg atcggatagg   1500
caagaaaaac tctattctcc tgcagaa                                       1527
```

<210> SEQ ID NO 27

<211> LENGTH: 1527
<212> TYPE: DNA
<213> ORGANISM: Mus musculus

<400> SEQUENCE: 27

```
gcgccaattc ggggcgcttc tgcagcccgg cgtcaacaag ttctccctgc ggatgttcgg     60

cagccagaag gccgtggagc gcgagcagga acgcgtgaag tcggcggggg cctggatcat    120

ccacccctac agcgacttca ggttctactg ggacttcacc atgctgttgt tcatggtggg    180

aaatctcatt atcattcccg tgggcatcac tttcttcaag gacgagacca ccgcgccctg    240

gatcgtcttc aacgtggtct cggacacttt cttcctcatg gacttggtgt tgaacttccg    300

caccggcatt gttattgagg acaacacgga gatcatcctg gaccccgaga agataaagaa    360

gaagtacttg cgtacgtggt tcgtggtgga cttcgtgtca tccatcccgg tggactacat    420

cttcctcata gtggagaagg gaatcgactc cgaggtctac aagacagcgc gtgctctgcg    480

catcgtgcgc ttcaccaaga tcctcagtct gctgcggctg ctgcggctat cacggctcat    540

ccgatatatc caccagtggg aagagatttt ccacatgacc tacgacctgg caagtgcagt    600

gatgcgcatc tgtaacctga tcagcatgat gctactgctc tgccactggg acggttgcct    660

gcagttcctg gtgcccatgc tgcaagactt ccccagcgac tgctgggtgt ccatcaacaa    720

catggtgaac cactcgtgga gcgagctcta ctcgttcgcg ctcttcaagg ccatgagcca    780

catgctgtgc atcggctacg ggcggcaggc gcccgagagc atgacagaca tctggctgac    840

catgctcagc atgatcgtag gcgccacctg ctatgccatg ttcattgggc acgccactgc    900

gctcatccag tccctggatt cgtcacggcg ccaataccag gagaagtaca agcaagtaga    960

gcaatacatg tccttccaca aactgcccgc tgacttccgc cagaagatcc acgattacta   1020

tgaacaccgg taccaaggga agatgtttga tgaggacagc atccttgggg aactcaacgg   1080

gccactgcgt gaggagattg tgaacttcaa ctgccggaag ctggtggctt ccatgccgct   1140

gtttgccaat gcagacccca acttcgtcac agccatgctg acaaagctca aatttgaggt   1200

cttccagcct ggagattaca tcatccgaga ggggaccatc gggaagaaga tgtacttcat   1260

ccagcatggg gtggtgagcg tgctcaccaa gggcaacaag gagatgaagc tgtcggatgg   1320

ctcctatttc ggggagatct gcttgctcac gaggggccgg cgtacggcca gcgtgcgagc   1380

tgacacctac tgtcgcctct actcactgag tgtggacaat ttcaacgagg tgctggagga   1440

ataccccatg atgcggcgtg cctttgagac tgtggctatt gaccggctag atcgcatagg   1500

caagaagaac tccatcttgc tgcacaa                                        1527
```

<210> SEQ ID NO 28
<211> LENGTH: 1547
<212> TYPE: DNA
<213> ORGANISM: Mus musculus

<400> SEQUENCE: 28

```
gcgcctgggc cagagcggct tcatgcagcg ccagttcggt gccatgctgc aacctggggt     60

caacaaattc tccctaagga tgttcggcag ccagaaagcg gtggagcgcg agcaggagag    120

ggttaagtca gcagggtttt ggattatcca cccctacagt gacttcagat tttactggga    180

cctgacgatg ctgttgctga tggtggggaa tctgatcatc atacccgtgg gcatcacctt    240

cttcaaggat gagaacacca caccctggat cgtcttcaat gtggtgtcag acacattctt    300

cctcattgac ttggtcctca acttccgcac ggggatcgtg gtggaggaca acacagaaat    360

catccttgac ccgcagagga tcaagatgaa gtacctgaaa agctggtttg tggtagattt    420
```

-continued

```
catctcctcc atccctgtcg actacatctt ccttatagtg gagactcgca ttgactcgga    480
ggtctacaaa accgctaggg ctctgcgcat tgtccgtttc actaagatcc tcagcctcct    540
gcgcctcttg aggctttccc gcctcattcg atacattcat cagtgggaag agatcttcca    600
catgacctat gacctggcca gcgccgtggt acgcatcgtg aacctcattg gcatgatgct    660
tctgctgtgt cactgggatg gctgcctgca gttcctagtg cccatgctgc aggacttccc    720
ccatgactgc tgggtgtcca tcaatggcat ggtgaataac tcctggggga agcagtattc    780
ctacgccctc ttcaaggcca tgagccacat gctgtgcatt gggtatggac ggcaggcacc    840
cgtaggcatg tctgacgtct ggctcaccat gctcagcatg atcgtggggg ccacctgcta    900
tgccatgttc atcggccacg ccactgccct catccagtcg ctagactcct cccggcgcca    960
gtaccaggag aagtataaac aggtggagca gtacatgtcc ttccacaagc tcccgcctga   1020
cacccgacag cgcatccatg actactatga acaccgctac caaggcaaga tgtttgatga   1080
ggaaagcatc ctgggtgagc tgagtgagcc acttcgagag gagatcatca actttaactg   1140
ccgaaagctg gtggcatcca tgccactgtt tgccaacgca gatcccaact ttgtgacatc   1200
catgctgacc aagttgcgtt tcgaggtctt ccagcctggg gattacatca tccgcgaagg   1260
caccatcggc aagaagatgt actttatcca gcacggcgtg gtcagcgtgc tcactaaggg   1320
caacaaagag accaagctgg ctgatggctc ctattttgga gagatctgct tgctgacccg   1380
gggtcggcgc acagccagcg tcagagcgga tacttattgc cgcctctact cactgagcgt   1440
ggacaacttc aatgaggtgc tggaggagta tcccatgatg cggagggcct tcgagacggt   1500
tgcgctggac cgcctggacc gcataggcaa gaagaactcc atcctcc                 1547
```

BIOLOGICAL BYPASS BRIDGE WITH SODIUM CHANNELS, CALCIUM CHANNELS AND/OR POTASSIUM CHANNELS TO COMPENSATE FOR CONDUCTION BLOCK IN THE HEART

This application claims the benefit of each of U.S. Provisional Application Nos. 60/704,210, filed Jul. 29, 2005; 60/701,312, filed Jul. 21, 2005; and 60/781,723, filed Mar. 14, 2006, the entire contents of each of which is incorporated herein by reference.

This invention was made with government support under NIH Grant No. HL-28958 awarded by the National Institutes of Health. The government has certain rights in the invention.

Throughout this application, various publications are referenced in parentheses by author name and date, patent number, patent application or publication number. Full citations for these publications may be found at the end of the specification immediately preceding the claims. The disclosures of these publications in their entireties are hereby incorporated by reference into this application in order to more fully describe the state of the art to those skilled therein as of the date of the invention described and claimed herein. However, the citation of a reference herein should not be construed as an acknowledgement that such reference is prior art to the present invention.

FIELD OF THE INVENTION

The present invention relates to a bypass bridge comprising a tract of gap junction-coupled cells that functionally express a sodium channel, the two ends of the tract being attachable to two selected sites in a heart so as to allow the conduction of a pacemaker and/or pacemaker and/or electrical signal/current across the tract between the two sites.

BACKGROUND OF THE INVENTION

Electronic pacemakers are lifesaving devices that provide a regular heartbeat in settings where the sinoatrial node, atrioventricular conduction, or both, have failed. Thus, one of the major indications for electronic pacemaker therapy is high degree heart block, such that a normally functioning sinus node impulse cannot propagate to the ventricle. The result is ventricular arrest and/or fibrillation, and death.

Malfunction or loss of pacemaker cells can occur due to disease or aging. For example, acute myocardial infarction (MI) kills millions of people each year and generally induces in survivors marked reductions in myocyte number and cardiac pump function. Adult cardiac myocytes divide only rarely, and the usual responses to myocyte cell loss include compensatory hypertrophy and/or congestive heart failure, a disease with a significant annual mortality. There have been recent reports of the delivery of bone marrow-derived and/or circulating human mesenchymal stem cells (hMSCs) to the hearts of post-myocardial infarct patients resulting in some improvement of mechanical performance (Strauer et al., 2002; Perin et al., 2003) in the absence of overt toxicity. The presumption in these and other animal studies (Orlic et al., 2001) is that the hMSCs integrate into the cardiac syncytium and then differentiate into new heart cells restoring mechanical function.

An alternative application of cell therapy, described herein, involves growing cells such as hMSCs into a bypass bridge comprising a tract of gap junction-coupled cells that can be used to conduct pacemaker and/or electrical current/signals across a region of the heart exhibiting impaired electrical conduction.

SUMMARY OF THE INVENTION

The invention disclosed herein provides a bypass bridge comprising a tract of gap junction-coupled cells having a first end and a second end, both ends capable of being attached to two selected sites in a heart so as to allow the conduction of a pacemaker and/or electrical signal/current across the tract between the two sites, wherein the cells functionally express a sodium channel. In certain embodiments of the bypass bridge, cells in the tract further functionally express a pacemaker ion channel which induces a pacemaker current so as to induce a pacemaker current in the cells. In preferred embodiments, the first end of the tract of cells is capable of being attached to the atrium and the second end is capable of being attached to the ventricle, so as to form an atrioventricular (AV) bridge that allows conduction of a pacemaker and/or electrical signal/current across the tract from the atrium to the ventricle.

The invention also provides a method of making a bypass bridge for implantation in a heart comprising (a) transfecting a cell with, and functionally expressing therein, a nucleic acid encoding a sodium channel and optionally a nucleic acid encoding a pacemaker ion channel, and (b) growing the transfected cell into a tract of cells having a first and a second end capable of being attached to two selected sites in the heart, wherein the cells are physically interconnected via electrically conductive gap junctions.

The invention further provides a method of implanting a bypass bridge in a heart comprising (a) making a bypass bridge by any of the methods disclosed herein, (b) selecting a first and a second site in the heart, and (c) attaching the first end of the tract to the first site and the second end of the tract to the second site, so as to thereby implant a bypass bridge in the heart that allows the conduction of a pacemaker and/or electrical signal/current across the tract between the two sites.

The present invention also provides a method of treating a disorder associated with an impaired conduction in a subject's heart comprising (a) transfecting a cell with a nucleic acid encoding a sodium channel, wherein the cell functionally expresses the sodium channel, (b) growing the transfected cell into a tract of cells having a first end and a second end, wherein the cells are physically interconnected via electrically conductive gap junctions, (c) selecting a first site and a second site in the heart between which sites conduction is impaired, and (d) attaching the first end of the tract to the first site and the second end of the tract to the second site, so as to allow the conduction of a pacemaker and/or electrical signal/current across the tract between the two sites and thereby treat the subject.

This invention further provides a method of treating a disorder associated with an impaired conduction and impaired sinus node activity in a subject's heart comprising (a) transfecting a cell with at least one nucleic acid encoding a sodium channel and a pacemaker ion channel, wherein the cell functionally expresses the sodium channel and the pacemaker ion channel, (b) growing the transfected cell into a tract of cells having a first end and a second end, wherein the cells are physically interconnected via electrically conductive gap junctions, (c) selecting a first site in the left atrium of the heart and a second site, between which sites conduction is impaired, and (d) attaching the first end of the tract to the first site and the second end of the tract to the second site, so as to allow the propagation of a pacemaker and/or electrical signal/ current generated by the sinus node and/or tract of cells between the two sites and thereby treat the subject.

BRIEF DESCRIPTION OF THE FIGURES

FIG. 1. Alignment of mouse and human HCN2 polypeptide sequences. The mouse and human HCN2 polypeptide sequences are aligned for maximum correspondence. The amino acid sequences of mHCN2 and hHCN2 are set forth in SEQ ID NO: 14 and SEQ ID NO: 16, respectively.

FIG. 2. Amino acid sequence of the human HCN212 chimeric channel. The shaded N-terminal portion of the sequence is derived from hHCN2; the underlined intramembranous portion from hHCN1; and the C-terminal portion (without shading or underline) from hHCN2. The amino acid sequence of the hHCN212 chimeric channel is set forth in SEQ ID NO: 2. This 889-amino acid long chimeric hHCN212 sequence shows 91.2% identity with the 863-amino acid long mHCN212 sequence in 893 residues overlap when aligned for maximum correspondence.

FIG. 3. Amino acid sequence of the mouse HCN212 chimeric channel. The shaded N-terminal portion of the sequence is derived from mouse HCN2; the underlined intramembranous portion from mouse HCN1; and the C-terminal portion (without shading or underline) from mouse HCN2. The amino acid sequence of the mouse HCN212 chimeric channel is set forth in SEQ ID NO: 6. This 863-amino acid long chimeric mHCN212 sequence shows 91.2% identity with the 889-amino acid long hHCN212 sequence in 893 residues overlap when aligned for maximum correspondence.

FIG. 8. Inactivation properties of a sodium channel suitable for incorporation into a cardiac bypass bridge. The inactivation properties of the SKM-1 sodium channel measured in *Xenopus* oocytes are shown. Left, The holding potential ranged from −100 mV to −55 mV and the test potential was +30 mV. Right, averaged inactivation curves for 11 oocytes.

FIG. 9. I-V relationship of a sodium channel suitable for incorporation into a cardiac bypass bridge. Shown here is I-V relationship for the SKM-1 channel recorded in *Xenopus* oocytes. Left, Raw data recorded from a holding potential of −80 mV to potentials between −70 mV and +50 mV in 10 mV increments. Right, Peak inward I-V relationship.

DETAILED DESCRIPTION OF THE INVENTION

Figure 4:
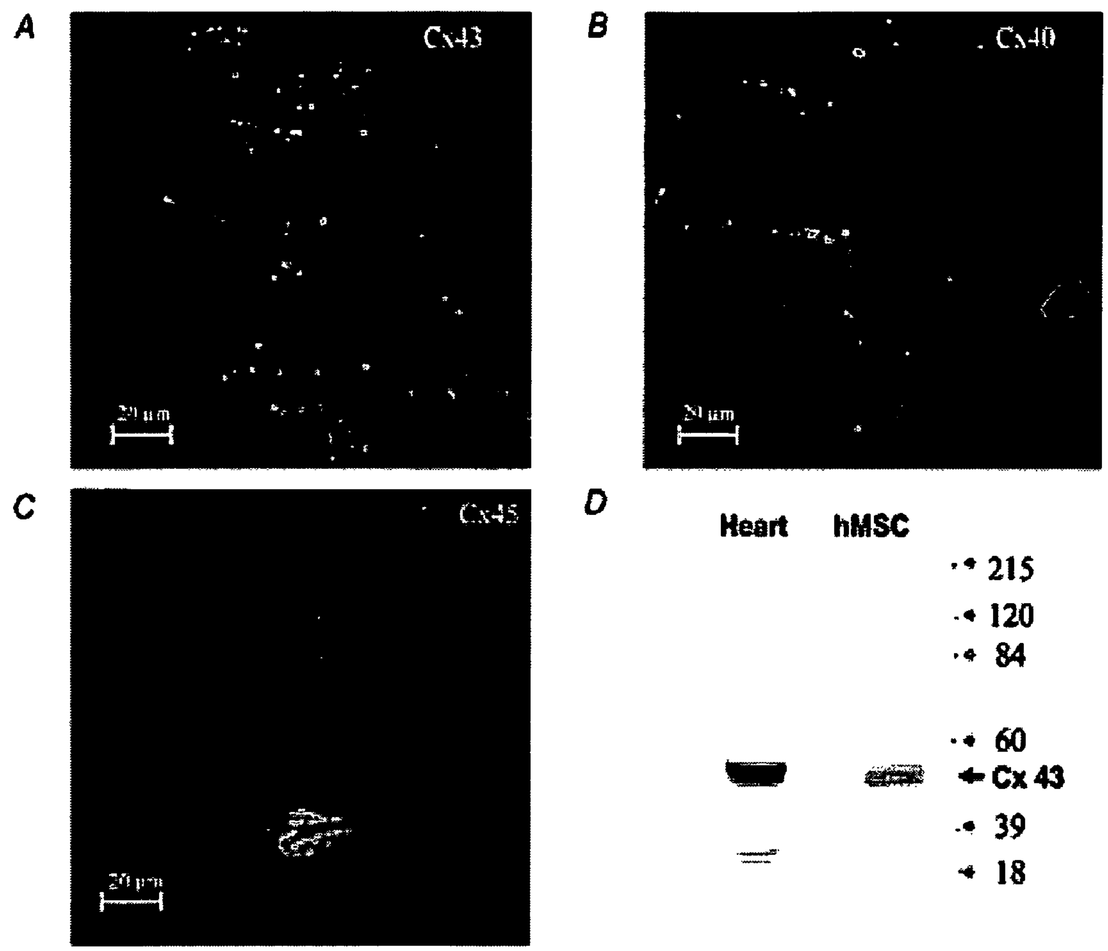
FIG. 4. Identification of connexins in gap junctions of human mesenchymal stem cells (hMSCs). Immunostaining of Cx43 (A), Cx40 (B) and Cx45 (C). D, Immunoblot analysis of Cx43 in canine ventricle myocytes and hMSCs. Whole cell lysates (120 μg) from ventricle cells or hMSCs were resolved by SDS, transferred to membranes, and blotted with Cx43 antibodies. Molecular weight markers are indicated.

The present invention provides a bypass bridge comprising a tract of gap junction-coupled cells having a first end and a second end, both ends capable of being attached to two selected sites in a heart so as to allow the conduction of a pacemaker and/or electrical signal/current across the tract between the two sites, wherein the cells functionally express a sodium channel. In certain embodiments of the bypass bridge, cells in the tract further functionally express a pacemaker ion channel which induces a pacemaker current so as to induce a pacemaker current in the cells. In preferred embodiments, the first end of the tract of cells is capable of being attached to the atrium and the second end is capable of being attached to the ventricle, so as to form an atrioventricular ("AV") bridge that allows conduction of a pacemaker and/or electrical signal/current across the tract from the atrium to the ventricle and thereby stimulate contraction of the ventricle.

The invention also provides a bypass bridge comprising a tract of gap junction-coupled cells having a first end and a second end, both ends capable of being attached to two selected sites in a heart so as to allow the conduction of a pacemaker and/or electrical signal/current across the tract between the two sites, wherein the cells functionally express a potassium channel or calcium channel instead of a sodium channel. The embodiments disclosed herein for the bypass bridge expressing a sodium channel are equally applicable to the bypass bridge expressing a potassium or calcium channel.

Exemplary cells that may be used for growing the tract include, but are not limited to, stem cells, cardiomyocytes, fibroblasts or skeletal muscle cells engineered to express at least one cardiac connexin, or endothelial cells. In preferred embodiments, the stem cells are adult mesenchymal stem cells (MSCs) or embryonic stem cells (ESCs), wherein said stem cells are substantially incapable of differentiation. In various embodiments, the MSCs are autologous, allogeneic or heterogenic relative to the subject into whose heart the bypass bridge is to be introduced, and the subject is a human being. As used herein, a "subject" shall mean any animal or artificially modified animal. Animals include, but are not limited to, humans, non-human primates, dogs, cats, cows, horses, sheep, pigs, rabbits, ferrets, rodents such as mice, rats and guinea pigs, and birds such as chickens and turkeys. Artificially modified animals include, but are not limited to, SCID mice with human immune systems. In a preferred embodiment, the subject is a human.

In more preferred embodiments of the instant bypass bridge, the stem cells are human adult mesenchymal stem cells (hMSCs) or human embryonic stem cells (hESCs), wherein the stem cells are substantially incapable of differentiation. In other preferred embodiments, the hMSCs (a) express CD29, CD44, CD54, and HLA class I surface markers; and (b) do not express CD14, CD34, CD45, and HLA class II surface markers. In additional embodiments, the hMSCs have been passaged at least 9 times, preferably 9-12 times. In further embodiments, the cells further express at least one cardiac connexin. In still further embodiments, the at least one cardiac connexin is Cx43, Cx40, or Cx45.

Thus, the present invention is based on the use of cell therapy to construct in the heart a bypass tract incorporating functional sodium ion channels, and optionally pacemaker channels, and optionally or alternatively potassium or calcium channels. The bypass bridge can be used to conduct a pacemaker and/or electrical signal/current between any two sites in the heart between which there is impaired pacemaker and/or electrical conduction. For example, the bypass may be used as an AV bridge to take over or supplement the function of a diseased AV node. Human MSCs may be grown in culture on a non-bioreactive matrix into a strip or tract of cells containing two ends. Once growth is complete, one end of the tract may be attached, e.g., by sutures, to a first selected site in the heart such as an atrium, and the other end may attached to a second selected site such as a ventricle. In a bypass bridge used as an AV bridge, for example, pacemaker and/or electrical signals/current generated by the sinus node to activate the atria will propagate across the artificially constructed tract to excite the ventricle. In this way the normal sequence of atrioventricular activation will be maintained.

Human MSCs may be prepared in several ways including, but not limited to, the following:

1: In culture without incorporation of additional molecular determinants of conduction. Here the cells' own ability to form gap junctions that communicate pacemaker and/or electrical signals are used as a means to conduct an electrotonic wave from one site in the heart to another.

2: In culture following transfection of the cells, such as by electroporation or viral infection, to introduce a gene for at least one of the cardiac connexins Cx43, Cx40 or Cx45, to enhance formation of gap junctions and thereby facilitate cell-to-cell propagation of pacemaker/electrical signals.

3: In culture following transfection of the cells to introduce a nucleic acid encoding the alpha and the accessory subunits of an L-type calcium channel, thereby increasing the likelihood of not just electrotonic propagation of a wavefront, but its active propagation by an action potential.

4: In culture following transfection of the cells to introduce a nucleic acid encoding the alpha subunit, with or without the accessory subunits, of a sodium channel, thereby increasing the likelihood of not just electrotonic propagation or calcium-dependent propagation of a wavefront, but its active propagation by a sodium-dependent action potential.

5: In culture following transfection of the cells to introduce a nucleic acid encoding the calcium and/or sodium channel subunits as in 3 and/or 4, and a nucleic acid encoding an alpha subunit, with or without the accessory subunits of a potassium channel, thereby increasing the likelihood of not just active propagation by an action potential, but additional control of the initial resting potential and its voltage-time course of repolarization and refractoriness.

6: Combinations of steps 2 through 5.

The preparation of a bypass bridge from hMSCs thus prepared allows conduction of pacemaker and/or electrical signals/current between any two selected sites in the heart. In the case of an AV bridge, it will not only will facilitate propagation of signals from atrium to ventricle, but provides sufficient delay from atrial to ventricular contraction to maximize ventricular filling and emptying, thus mimicking the normal activation and contractile sequence of the heart. Moreover, the cells in the bypass bridge, preferably cells at one end of the tract, may also be further transfected with a nucleic acid encoding a pacemaker current channel, wherein said transfected cells express a pacemaker current. Increases or decreases in calcium current, sodium current, potassium current or pacemaker current ($I_f$) may be obtained by increasing or reducing in the cells the expression of the ion channels carrying these currents. These approaches, when used with gene therapy and stem cell technology to improve atrial impulse initiation in the setting of sinus node disease offer a completely physiologic system rather than its electronic replacement. Thus, in embodiments of this invention, the bypass bridge expresses one or more genes encoding a pacemaker ion channel and thereby induces a pacemaker current.

In different embodiments of this invention, the nucleic acid encoding the ion channel or connexin gene is introduced into the cell by infection with a viral vector, plasmid transformation, cosmid transformation, electroporation, lipofection, transfection using a chemical transfection reagent, heat shock transfection, or microinjection. In further embodiments, the viral vector is an adenoviral, an adeno-associated viral (AAV), or a retroviral vector.

In embodiments of the instant bypass bridge, the sodium channel is a SKM-1 channel. In certain embodiments, the SKM-1 channel comprises an alpha subunit. In other embodiments, the SKM-1 channel further comprises an accessory subunit. In additional embodiments, the tract further functionally expresses a potassium channel. The potassium channel may comprise a Kir2.1 or Kir2.2 alpha subunit, and may further comprise an accessory subunit. In different embodiments of the bypass bridge, cells in the tract further functionally express an L-type calcium channel, which may comprise an alpha subunit and accessory subunits. In further embodiments, cells in the tract forming the bypass bridge further functionally express one or more of at least one cardiac connexin, an alpha subunit with accessory subunits of an L-type calcium channel, or an alpha subunit with or without accessory subunits of the potassium channel, so as to change the voltage-time course of repolarization and/or refractoriness of the heart. In various embodiments, the at least one cardiac connexin is Cx43, Cx40, or Cx45.

In various embodiments of the bypass bridge that expresses a pacemaker ion channel, said pacemaker ion channel is at least one of (a) a hyperpolarization-activated, cyclic nucleotide-gated (HCN) ion channel or a mutant or chimera thereof, and (b) a MiRP1 beta subunit. The HCN channel may be any of HCN1, HCN2, HCN3 or HCN4. In embodiments of this invention, the pacemaker channels are engineered to operate at progressively slower rates, so as to equate to primary and subsidiary pacemakers similar to the sinus node and Purkinje system. In preferred embodiments, the pacemaker ion channel is expressed in cells in the first end of the tract. In more preferred embodiments, the cells expressing the pacemaker ion channel are located in a region extending 0.5 mm from the first end.

Hyperpolarization-activated cation currents, termed $I_f$, $I_h$, or $I_q$, were initially discovered in heart and nerve cells over 20 years ago (for review, see DiFrancesco, 1993; Pape, 1996). These currents, carried by $Na^+$ and $K^+$ ions, contribute to a wide range of physiological functions, including cardiac and neuronal pacemaker activity, the setting of resting potentials, input conductance and length constants, and dendritic integration (see Robinson and Siegelbaum, 2003; Biel et al., 2002). The hyperpolarization-activated, cyclic nucleotide-gated (HCN) family of ion channel subunits has been identified by molecular cloning (for review, see Clapham, 1998; Santoro and Tibbs, 1999; Biel et al., 2002), and when heterologously expressed, each of the four different HCN isoforms generates channels with the principal properties of native $I_f$, confirming that HCN channels are the molecular correlate of this current.

As used herein, a "HCN channel" shall mean a hyperpolarization-activated, cyclic nucleotide-gated ion channel responsible for the hyperpolarization-activated cation currents that are directly regulated by cAMP and contribute to pacemaker activity in heart and brain. There are four HCN isoforms: HCN1, HCN2, HCN3 and HCN4. All four isoforms are expressed in brain; HCN1, HCN2 and HCN4 are also prominently expressed in heart, with HCN4 and HCN1 predominating in sinoatrial node and HCN2 in the ventricular specialized conducting system. "mHCN" designates murine or mouse HCN; "hHCN" designates human HCN.

HCN channels, similar to voltage-gated $K^+$ (Kv) channels, have four subunits, each of which has six transmembrane segments, S1-S6: the positively charged S4 domain forms the major voltage sensor, whereas S5 and S6, together with the S5-S6 linker connecting the two, form the pore domain containing the ion permeation pathway and the gates that control the flow of ions (Larsson, 2002). Mutational studies on HCN channels indicate that mutations in the S4 voltage sensor, the S4-S5 linker implicated in the coupling of voltage sensing to pore opening and closing, the S5, S6 and S5-S6 linker which form the pore, the C-linker, and the C-terminal cyclic nucleotide binding domain (CNBD), may be particularly important in affecting HCN channel activity. In embodiments of the bypass bridge expressing a mutant HCN, said mutant HCN channel provides an improved characteristic, as compared to a wild-type HCN channel, selected from the group consisting of faster kinetics, more positive activation, increased expression, increased stability, preserved or enhanced cAMP responsiveness, and preserved or enhanced neurohumoral response. Mutant HCN channels for inducing pacemaker activity in cells is also described in U.S. Provisional Application Nos. 60/781,723 (filed Mar. 14, 2006) and 60/832,515, entitled "Chimeric HCN Channels," which is being filed concurrently with the subject application (Jul. 21, 2006). Mutant HCN channels are also discussed in U.S. application Ser. No. 10/342,506. The preceding applications are herein incorporated by reference in their entirety.

In certain embodiments of the present invention, the mutant HCN channel carries at least one mutation in S4 voltage sensor, the S4-S5 linker, S5, S6, the S5-S6 linker, and/or the C-linker, and the CNBD which mutations result in one or more of the above discussed improved characteristics. In other embodiments, the HCN mutant is E324A-HCN2, Y331A-HCN2, R339A-HCN2, or Y331A, E324A-HCN2. In preferred embodiments, the mutant HCN channel is E324A-HCN2.

In addition to the mutations noted above, many mutations in different HCN isoforms have been reported. These include R318Q, W323A, E324A, E324D, E324K, E324Q, F327A, T330A and Y331A, Y331D, Y331F, Y331K, D332A, M338A, R339A, R339C, R339D, R339E and R339Q in HCN2 made by Chen et al. (2001a) to investigate in greater detail the role of the E324, Y331 and R339 residues in voltage sensing and activation. Chen et al. (2001b) have also reported the R538E and R591E mutations in mHCN1; Tsang et al. (2004) have reported G231A and M232A in mHCN1; Vemana et al (2004) have reported R247C, T249C, K250C, I251C, L252C, S253C, L254C, L258C, R259C, L260C, S261C, C318S, S338C in mHCN2; Macri and Accili (2004) have reported S306Q, Y331D AND G404S in mHCN2; and Decher et al. (2004) have reported Y331A, Y331D, Y331S, R331FD, R339E, R339Q, I439A, S441A, S441T, D443A, D443C, D443E, D443K, D443N, D443R, R447A, R447D, R447E, R447Y, Y449A, Y449D, Y449F, Y449G, Y449W, Y453A, Y453D, Y453F, Y453L, Y453W, P466Q, P466V, Y476A, Y477A and Y481A in mHCN2. The entire contents of all of the above publications are incorporated herein by reference. Certain of the reported mutations listed above may confer, singly or in combination, beneficial characteristics on the HCN channel with regard to creating a biological pacemaker. The invention disclosed herein encompasses all mutations in HCN channels, singly or in combinations, which improve pacemaker activity of the channel such as by providing faster kinetics, more positive activation, increased expression and/or stability, preserved cyclic interval responsiveness, and/or preserved or enhanced neurohumoral response.

Mutations are identified herein by a designation with provides the single letter abbreviation of the amino acid residue that underwent mutation, the position of that residue within a polypeptide, and the single letter abbreviation of the amino acid residue to which the residue was mutated. Thus, for example, E324A identifies a mutant polypeptide in which the glutamate residue (E) at position 324 was mutated to alanine (A). Y331A, E324A-HCN2 indicates a mouse HCN2 having a double mutation, one in which tyrosine (Y) at position 331 was mutated to alanine (A), and the other in which the glutamate residue at position 324 was mutated to alanine.

In general terms, HCN polypeptides can be divided into three major domains: (1) a cytoplasmic amino terminal domain; (2) the membrane spanning domains and their linking regions; and (3) a cytoplasmic carboxy-terminal domain. The N-terminal domain does not appear to play a major role in channel activation (Biel et al., 2002). However, the membrane spanning domains with their linking regions play an important role in determining the kinetics of gating, whereas the CNBD is largely responsible for the ability of the channel to respond to the sympathetic and parasympathetic nervous systems that respectively raise and lower cellular cAMP levels.

In embodiments of the bypass bridge expressing a HCN chimera, the chimeric HCN channel preferably provides an improved characteristic, as compared to a wild-type HCN channel, selected from the group consisting of faster kinetics, more positive activation, increased expression, increased stability, preserved or enhanced cAMP responsiveness, and preserved or enhanced neurohumoral response. HCN chimeras for inducing pacemaker activity in cells is described in detail in U.S. Provisional Application No. 60/715,934 (filed Sep. 9, 2005) and 60/832,515, entitled "Chimeric HCN Channels," which is being filed concurrently with the subject application (Jul. 21, 2006), both of which are herein incorporated by reference in their entirety.

As used herein, a "HCN chimera" or "chimeric HCN channel" shall mean a HCN channel comprising portions of more than one HCN channel isoform. Thus, a chimera may comprise portions of HCN1 and HCN2 or HCN3 or HCN4, and so forth. In preferred embodiments, the portions are an amino terminal portion, an intramembranous portion, and a carboxy terminal portion. In other preferred embodiments, the portions are derived from human HCN isoforms. In addition, an HCN chimera encompasses an ion channel comprising portions of HCN channels derived from different animal species. Accordingly, in various embodiments of the bypass bridge, at least one portion of the HCN chimera is derived from an animal species which is different from the animal species from which at least one of the other two portions is derived. For example, one portion of the channel may be derived from a human and another portion may be derived from a non-human.

In additional embodiments of the instant bypass bridge, the HCN chimera is mHCN112, mHCN212, mHCN312, mHCN412, mHCN114, mHCN214, mHCN314, mHCN414, hHCN112, hHCN212, hHCN312, hHCN412, hHCN114, hHCN214, hHCN314, or hHCN414. In different embodiments, the HCN chimera is mHCN112, mHCN212, mHCN312, mHCN412, mHCN114, mHCN214, mHCN314, mHCN414, hHCN112, hHCN212, hHCN312, hHCN412, hHCN114, hHCN214, hHCN314, or hHCN414. In a preferred embodiment, the HCN chimera is hHCN212 having the sequence set forth in SEQ ID NO: 2 (see FIG. 2). In yet another preferred embodiment, the HCN chimera is mHCN212 having the sequence set forth in SEQ ID NO: 6 (see FIG. 3).

As used herein, the term "HCNXYZ" (wherein X, Y and Z are any one of the integers 1, 2, 3 or 4, with the proviso that at least one of X, Y and Z is a different number from at least one of the other numbers) shall mean a chimeric HCN channel polypeptide comprising three contiguous portions in the order XYZ, wherein X is an N-terminal portion, Y is an intramembrane portion, and Z is a C-terminal portion, and wherein the number X, Y or Z designates the HCN channel from which that portion is derived. For example, HCN112 is an HCN chimera with a N-terminal portion and intramembrane portion from HCN1 and a C-terminal portion from HCN2.

In certain embodiments of the bypass bridge, the HCN chimera comprises an amino terminal portion contiguous with an intramembrane portion contiguous with a carboxy terminal portion, wherein each portion is a portion of an HCN channel or a portion of a mutant thereof, and wherein one portion derives from an HCN channel or a mutant thereof which is different from the HCN channel or mutant thereof from which at least one of the other two portions derive. Thus, in various embodiments, at least one portion of the chimera is derived from a HCN channel containing a mutation which provides an improved characteristic, as compared to a portion from a wild-type HCN channel, selected from the group consisting of faster kinetics, more positive activation, increased expression, increased stability, preserved or enhanced cAMP responsiveness, and preserved or enhanced neurohumoral response. In certain embodiments, the mutant HCN channel contains a mutation in a region of the channel selected from the group consisting of the S4 voltage sensor, the S4-S5 linker, S5, S6 and S5-S6 linker, the C-linker, and the CNBD. In other embodiments, the mutant portion is derived from mHCN2 having the sequence set forth in SEQ ID NO: 14 (see FIG. 1) and comprises E324A-mHCN2, Y331A-mHCN2, R339A-mHCN2, or Y331A,E324A-mHCN2. In preferred embodiments, the mutant portion comprises E324A-mHCN2.

The pacemaker activity of a HCN channel may be enhanced by co-expressing the HCN channel with its beta subunit, MiRP1, which increases the magnitude of the current expressed and/or speeds its kinetics of activation. See U.S. Pat. No. 6,783,979 and Qu et al. (2004), the entire contents of which are incorporated herein by reference.

In certain embodiments of the bypass bridge disclosed herein, the pacemaker current is conducted by electrotonic conduction. In other embodiments, the pacemaker current is actively propagated by an action potential. In further embodiments, the action potential is a sodium-dependent action potential. In additional embodiments, cells in the tract further functionally express an L-type calcium channel and the action potential is a calcium-dependent action potential.

The present invention also provides a kit comprising a packaging material containing therein (a) any of the bypass bridges disclosed herein. The kit may also contain labeling and instructions for implanting the bypass bridge in a heart, so as to thereby treat a disorder associated with impaired conduction, or a disorder associated with both impaired conduction and impaired sinus node activity, in a subject's heart in a subject's heart.

This invention also provides a tandem pacemaker system comprising (1) any of the bypass bridges disclosed herein, and (2) an electronic pacemaker and/or a biological pacemaker, wherein the bypass bridge operates in tandem with the electronic and/or biological pacemaker to more effectively treat a cardiac rhythm condition compared to the use of the biological or electronic pacemaker alone. In various embodiments, the bypass bridge is an AV bridge. The biological pacemaker or electronic pacemaker may have a pacing level at, around, above or below the normal resting sinus node pacemaker level. In embodiments where a biological pacemaker or electronic pacemaker is used in tandem with an AV bridge described herein, the natural AV node may be ablated. Further details of tandem pacemaker systems comprising a bypass bridge may be found in U.S. Provisional Application Nos. 60/701,312 (filed Jul. 21, 2005) and 60/781,723 (filed Mar. 14, 2006), and U.S. Ser. No. 11/490,997, filed concurrently herewith on Jul. 21, 2006, entitled "Tandem Cardiac Pacemaker System." The proceeding applications are herein incorporated by reference in their entirety.

The invention also provides a method of making a bypass bridge for implantation in a heart comprising (a) transfecting a cell with, and functionally expressing therein, a nucleic acid encoding a sodium channel, and (b) growing the transfected cell into a tract of cells having a first and a second end capable of being attached to two selected sites in the heart, wherein the cells are physically interconnected via electrically conductive gap junctions. An embodiment of this method further comprises transfecting cells in the tract with a nucleic acid encoding a pacemaker ion channel, wherein the nucleic acid is functionally expressed so as to induce a pacemaker current in the cells. In preferred embodiments, the pacemaker ion channel is expressed in cells in the first end of the tract. In more preferred embodiments, the cells expressing the pacemaker ion channel are located in a region extending 0.5 mm from the first end. In these embodiments, the transfection method used to introduce the pacemaker channel gene(s) to the first end may be locally applied, or separated from the distal portions of the tract using physical barriers, in order to restrict transfection to first end portion.

In various embodiments, the pacemaker ion channel is at least one of (a) a hyperpolarization-activated, cyclic nucleotide-gated (HCN) ion channel or a mutant or chimera thereof, and (b) a MiRP1 beta subunit. In preferred embodiments of the instant methods, the cells are hMSCs or hESCs, wherein said cells are substantially incapable of differentiation. In further embodiments, the human adult mesenchymal stem cells (a) express CD29, CD44, CD54, and HLA class I surface markers; and (b) do not express CD14, CD34, CD45, and HLA class II surface markers. In still further embodiments, the human adult mesenchymal stem cells have been passaged at least 9 times.

Additional embodiments of the instant methods for making a bypass bridge further comprise transfecting the cell with, and expressing therein, at least one nucleic acid encoding one or more of at least one cardiac connexin, an alpha subunit with accessory subunits of an L-type calcium channel, or an alpha subunit with or without accessory subunits of the potassium channel, such that implantation of a bypass bridge in a heart changes the voltage-time course of repolarization and/or refractoriness of the heart.

Variations of the instant methods for making a bypass bridge comprise (a) growing a cell into a tract of cells having a first and a second end capable of being attached to two selected sites in the heart, wherein the cells are physically interconnected via electrically conductive gap junctions, before (b) transfecting the cells in the tract with, and functionally expressing therein, a nucleic acid encoding a sodium channel, and optionally other ion channel genes and/or a pacemaker channel gene.

This invention further provides a method of implanting a bypass bridge in a heart comprising (a) making a bypass bridge comprising a tract of cells by any of the methods disclosed herein, (b) selecting a first and a second site in the heart, and (c) attaching the first end of the tract to the first site and the second end of the tract to the second site, so as to thereby implant a bypass bridge in the heart that allows the conduction of a pacemaker and/or electrical signal/current across the tract between the two sites. Other embodiments further comprise transfecting cells in the tract with a nucleic acid encoding a pacemaker ion channel, wherein the nucleic acid is functionally expressed so as to induce a pacemaker current in the cells. In preferred embodiments, the pacemaker ion channel is expressed in cells in the first end of the tract. In more preferred embodiments, the cells expressing the pacemaker ion channel are located in a region extending 0.5 mm from the first end. In other preferred embodiments, the first site is in an atrium and the second site is in a ventricle, so as to allow propagation of a pacemaker and/or electrical signal/current across the tract from the atrium to the ventricle. In different embodiments of the instant methods, the a pacemaker and/or electrical signal/current is generated in the atrium by the sinus node, an electronic pacemaker, a biological pacemaker, or cells within the bypass bridge expressing a pacemaker current. In further embodiments, the pacemaker ion channel is at least one of (a) a hyperpolarization-activated, cyclic nucleotide-gated (HCN) ion channel or a mutant or chimera thereof, and (b) a MiRP1 beta subunit.

In additional embodiments of the instant methods, the cells in the tract of the bypass bridge are stem cells, cardiomyocytes, fibroblasts or skeletal muscle cells engineered to express at least one cardiac connexins, or endothelial cells. In various embodiments, the stem cells are adult MSCs or ESCs, wherein said cells are substantially incapable of differentiation. In preferred embodiments, the stem cells are hMSCs or hESCs, wherein said stem cells are substantially incapable of differentiation. Other embodiments further comprise transfecting the cells with, and expressing therein, at least one nucleic acid encoding one or more of at least one cardiac connexin, an alpha subunit with accessory subunits of an L-type calcium channel, or an alpha subunit with or without accessory subunits of the potassium channel, so as to change the voltage-time course of repolarization and/or refractoriness of the heart. In further embodiments, the at least one connexin is Cx43, Cx40, or Cx45.

The present invention also provides a method of treating a disorder associated with an impaired conduction in a subject's heart comprising (a) transfecting a cell with a nucleic acid encoding a sodium channel, wherein the cell functionally expresses the sodium channel, (b) growing the transfected cell into a tract of cells having a first end and a second end, wherein the cells are physically interconnected via electrically conductive gap junctions, (c) selecting a first site and a second site in the subject's heart between which sites conduction is impaired, and (d) attaching the first end of the tract to the first site and the second end of the tract to the second site, so as to allow the conduction of a pacemaker and/or electrical signal/current across the tract between the two sites and thereby treat the subject.

As used herein, "treating" a disorder shall mean causing the subject afflicted with the disorder to experience a reduction, remission or regression of the disorder and/or its symptoms. In various embodiments, recurrence of the disorder and/or its symptoms is prevented. In preferred embodiments, the subject is cured of the disorder and/or its symptoms. To "functionally express" a nucleic acid shall mean that a cell or other biological system into which the nucleic acid has been introduced produces a functional polypeptide encoded by the nucleic acid. The encoded polypeptide itself may also be said to be functionally expressed.

This invention further provides a method of treating a disorder associated with an impaired conduction and impaired sinus node activity in a subject's heart comprising (a) transfecting a cell with at least one nucleic acid encoding a sodium channel and a pacemaker ion channel, wherein the cell functionally expresses the sodium channel and the pacemaker ion channel, (b) growing the transfected cell into a tract of cells having a first end and a second end, wherein the cells are physically interconnected via electrically conductive gap junctions, (c) selecting a first site in the left atrium of the heart and a second site, between which sites conduction is impaired, and (d) attaching the first end of the tract to the first site and the second end of the tract to the second site, so as to allow the propagation of a pacemaker and/or electrical signal/current generated by the sinus node and/or tract of cells between the two sites and thereby treat the subject.

In embodiments of the instant methods, the cells are hMSCs or hESCs, wherein said stem cells are substantially incapable of differentiation. Various embodiments further comprise transfecting the cells in the tract with, and expressing therein, at least one nucleic acid encoding one or more of at least one cardiac connexin, an alpha subunit with accessory subunits of an L-type calcium channel, or an alpha subunit with or without accessory subunits of the potassium channel, so as to change the voltage-time course of repolarization and/or refractoriness of the heart. In further embodiments, the pacemaker ion channel is at least one of (a) a hyperpolarization-activated, cyclic nucleotide-gated (HCN) ion channel or a mutant or chimera thereof, and (b) a MiRP1 beta subunit.

The present invention encompasses a variety of kits comprising the bypass bridge of the instant invention, as well as methods for making a bypass bridge, methods of implanting a bypass bridge in a heart, and methods of treating a disorder, corresponding to each of the different embodiments of the bypass bridge disclosed herein. These variant kits and methods are not all individually described in detail herein but will be readily evident and understood to one of ordinary skill in the art based on the disclosure of the different embodiments of the bypass bridge. Accordingly, the various embodiments described herein may be equally applied as appropriate to the bypass bridges, kits and methods of this invention.

The following Examples are presented to aid in understanding the invention, and are not intended, and should not be construed, to limit in any way the invention set forth in the claims which follow thereafter. These Examples do not include detailed descriptions of experimental methods that are well known to those of ordinary skill in the art, such as methods used in the construction of recombinant nucleic acid vectors, transfection of host cells with such recombinant vectors, and the functional expression of genes in transfected cells. Detailed descriptions of such conventional methods are provided in numerous publications, including Sambrook et al. (1989), the contents of which are hereby incorporated herein in their entirety.

EXAMPLE 1

Culture of Gap Junction-Coupled Human Mesenchymal Stem Cells

Cell Cultures

Human mesenchymal stem cells (hMSCs; mesenchymal stem cells, human bone marrow; Poietics™) were purchased from Clonetics/BioWhittaker (Walkersville, Md., USA), cultured in mesenchymal stem cell (MCS) growth medium and used from passages 2-4. Isolated and purified hMSCs can be cultured for many passages (12) without losing their unique properties, i.e., normal karyotype and telomerase activity (van den Bos et al., 1997; Pittenger et al., 1999).

HeLa cells transfected with rat Cx40, rat Cx43 or mouse Cx45 were cocultured with hMSCs. Production, characterization and culture conditions of transfected HeLa cells have been previously described (Elfgang et al., 1995; Valiunas et al., 2000; 2002).

Anti-Connexin Antibodies, Immunofluorescent Labeling, and Immunoblot Analysis

Commercially available mouse anticonnexin monoclonal and polyclonal antibodies (Chemicon International, Temecula, Calif.) of Cx40, Cx43 and Cx45 were used for immunostaining and immunoblots as described earlier (Laing and Beyer, 1995). Fluorescein-conjugated goat antimouse or antirabbit IgG (ICN Biomedicals, Inc., Costa Mesa, Calif.) was used as secondary antibody.

Electrophysiological Measurements Across Gap Junctions

Glass coverslips with adherent cells were transferred to an experimental chamber perfused at room temperature (~22° C.) with bath solution containing (mM): NaCl, 150; KCl, 10; $CaCl_2$, 2; Hepes, 5 (pH 7.4); glucose, 5. The patch pipettes were filled with solution containing (mM): potassium aspartate, 120; NaCl, 10; MgATP, 3; Hepes, 5 (pH 7.2); EGTA, 10 (pCa ~8); filtered through 0.22 μm pores. When filled, the resistance of the pipettes measured 1-2 MΩ. Experiments were carried out on cell pairs using a double voltage-clamp. This method permitted control of the membrane potential ($V_m$) and measurement of the associated junctional currents ($I_j$).

Dye Flux Studies

Dye transfer through gap junction channels was investigated using cell pairs. Lucifer Yellow (LY; Molecular Probes) was dissolved in the pipette solution to reach a concentration of 2 mM. Fluorescent dye cell-to-cell spread was imaged using a 16 bit 64 000 pixel grey scale digital CCD-camera (LYNXX 2000T, SpectraSource Instruments, Westlake Village, Calif.) (Valiunas et al., 2002). In experiments with heterologous pairs, LY was always injected into the cells which were tagged with Cell Tracker Green. The injected cell fluorescence intensity derived from LY is 10-15 times higher than the initial fluorescence from Cell Tracker Green.

Human MSCs Express Connexins

The connexins, Cx43 and Cx40, were immunolocalized, as evidenced by typical punctate staining, along regions of intimate cell-to-cell contact and within regions of the cytoplasm of the hMSCs grown in culture as monolayers (FIGS. 4A, B). Cx45 staining was also detected, but unlike that of Cx43 or Cx40, was not typical of connexin distribution in cells. Rather, it was characterized by fine granular cytoplasmic and reticular-like staining with no readily observed membrane-associated plaques (FIG. 4C). This does not exclude the possibility that Cx45 channels exist but does imply that their number relative to Cx43 and Cx40 homotypic, heterotypic and heteromeric channels is low. FIG. 4D illustrates Western blot analysis for canine ventricle myocytes and hMSCs with a Cx43 polyclonal antibody which adds further proof of Cx43 presence in hMSCs.

Gap Junctional Coupling Between hMSCs and Various Cell Lines

Gap junctional coupling among hMSCs is demonstrated in FIG. 5. Junctional currents recorded between hMSC pairs show quasi-symmetrical (FIG. 5A) and asymmetrical (FIG. 5B) voltage dependency arising in response to symmetrical 10-s transjunctional voltage steps ($V_j$) of equal amplitude but opposite sign starting from ±10 mV to ±110 mV using increments of 20 mV. These behaviors are typically observed in cells which co-express Cx43 and Cx40 (Valiunas et al., 2001).

Figure 5A:
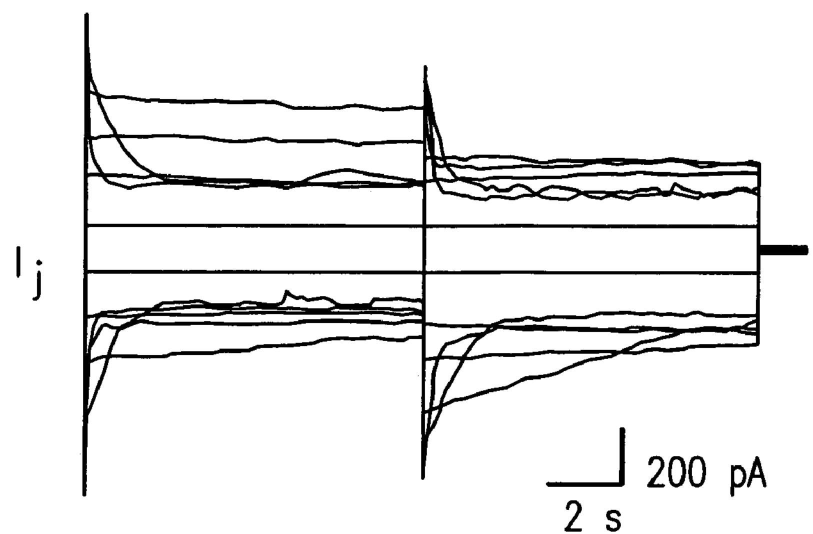
FIG. 5. Macroscopic and single channel properties of gap junctions between hMSC pairs. Gap junction currents ($I_j$) elicited from hMSCs using a symmetrical bipolar pulse protocol (10 s, from ±10 mV to ±110 mV, $V_h$=0 mV) showed two types of voltage-dependent current deactivation: symmetrical (A) and asymmetrical (B). C, summary plots of normalized instantaneous (○) and steady-state (●) $g_j$ versus $V_j$. Left panel, quasi-symmetrical relationship from 5 pairs; continuous line, Boltzmann fit: $V_{j,0}$=−70/65 mV, $g_{j,min}$=0.29/0.34, $g_{j,max}$=0.99/1.00, z=2.2/2.3 for negative/positive $V_j$. Right panel, asymmetrical relationship from 6 pairs; Boltzmann fit for negative $V_j$: $V_{j,0}$=−72 mV, $g_{j,min}$=0.25, $g_{j,max}$=0.99, z=1.5. D and E, single channel recordings from pairs of hMSCs. Pulse protocol ($V_1$ and $V_2$) and associated multichannel currents ($I_2$) recorded from a cell pair during maintained $V_j$ of ±80 mV. The discrete current steps indicate the opening and closing of single channels. Dashed line: zero current level. The all points current histograms on the right-hand side reveal a conductance of ~50 pS.
Figure 5B:
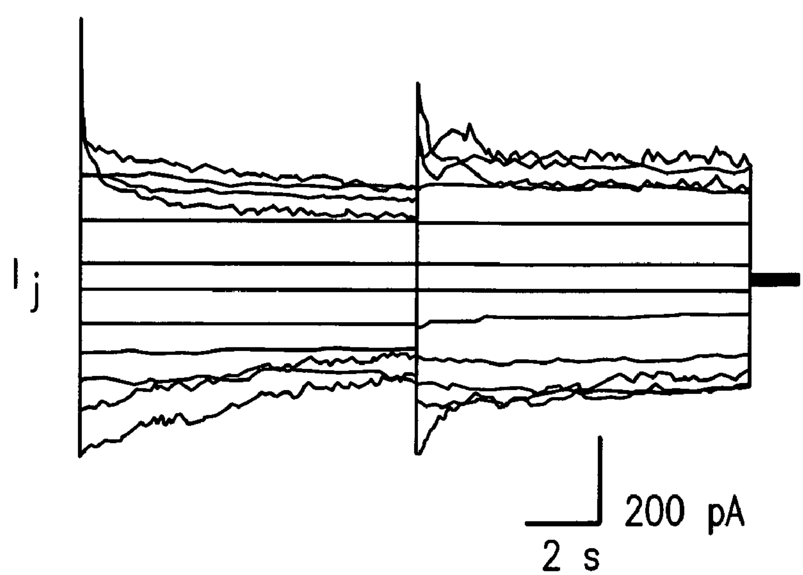
Figure 5C:
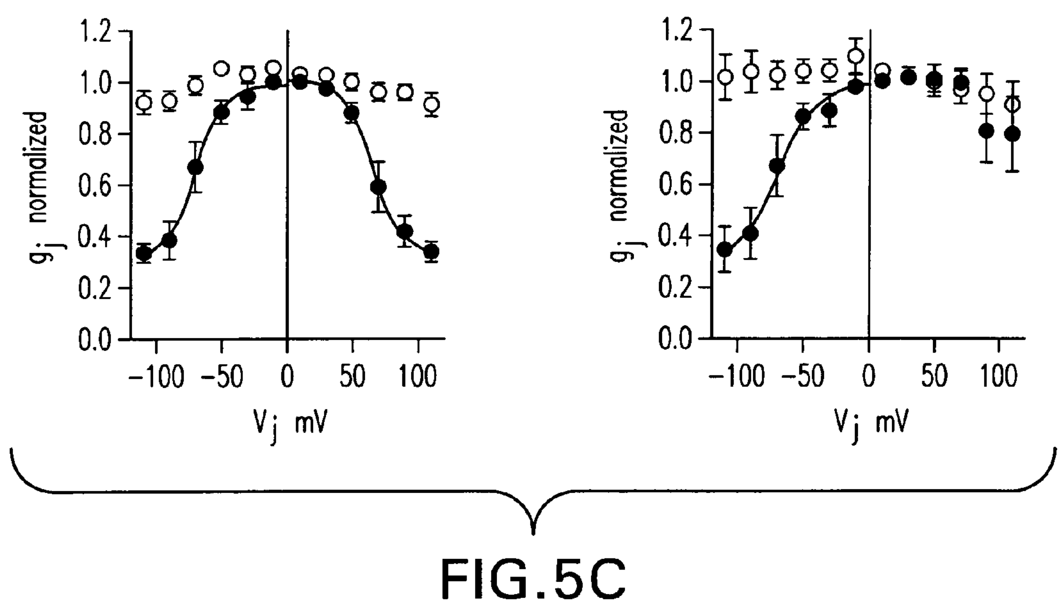

FIG. 5C summarizes the data obtained from hMSC pairs. The values of normalized instantaneous ($g_{j,inst}$, ○) and steady state conductances ($g_{j,ss}$, ●) (determined at the beginning and at the end of each $V_j$ step, respectively) were plotted versus $V_j$. The left panel shows a quasi-symmetrical relationship from five hMSC pairs. The continuous curves represent the best fit of data to the Boltzmann equation with the following parameters: half-deactivation voltage, $V_{j,0}$=−70/65 mV; minimum $g_j$, $g_{j,min}$=0.29/0.34; maximum $g_j$, $g_{j,max}$=0.99/1.00; gating charge, z=2.2/2.3 for negative/positive $V_j$, respectively. Summarized plots from six asymmetrical cases are shown in the right panel. The $g_{j,ss}$ declined in sigmoidal fashion at negative $V_j$ and showed a reduced voltage sensitivity to positive $V_j$. Boltzman fitting for negative $V_j$ revealed the following values: $V_{j,0}$=−72 mV, $g_{j,min}$=0.25, $g_{j,max}$=0.99, z=1.5.

Figure 5D:
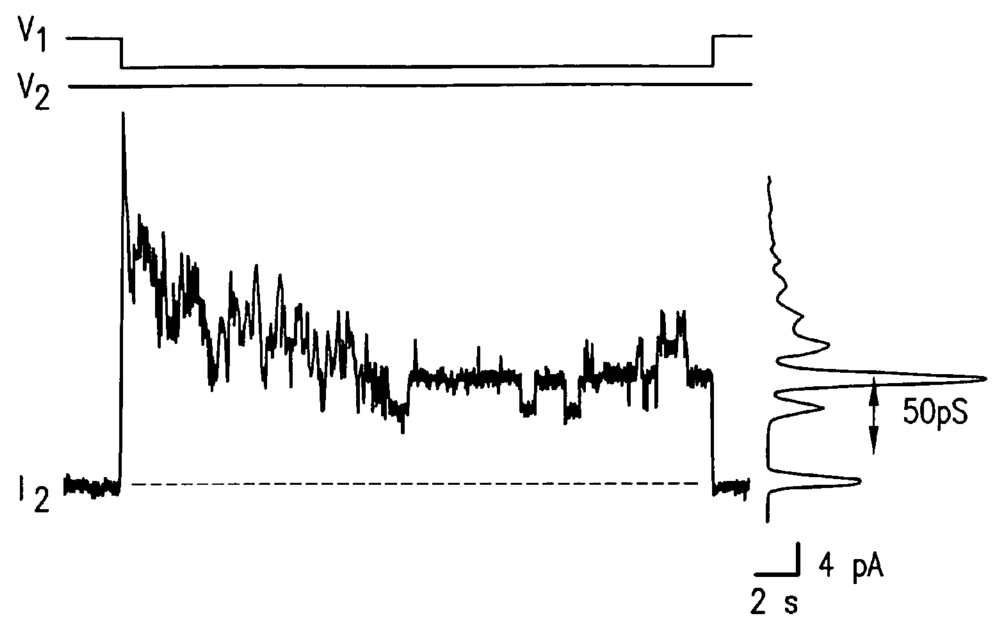
Figure 5E:
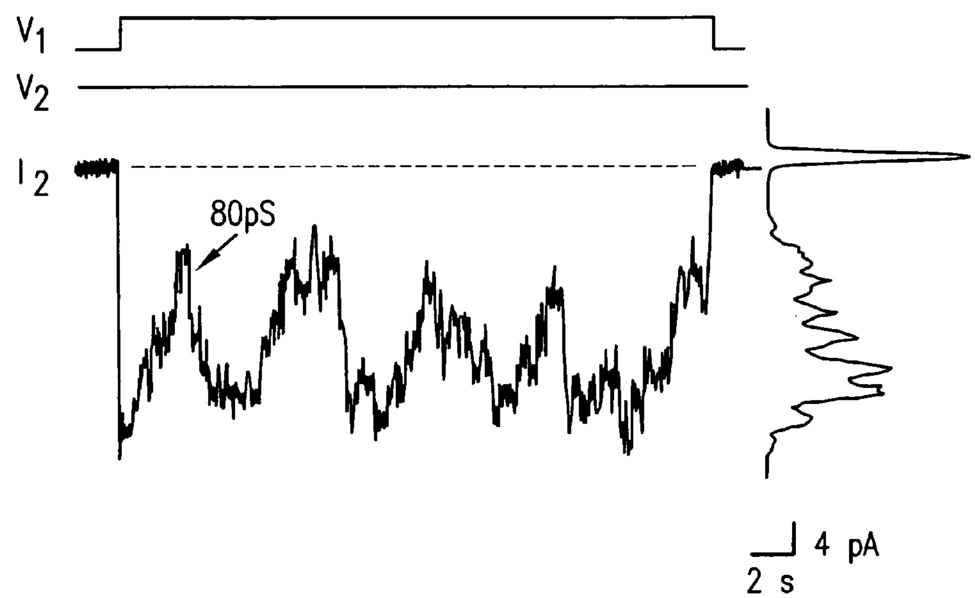

FIGS. 5D and E illustrate typical multichannel recordings from a hMSC pair. Using 120 mM K aspartate as a pipette solution, channels were observed with unitary conductances of 28-80 pS range. Operation of channels with ~50 pS conductance (see FIG. 5D) is consistent with previously published values (Valiunas et al., 1997; 2002) for Cx43 homotypic channels. This does not preclude the presence of other channel types, it merely suggests that Cx43 forms functional channels in hMSCs.

Figure 6A:
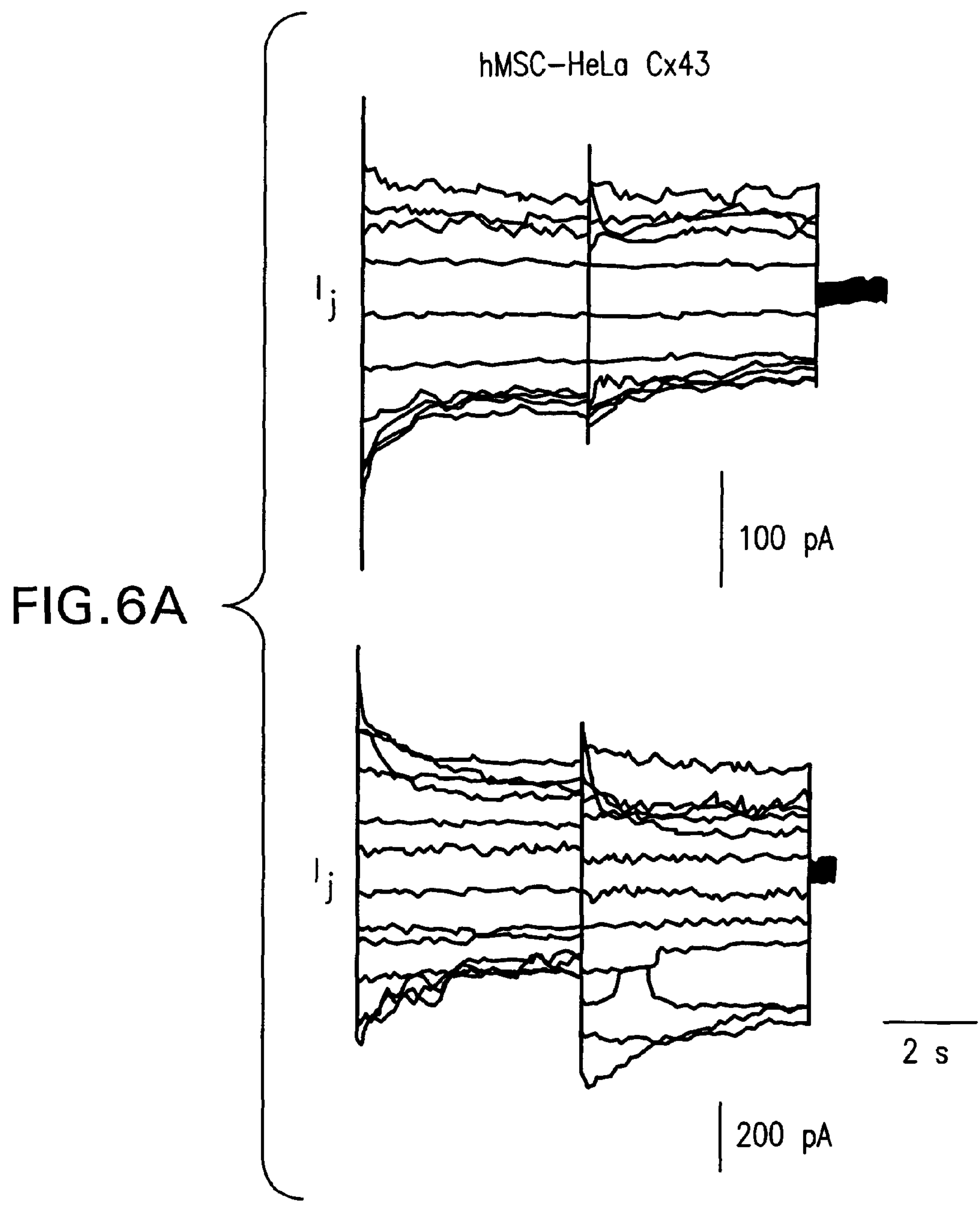
FIG. 6. Macroscopic properties of functions in cell pairs between a hMSC and HeLa cell expressing only Cx40, Cx43 or Cx45. In all cases hMSC to Hela cell coupling was tested 6 to 12 after hours initiating co-culture. A, Ij elicited in response to a series of 5-s voltage steps ($V_j$) in hMSC-HeLaCx43 pairs. Top, symmetrical current deactivation; bottom, asymmetrical current voltage dependence. B, Macroscopic Ij recordings from hMSC-HelaCx40 pairs exhibit symmetrical (top panel) and asymmetrical (bottom panel) voltage dependent deactivation. C, Asymmetric Ij from hMSC-HeLaCx43 pair exhibits voltage dependent gating when Cx45 side is relatively negative. Ij recorded from hMSC. D, $g_{j,ss}$ plots versus $V_j$ from pairs between hMSC and transfected HeLa cells. Left panel, hMSC-HeLaCx43 pairs, quasi-symmetrical relationship (●) and asymmetrical relationship (○); continuous and dashed lines are Boltzmann fits (see text for details). Middle panel, symmetrical (●) and asymmetrical (○) relationships from hMSC-HeLaCx40 pairs; the continuous and dashed lines correspond to Boltzmann fits (see text for details). Right panel, asymmetrical relationship from hMSC-HeLaCx45 cell pairs; continuous line, Boltzmann fit for positive $V_j$ (see text for details). E, Cell-to-cell Lucifer Yellow (LY) spread in cell pairs: from an hMSC to an hMSC (upper panel), from a HeLaCx43 to an hMSC (middle panel), and from an hMSC to a HeLaCx43 (bottom panel). In all cases a pipette containing 2 mM LY was attached to the left-hand cell in the whole-cell configuration. Epifluorescent micrographs taken at 12 min after dye injection show LY spread to the adjacent (right-hand) cell. The simultaneously measured junctional conductance revealed $g_j$ of ~13 nS, ~16 nS, and ~18 nS of the pairs, respectively. Cell Tracker green was used to distinguish hMSCs from HeLa cells or vice versa in all experiments.
Figure 6B:
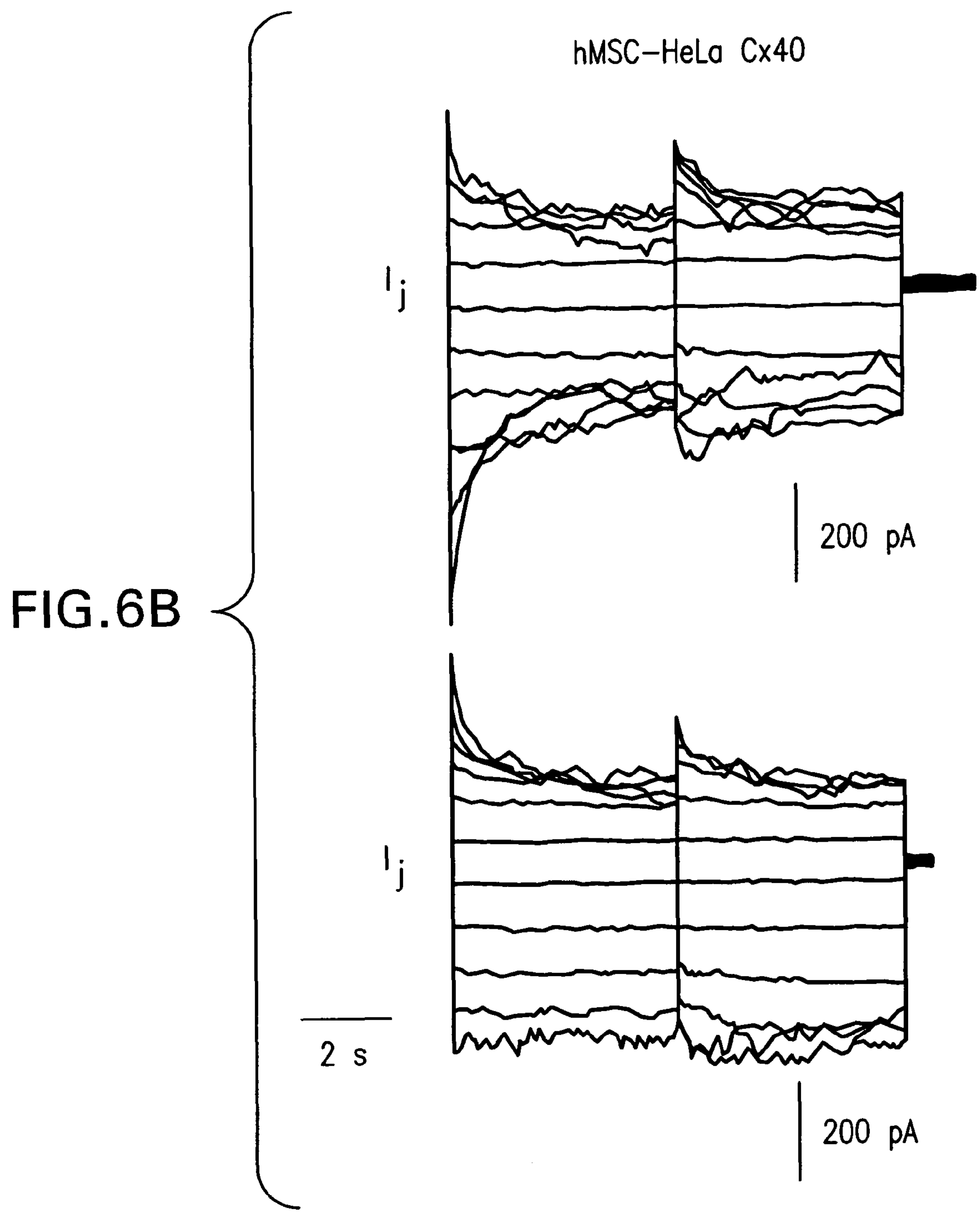
Figure 6C:
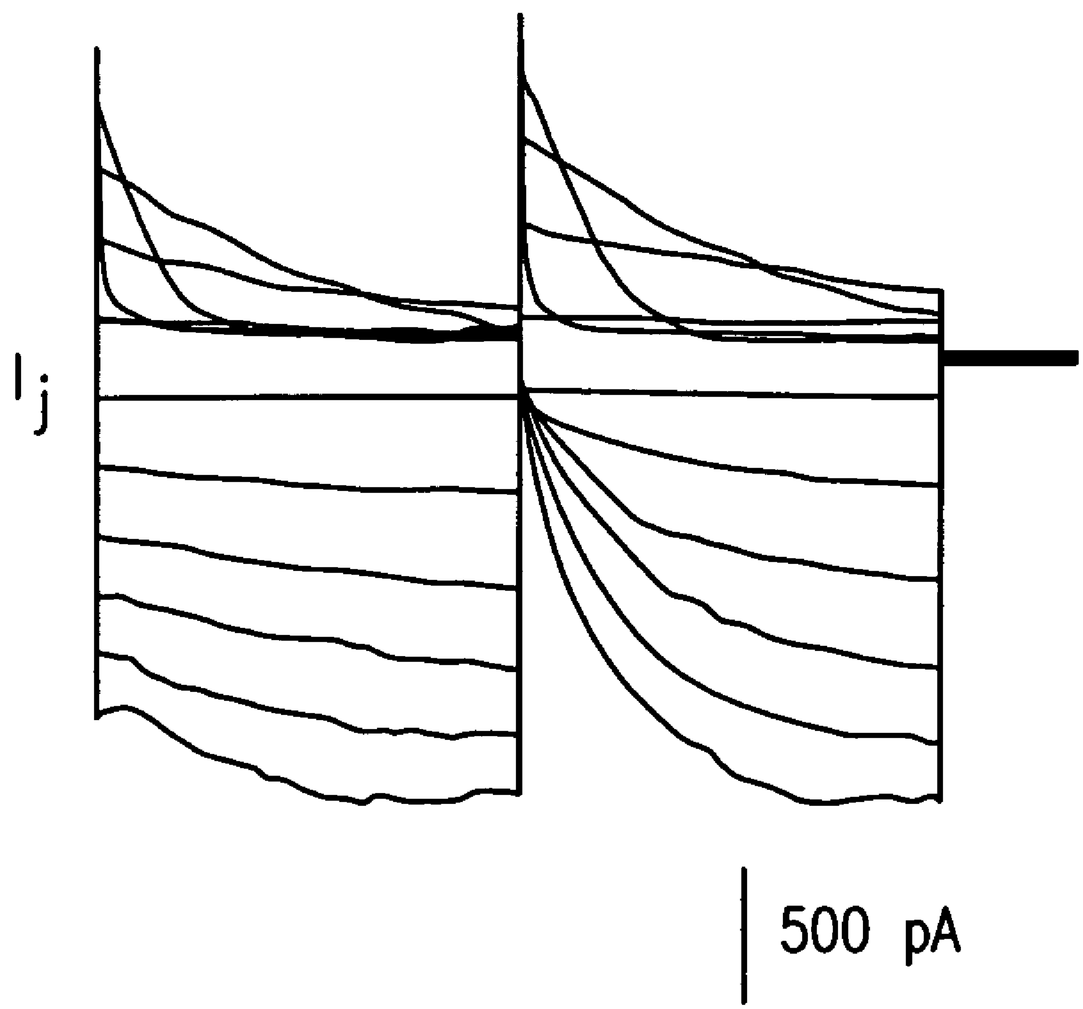

To further define the nature of the coupling, hMSCs were co-cultured with human HeLa cells stably transfected with Cx43, Cx40, and Cx45 (Elfgang et al., 1995) and it was found that hMSCs were able to couple to all these transfectants. FIG. 6A shows an example of junctional currents recorded between an hMSC and HeLaCx43 cell pairs that manifested symmetrically and asymmetrically voltage dependent currents in response to a series (from +10 mV to +110 mV) of symmetrical transjunctional voltage steps ($V_j$). The quasi-symmetric record suggests that the dominant functional channel is homotypic Cx43 while the asymmetric record suggests the activity of another connexin in the hMSC (presumably Cx40 as shown by immunohistochemistry, see FIG. 4) that could be either a heterotypic or heteromeric form or both. These records are similar to those published for transfected cells: heterotypic and mixed (heteromeric) forms of Cx40 and Cx43 (Valiunas et al., 2000; 2001). Co-culture of hMSCs with HeLa cells transfected with Cx40 (FIG. 6B) also revealed symmetric and asymmetric voltage dependent junctional currents consistent with the co-expression of Cx43 and Cx40 in the hMSCs similar to the data for Cx43 HeLa-hMSC pairs. HeLa cells transfected with Cx45 coupled to hMSCs always produced asymmetric junctional currents with pronounced voltage gating when Cx45 (HeLa) side was negative (FIG. 6C). This is consistent with the dominant channel forms in the hMSC being Cx43 and Cx40 as both produce asymmetric currents when they form heterotypic channels with Cx45 (Valiunas et al., 2000; 2001). This does not exclude Cx45 as a functioning channel in hMSCs but it does indicate that Cx45 is a minor contributor to cell to cell coupling in hMSCs. The lack of visualized plaques in the immunostaining for Cx45 (FIG. 7) further supports this interpretation.

Figure 6D:
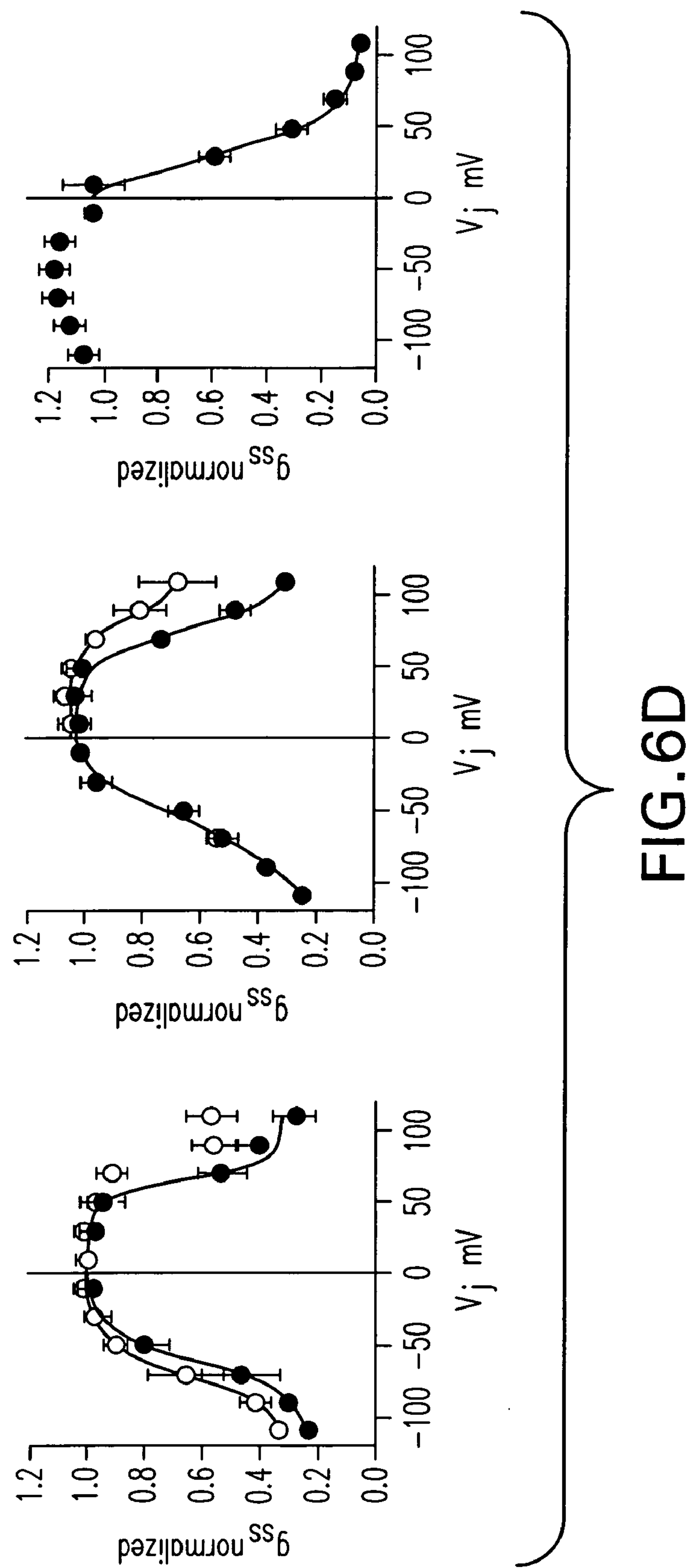

The summarized plots of $g_{j,ss}$ versus $V_j$ from pairs between hMSC and transfected HeLa cells are shown in FIG. 6D. The left panel shows the results from hMSC-HeLaCx43 pairs. For symmetrical data (●, four preparations), Boltzmann fits (continuous lines) yielded the following parameters: $V_{j,0}$=−61/65 mV, $g_{j,min}$=0.24/0.33, $g_{j,max}$=0.99/0.99, z=2.4/3.8 for negative/positive $V_j$. For asymmetrical data (○, three preparations), the Boltzmann fit (dashed line) at negative $V_j$ values revealed the following parameter values: $V_{j,0}$=−70 mV, $g_{j,min}$=0.31, $g_{j,max}$=1.00, z=2.2. The middle panel shows data from hMSC-HeLaCx40 pairs including three symmetrical (●) and two asymmetrical (○) $g_{j,ss}$-$V_j$ relationships. The continuous lines correspond to a Boltzmann fit to symmetrical data ($V_{j,0}$=−57/76 mV, $g_{j,min}$=0.22/0.29, $g_{j,max}$=1.1/1.0, z=1.4/2.3; negative/positive $V_j$) and the dashed line is a fit to the asymmetrical data ($V_{j,0}$=−57/85 mV, $g_{j,min}$=0.22/0.65, $g_{j,max}$=1.1/1.0, z=1.3/2.2; negative/positive $V_j$). The data from the six complete experiments from hMSC-HeLaCx45 cell pairs are shown on the right panel. The $g_{j,ss}$ plot versus $V_j$ was strongly asymmetrical and the best fit of the data to the Boltzmann equation at positive $V_j$ values revealed following parameter values: $V_{j,0}$=31 mV, $g_{j,min}$=0.07, $g_{j,max}$=1.2, z=1.8.

Figure 6E:
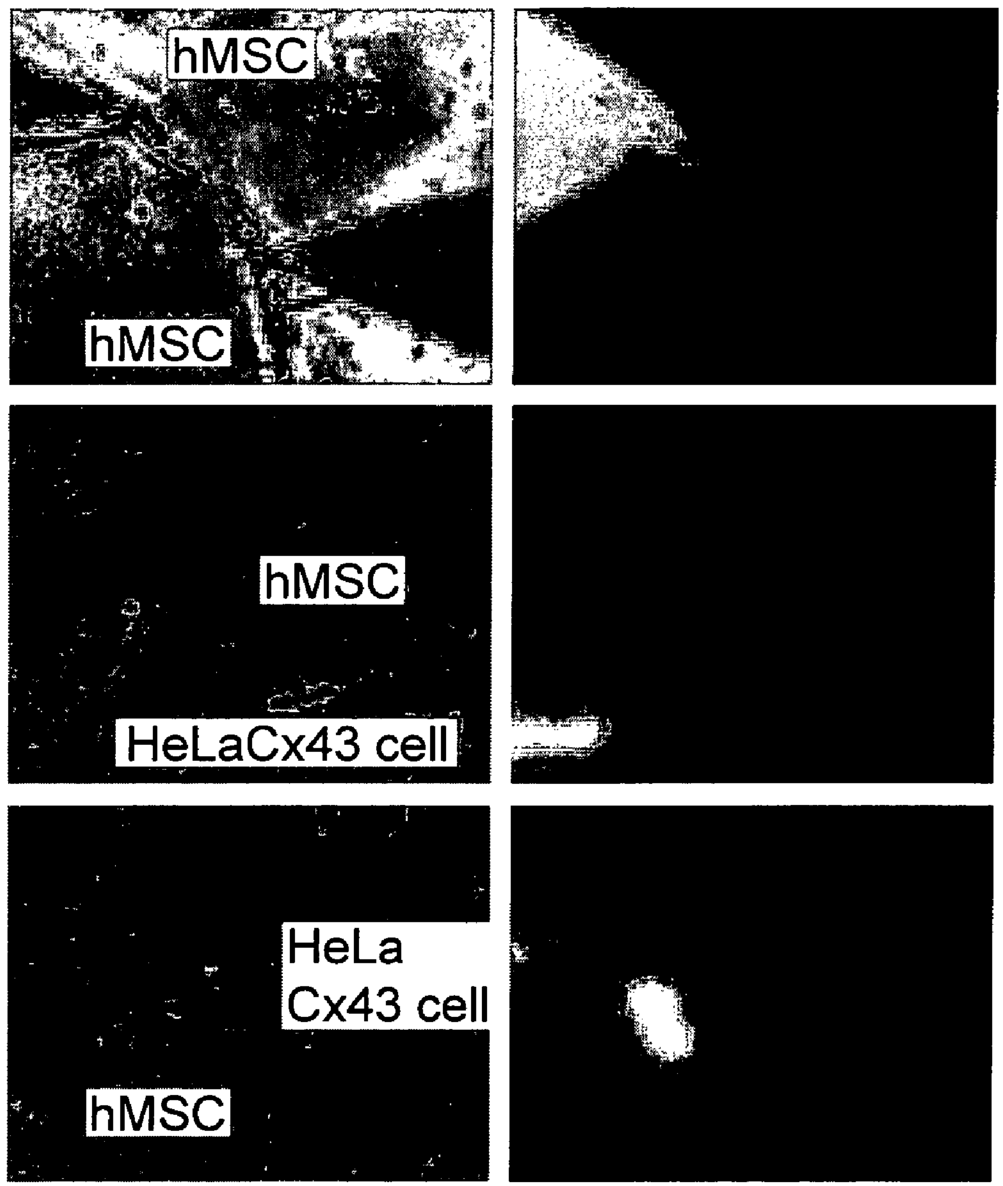

FIG. 6E shows Lucifer Yellow transfer from an hMSC to an hMSC (upper panel), from a HeLaCx43 to an hMSC (middle panel), and from an hMSC to a HeLaCx43 (bottom panel). The junctional conductance of the cell pairs was simultaneously measured by methods described earlier (Valiunas et al., 2002) and revealed conductances of ~13, ~16 and ~18 nS, respectively. The transfer of Lucifer Yellow was similar to that previously reported for homotypic Cx43 or co-expressed Cx43 and Cx40 in HeLa cells (Valiunas et al., 2002). Cell Tracker Green (Molecular Probes) was always used in one of the two populations of cells to allow heterologous pairs to be identified (Valiunas et al., 2000). Lucifer Yellow was always delivered to the cell containing cell tracker. The fluorescence intensity generated by the Cell Tracker Green was 10-15 times less than fluorescence intensity produced by the concentration of Lucifer Yellow delivered to the source cell.

Figure 7C:
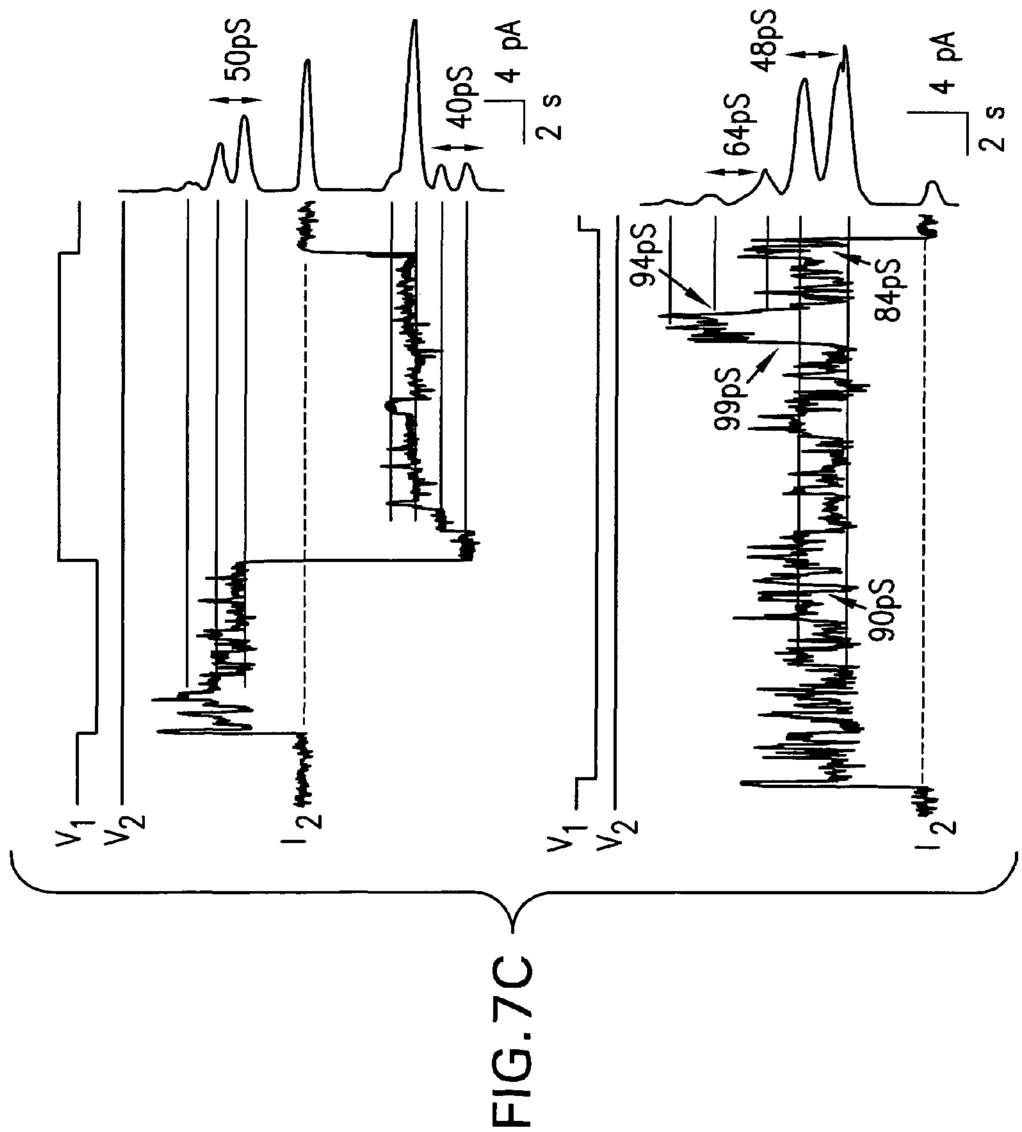
FIG. 7. Macroscopic and single channel properties of gap junctions between hMSC-canine ventricle cell pairs. Myocytes were plated between 12 and 72 h and co-cultured with hMSCs for 6 to 12 h before measuring coupling. A, Localization of Cx43 for hMSC-canine ventricle cell pairs. Most of Cx43 was localized to the ventricular cell ends and a small amount of Cx43 was present along the lateral borders. The intensive Cx43 staining was detected between the end of the rod-shaped ventricular cell (middle cell) and the hMSC (right cell). There is no detectable Cx43 staining between the ventricular cell and the hMSC on the left side. B, Top, phase-contrast micrograph of a hMSC-canine ventricular myocyte pair. Bottom, monopolar pulse protocol ($V_1$ and $V_2$) and associated macroscopic junctional currents ($I_2$) exhibiting asymmetrical voltage dependence. C, Top, multichannel current elicited by symmetrical biphasic 60 mV pulse. Dashed line, zero current level; dotted lines, represent discrete current steps indicative of opening and closing of channels. The current histograms yielded a conductance of 40-50 pS. Bottom, multichannel recording during maintained $V_j$ of 60 mV. The current histograms revealed several conductances of 48-64 pS with several events with conductance of 84 pS to 99 pS (arrows) which resemble operation of Cx43, heterotypic Cx40-Cx43 and/or homotypic Cx40 channels.

Human MSCs were also co-cultured with adult canine ventricular myocytes as shown in FIG. 7. Immunostaining for Cx43 was detected between the rod-shaped ventricular myocytes and hMSCs as shown in FIG. 7A. The hMSCs couple electrically with cardiac myocytes. Both macroscopic (FIG. 7B) and multichannel (FIG. 7C) records were obtained. Junctional currents in FIG. 7B are asymmetrical while those in FIG. 7C show unitary events of the size range typically resulting from the operation of homotypic Cx43 or heterotypic Cx43-Cx40 or homotypic Cx40 channels (Valiunas et al., 2000; 2001). Heteromeric forms are also possible whose conductances are the same or similar to homotypic or heterotypic forms.

The studies of cell pairs have demonstrated effective coupling of hMSC to other hMSC (13.8±2.4 nS, n=14), to HeLaCx43 (7.9±2.1 nS, n=7), to HeLaCx40 (4.6±2.6 nS, n=5), to HeLaCx45 (11±2.6 nS, n=5), and to ventricular myocytes (1.5±1.3 nS, n=4).

These data suggest that MSCs should readily integrate into electrical syncytia of many tissues, promoting repair or serving as the substrate for a therapeutic delivery system. In particular, the data support the possibility of using hMSCs as a therapeutic substrate for repair of cardiac tissue. Other syncytia such as vascular smooth muscle or endothelial cells should also be able to couple to the hMSCs because of the ubiquity of Cx43 and Cx40 (Wang et al., 2001; Beyer, 1993). Thus, they may also be amenable to hMSCs-based therapeutics. For example, hMSCs can be transfected to express ion channels which then can influence the surrounding synctial tissue. Alternatively, the hMSCs can be transfected to express genes that produce small therapeutic molecules capable of permeating gap junctions and influencing recipient cells. Further, for short term therapy, small molecules can be directly loaded into hMSCs for delivery to recipient cells. The success of such approaches is dependent on gap junction channels as the final conduit for delivery of the therapeutic agent to the recipient cells. The feasibility of the first approach has been demonstrated herein by delivering HCN2-transfected hMSCs to the canine heart where they generate a spontaneous rhythm.

EXAMPLE 2

Ion Channels Suitable for Incorporation into a Cardiac Bypass Bridge

As previously described herein, hMSCs form gap junctions that permit a tract of physically connected cells to conduct electrical signals by electrotonic conduction. Cell-to-cell propagation of electrical signals may be facilitated by functionally expressing in the cells one or more nucleic acids encoding at least one of the cardiac connexins Cx43, Cx40 or Cx45 in order to enhance formation of gap junctions. The expression in the cells of a nucleic acid(s) encoding the alpha subunit, with or without the accessory subunits, of a sodium channel, or the alpha and accessory subunits of an L-type calcium channel, also increases the likelihood of not just electrotonic propagation of a wavefront, but its active propagation by a sodium-dependent or calcium-dependent action potential. In addition, expression of a potassium channel in the cells both increases the likelihood of active propagation by an action potential and provides a means of controlling the initial resting potential and its voltage-time course of repolarization and refractoriness.

Figure 10:
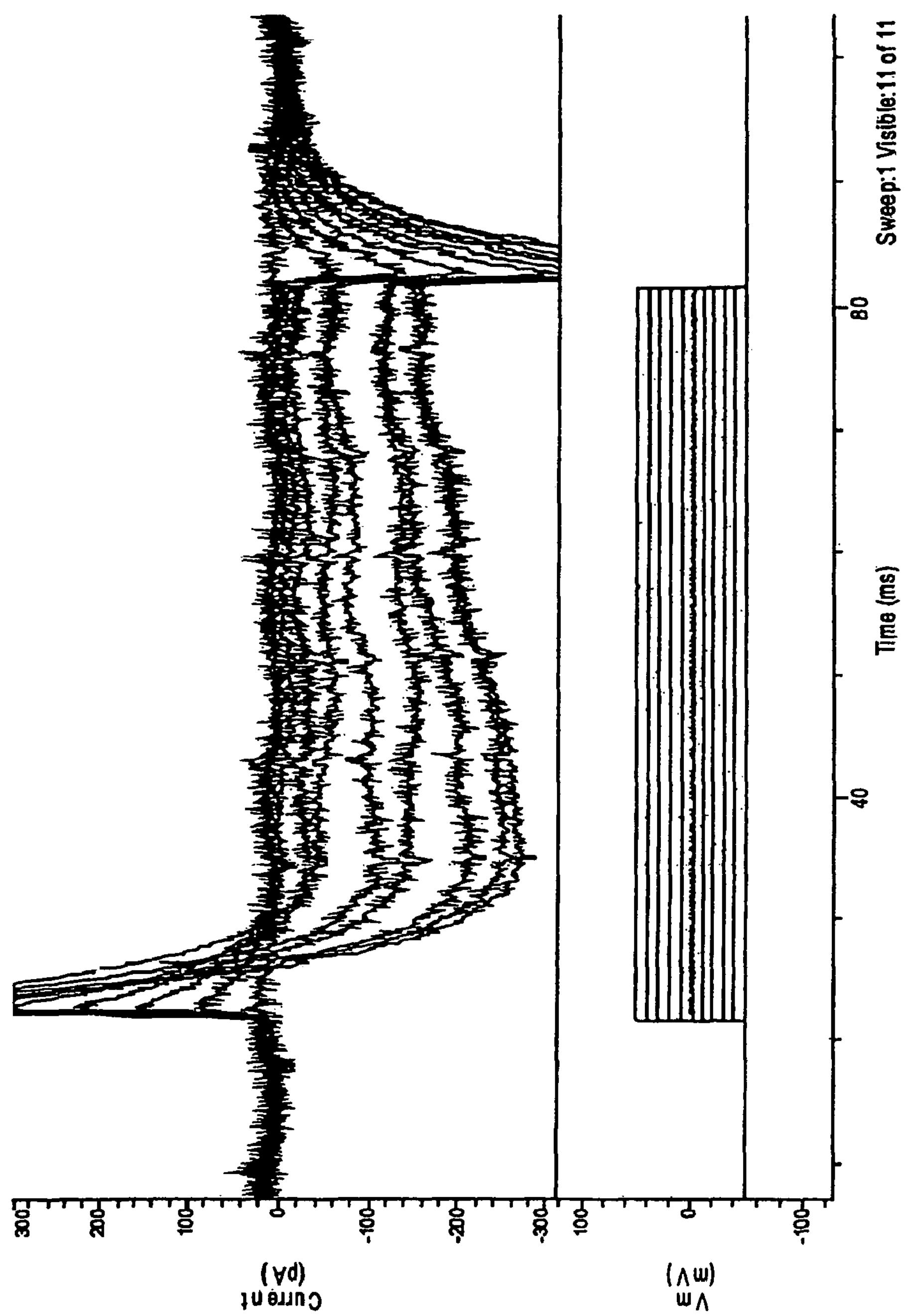
FIG. 10. Biophysical properties of a calcium channel suitable for incorporation into a cardiac bypass bridge. CaV1.2, alpha2 and gamma, P1.b and red fluorescent reporter were co-expressed in HEK293 cells. $Ca^{2+}$ current was recorded in the red fluorescent cells. The cells were held at −50 mV. Test pulses (60 ms) were from −40 mV to +50 mV with a 10 mV interval.

The biophysical properties of a SKM-1 sodium channel and a L-type calcium channel were assayed to investigate their suitability for providing an action potential in a cardiac bypass bridge. The inactivation properties of the SKM-1 sodium channel measured in *Xenopus* oocytes are shown in FIG. 8, and the I-V relationship for the SKM-1 channel in *Xenopus* oocytes is shown in FIG. 9. The CaV1.2, alpha2&gamma, P1.b and red fluorescent reporter were co-expressed in HEK293 cells. FIG. 10 shows the $Ca^{2+}$ current recorded in the red fluorescent cells.

The SKM-1 sodium channel and L-type calcium channel are used to "fine-tune" the conductivity of a bypass bridge to the extent that this is needed. One embodiment of the bypass bridge described herein is an AV bridge. Incorporation of sodium channels in an AV bridge can be viewed as counter-intuitive in that the sodium channel is usually associated with very rapid conduction, whereas an AV bypass should conduct more slowly to operate most efficiently. However, because the degree of coupling among the cells can be manipulated it is possible to use a channel that routinely propagates rapidly and expect this to conduct more slowly. Incorporation of calcium channels, for inward calcium current, will elevate the plateau of the cardiac action potential and prolong repolarization and refractoriness. In addition, functionally expressing potassium channels would accelerate repolarization and can thus shorten refractoriness. Therefore, by manipulating the sodium, calcium and potassium currents and cell coupling, the characteristics of the cardiac electrical activity can be correspondingly manipulated.

REFERENCES

U.S. Provisional Application No. 60/704,210, filed Jul. 29, 2005 by Brink P R et al.

U.S. Pat. No. 6,783,979, issued Aug. 31, 2004 to Rosen M R et al.

U.S. Provisional Application No. 60/832,515, entitled "Chimeric HCN Channels," filed Jul. 21, 2006.

U.S. Provisional application Ser. No. 11/490,997, entitled "Tandem Cardiac Pacemaker System," filed Jul. 21, 2006.

Biel M, Schneider A, Wahl C (2002) Cardiac HCN channels: Structure, function, and modulation. Trends Cardiovasc Med 12: 202-216.

Beyer E C (1993) Gap junctions. Int Rev Cytol 137C: 1-37 1993.

Clapham D E (1998) Not so funny anymore: pacing channels are cloned. Neuron 21: 5-7.

DiFrancesco D (1993) Pacemaker mechanisms in cardiac tissue. Annu Rev Physiol 55: 455-472.

Elfgang C, Eckert R, Lichtenberg-Frate H, Butterweck A, Traub O, Klein R A, Hulser D F, Willecke K. (1995) Specific permeability and selective formation of gap junction channels in connexin-transfected HeLa cells. J Cell Biol 129: 805-817.

Larsson H P (2002) The Search Is on for the Voltage Sensor-to-gate Coupling. J Gen Physiol 120: 475-481.

Orlic D, Kajstura J, Chimenti S, Jakoniuk I, Anderson S M, Li B, Pickel J, McKay R, Nadal-Ginard B, Bodine D M, Leri A, Anversa P (2001) Bone marrow cells regenerate infarcted myocardium. Nature 410: 701-705.

Pape H C (1996) Queer current and pacemaker: the hyperpolarization-activated cation current in neurons. Annu Rev Physiol 58: 299-327.

Perin E C, Geng Y J, Willerson J T (2003) Adult stem cell therapy in perspective. Circulation 107: 935-938.

Qu J, Kryukova Y, Potapova I A, Doronin S V, Larsen M, Krishnamurthy G, Cohen I S, Robinson R B (2004) MiRP1 modulates HCN2 channel expression and gating in cardiac myocytes. J Biol Chem 279: 43497-43502.

Robinson R B, Siegelbaum S A (2003) Hyperpolarization-activated cation currents: from molecules to physiological function. Annu Rev Physiol 65: 453-480.

Sambrook J, Fritsch E F and Maniatis T (1989) Molecular Cloning: A Laboratory Manual, $2^{nd}$ ed., Cold Spring Harbor Laboratory Press, New York.

Santoro B, Tibbs G R (1999) The HCN Gene Family: Molecular Basis of the Hyperpolarization-Activated Pacemaker Channels. Ann NY Acad Sci 868: 741-764.

Strauer B E, Brehm M, Zeus T, Kostering M, Hernandez A, Sorg R V, Kogler G, Wernet P (2002) Repair of infarcted myocardium by autologous intracoronary mononuclear bone marrow cell transplantation in humans. Circulation 106; 1913-1918.

Valiunas V, Beyer E C, Brink P R (2002) Cardiac gap junction channels show quantitative differences in selectivity. Circ Res 91: 104-111.

Valiunas V, Bukauskas F F, Weingart R (1997) Conductances and selective permeability of connexin43 gap junction channels examined in neonatal rat heart cells. Circ Res 80: 708-719.

Valiunas V, Gemel J, Brink P R, Beyer E C (2001) Gap junction channels formed by coexpressed connexin40 and connexin43. Am J Physiol Heart Circ Physiol 281: H1675-H1689.

Valiunas V, Weingart R, Brink P R (2000) Formation of heterotypic gap junction channels by connexins 40 and 43. Circ Res 86: E42-E49.

Wang H Z, Day N, Valcic M, Hsieh K, Serels S, Brink P R, Christ G J (2001a) Intercellular communication in cultured human vascular smooth muscle cells. Am J Physiol Cell Physiol 281: C75-C88.

What is claimed is:

1. An atrioventricular bypass bridge comprising a tract of gap junction-coupled adult human mesenchymal stem cells obtained from bone marrow, wherein the tract i. is formed in vitro, ii. is at least about 0.5 mm in length, iii. has a first end that is capable of being attached to a first site in the atrium of the heart and a second end that is capable of being attached to a second site in the ventricle of the heart so as to allow the conduction of at least one of a pacemaker signal, pacemaker current, electrical signal, and electrical current across the tract between the two sites, and iv. wherein the adult mesenchymal stem cells functionally express both a sodium channel and a potassium channel which channels are each encoded by a respective nucleic acid that has been introduced into the cells.

2. The bypass bridge of claim 1, wherein the mesenchymal stem cells further functionally express a pacemaker ion channel encoded by a nucleic acid that has been introduced into the cells which channel induces a pacemaker in the cells.

3. The bypass bridge of claim 2, wherein the pacemaker ion channel comprises either a hyperpolarization-activated, cyclic nucleotide-gated (HCN) ion channel or chimera thereof.

4. The bypass bridge of claim 3, wherein the pacemaker ion channel is an HCN chimera that comprises portions of more than one HCN channel isoform.

5. The bypass bridge of claim 4, wherein the portions are selected from the group consisting of an amino terminal portion, an intramembranous portion, and a carboxy terminal portion.

6. The bypass bridge of claim 4, wherein at least one portion of the HCN chimera is encoded by a nucleic acid from a first animal species and at least one of the other two portions is encoded by a nucleic acid from a second animal species.

7. The bypass bridge of claim 4, wherein the HCN chimera is mHCNI12, mHCN212, mHCN312, mHCN412, mHCN114, mHCN214, mHCN314, mHCN414, hHCN112, hHCN212, hHCN312, hHCN412, hHCNI14, hHCN214, hHCN314, or hHCN414.

8. The bypass bridge of claim 7, wherein the HCN chimera is hHCN212 having the sequence set forth in SEQ ID NO:2.

9. The bypass bridge of claim 7, wherein the HCN chimera is mHCN212 having the sequence set forth in SEQ ID NO:6.

10. The bypass bridge of claim 3, wherein the HCN channel is a mutant mHCN2 channel having the sequence set forth in SEQ ID NO: 14 modified such that it comprises E324A-mHCN2, Y331A-mHCN2, R339A-mHCN2, or Y331A, E324A-mHCN2.

11. The bypass bridge of claim 10, wherein the mutant mHCN2 channel comprises E324A-mHCN2.

12. The bypass bridge of claim 3, wherein the pacemaker current is actively propagated by an action potential.

13. The bypass bridge of claim 12, wherein the action potential is a sodium-dependent action potential.

14. The bypass bridge of claim 12, wherein cells in the tract further functionally express a calcium channel and the action potential is a calcium-dependent action potential.

15. The bypass bridge of claim 2, wherein the pacemaker ion channel is expressed in mesenchymal stem cells located in the first end of the tract.

16. The bypass bridge of claim 15, wherein the pacemaker ion channel is expressed in mesenchymal stem cells located in a region extending 0.5 mm from the first end.

17. The bypass bridge of claim 16, wherein the pacemaker current is conducted by electrotonic conduction.

18. The bypass bridge of claim 1, wherein the sodium channel is a skeletal muscle sodium channel (SKM-1).

19. The bypass bridge of claim 18, wherein the skeletal muscle sodium channel (SKM-1) comprises an alpha subunit.

20. The bypass bridge of claim 19, wherein the skeletal muscle sodium channel (SKM-1) further comprises an accessory subunit.

21. The bypass bridge of claim 1, wherein the cells in the tract further functionally express a calcium channel encoded by a nucleic acid that has been introduced into the cells.

22. The bypass bridge of claim 21, wherein the calcium channel is an L-type calcium channel, wherein the alpha subunit is optionally-CaV1.2.

23. The bypass bridge of claim 1, wherein the potassium channel comprises the potassium inwardly-rectifying channel 12 (Kir2.1) alpha subunit or potassium inwardly-rectifying channel, subfamily 1, member 12 (Kir2.2) alpha subunit.

24. The bypass bridge of claim 23, wherein the potassium channels further comprises an accessory subunit.

25. The bypass bridge of claim 1, wherein the mesenchymal stem cells further functionally express a connexin that is a member of the group consisting of Cx43, Cx40, and Cx45.

* * * * *